(12) United States Patent
Meltzer et al.

(10) Patent No.: US 9,758,833 B2
(45) Date of Patent: Sep. 12, 2017

(54) METHODS FOR PREDICTING ESOPHAGEAL ADENOCARCINOMA (EAC)

(75) Inventors: Stephen J. Meltzer, Lutherville, MD (US); Yulan Cheng, Ellicott City, MD (US); Zhe Jin, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1423 days.

(21) Appl. No.: 12/918,438

(22) PCT Filed: Feb. 19, 2009

(86) PCT No.: PCT/US2009/034508
§ 371 (c)(1),
(2), (4) Date: Nov. 9, 2011

(87) PCT Pub. No.: WO2009/105533
PCT Pub. Date: Aug. 27, 2009

(65) Prior Publication Data
US 2012/0053066 A1    Mar. 1, 2012

Related U.S. Application Data

(60) Provisional application No. 61/066,281, filed on Feb. 19, 2008, provisional application No. 61/131,748, filed on Jun. 11, 2008, provisional application No. 61/132,418, filed on Jun. 18, 2008.

(51) Int. Cl.
*C12P 21/06* (2006.01)
*C12Q 1/68* (2006.01)

(52) U.S. Cl.
CPC ...... *C12Q 1/6886* (2013.01); *C12Q 2600/154* (2013.01); *C12Q 2600/156* (2013.01)

(58) Field of Classification Search
CPC .............. C12C 1/6886; C12C 26/154; C12C 2600/156
See application file for complete search history.

(56) References Cited

U.S. PATENT DOCUMENTS

2004/0033490 A1    2/2004    Laird
2004/0170977 A1    9/2004    Laird

OTHER PUBLICATIONS

Jin et al., Hypermethylation of Tachykinin-1 is Associated with a Poor Prognosis in Human Esophageal Squamous Cell Carcinoma, Clin Cancer Res 2007;13(21) Nov. 1, 2007.*

(Continued)

*Primary Examiner* — Reza Ghafoorian
(74) *Attorney, Agent, or Firm* — Johns Hopkins Technology Ventures

(57) ABSTRACT

This invention relates, e.g., to methods for predicting a subject's risk for developing esophageal adenocarcinoma (EAC) or high-grade dysplasia (HGD), comprising determining in a sample from the subject the methylation levels of transcriptional promoter regions of various combinations of, among other genes, (a) cadherin 13, H-cadherin (heart) (CDH13); (b) tachykinin-1 (TAC1); (c) nel-like 1 (NELL1); (d) A-kinase anchoring protein 12 (AKAP12); (e) somatostatin (SST); (f) transmembrane protein with EGF-like and two follistatin-like domains (HPP1); (g) CDKN2a, cyclin-dependent kinase inhibitor 2a (p16); or (h) runt-related transcription factor 3 (RUNX3).

13 Claims, 22 Drawing Sheets

(56) References Cited

OTHER PUBLICATIONS

Wong et al., The study of p16 and p15 gene methylation in head and neck squamous cell carcinoma and their quantitative evaluation in plasma by real-time PCR, European Journal of Cancer 39 (2003) 1881-1887.*

Eads et al., Fields of Aberrant CpG Island Hypermethylation in Barrett's Esophagus and Associated Adenocarcinoma, Cancer Res Sep. 15, 200060; 5021.*

Jin, Z. et al., Hypermethylation of the AKAP12 Promoter is a Biomarker of Barrett's AssociatedEsophagealNeoplasticProgression, Can.Epid.Bio.Prev., Jan. 2008, pp. 111-117, 17(11).

Clement, G. et al., Epigenetic Alteration of the Wnt Inhibitory Factor-1 Promoter occurs Early in the Carcinogenesis of BE, Can. Sci., Nov. 13, 2007, pp. 46-53, vol. 99, No. 1.

Jin, Z. et al., Hypermethylation of Tachykinin-1 is a Potential Biomarker in Human Esophageal Cancer, Clin. Can. Res., Nov. 1, 2007, pp. 6293-6300, vol. 13, No. 21.

Kuester, D. et al., Early Involvement of Death-Associated Protein Kinase Promoter Hypermethylation in the Carcinogenesis of BE, Neoplasia, Mar. 2007, pp. 236-245, vol. 9, No. 3.

Hamilton, J., et al., (2006) "Reprimo methylation is a potential biomarker of barrett's-associated esophageal neoplastic progression" Human Cancer Biology, vol. 12, No. 22, pp. 6637-6642.

Hamilton, J., et al., (2006) "Promoter methylation and response to chemotherapy and radiation in esophageal cancer", Clinical Gastroenterology and Hepatology, vol. 4, pp. 701-708.

Jin, Z., et al., (2007) "Hypermethylation of the nel-like 1 gene is a common and early event and is associated with poor prognosis in early-stage esophageal adenocarcinoma", Oncogene, vol. 26, pp. 6332-6340.

Jin, Z., et al., (2008) "Hypermethylation of the somatostatin promoter is a common, early event in human esophageal aarcinogenesis", Cancer, vol. 112, No. 1, pp. 43-49.

Schulmann, K., et al., (2005) "Inactivation of p16, RUNX3, and HPP1 occurs early in Barrett's-associated neoplastic progression and predicts progression risk", Oncogene, vol. 24, pp. 4138-4148.

* cited by examiner

-1000-TSS-exon1 ataattcaagagctaacaggtattagcttaggatgtgtggcactgttcttaaggcttatatgtattaatacatcatttaaactcacaacaaccccta
taaagcaggggggcactcatattccttcccccttataattacgaaaaatgcaaggtattttcagtaggaaagagaaatgtgagaagtgtgaa
ggagacaggacagtatttgaagctggtctttggatcactgtgcaactctgcttctagaacactgagcacttttctggtctaggaattatgacttt
gagaatggagtccgtccttccaatgactccctccccattttcctatctgcctacaggcagaattctcccccgtccgtattaaataaacctcatctt
ttcagagtctgctcttataccaggcaat§tacacgtctgagaaacccttgccccagacagccgttttacacgcaggagggggaaggggagg
ggaaggagagagcagtccgactctccaaaaggaatcctttgaactagggtttctgacttagtgaaccccgcgctcctgaaaatcaagggtt
gagggggtagggggacactttctagtcgtacaggtgatttcgattctcggtggggctctcacaactaggaaagaatagttttgctttttcttatg
attaaaagaagaagccatactttccctatgacaccaaacaccccgattcaatttggcagttaggaaggttgtatcgcggaggaaggaaacg
gggcggggcggatttcttttaacagagtgaacgcactcaaacacgcctttgctggcaggcggggggagcgcggctgggagcagggag
gccggagggcggtgtgggggcaggtggggaggagcccagtcctccttccttgccaacgctggctctggcgagggctgcttccggctg
gtgcccccggggggagacccaacctggggcgacttcagggggtgccacattcgctaagtgctcggagttaatagcac§TCCTCCGA
GCACTCGCTCACGGCGTCCCCTTGCCTGGAAAGATACCGCGGTCCCTCCAGAGGATT
TGAGGGACAGGGTCGGAGGGGGCTCTTCCGCCAGCACCGGAGGAAGAAAGAGGAG
GGGCTGGCTGGTCACCAGAGGGTGGGGCGGACCGCGTGCGCTCGGCGGCTGCGGA
GAGGGGGAGAGCAGGCAGCGGGCGGCGGGGAGCAGCATGGAGCCGGCGGCGGGG
AGCAGCATGGAGCCTTCGGCTGACTGGCTGGCCACGGCCGCGGCCCGGGGTCGGGT
AGAGGAGGTGCGGGCGCTGCTGGAGGCGGGGGCGCTGCCCAACGCACCGAATAGT
TACGGTCGGAGGCCGATCCAG (SEQ ID NO:1)

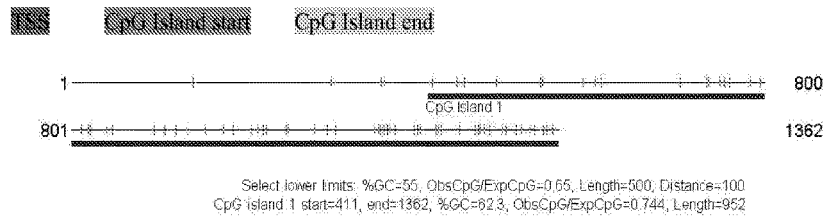

FIG. 1A ataattTaagagTtaaTaggtattagTttaggatgtgtggTaTtgttTttaaggTttatatgtattaataTatTatttaaaTtTaTaaTaa
TTTTtataaagTagggggTaTtTatattTTTttTTTTTtttataattaCgaaaaatgTaaggtattttTagtaggaaagagaaatg
tgagaagtgtgaaggagaTaggaTagtatttgaagTtggtTtttggatTaTtgtgTaaTtTtgTttTtagaaTaTtgagTaTtttttT
tggtTtaggaattatgaTtttgagaatggagtTCgtTtttTtaatgaTtTTTtTTTTattttTTtatTtgTTtaTaggTagaattT
tTTTTCgtTCgtattaaataaaTTtTatTttttTagagtTtgTtTttataTTaggTaatgtaTaCgtTtgagaaaTTTttgTTT
TagaTagTCgttttaTaCgTaggaggggaaggggaggggaaggagagagTagtTCgaTtTtTTaaaaggaatTTtttgaaT
tagggtttTtgaTttagtgaaTTTCgCgTtTTtgaaaatTaagggttgaggggggtaggggggaTaTttttTtagtCgtaTaggtgatt
tCgattTtCggtggggTtTtTaTaaTtaggaaagaatagttttgTttttTtttatgattaaaagaagaagTTataTtttTTTtatgaTa
TTaaaTaTTTCgattTaatttggTagttaggaaggttgtatCgCggaggaaggaaaCggggCgggggCggatttTtttttaaTa
gagtgaaCgTaTtTaaaTaCgTTtttgTtggTaggCggggggagCgCggTtgggagTaggggaggTCggagggCggtgtg
ggggGTaggtggggaggagTTTagtTTtTTtttTTtttgTTaaCgTtggTtTtggCgagggTtgTtttCggTtggtgTTT
TCgggggagaTTTaaTTggggCgaTttTaggggtgTTaTattCgTtaagtgTtCggagttaatagTaT{TTTTTCG
AGTATTCGTTTACGGCGTTTTTTTGTTTGGAAAGATATCGCGGTTTTTTTAGAGGATT
TGAGGGATAGGGTCGGAGGGGGTTTTTCGTTAGTATCGGAGGAAGAAAGAGGAG
GGGTTGGTTGGTTATTAGAGGGTGGGGCGGATCGCGTGCGTTCGGCGGTTGCGGAG
AGGGGGAGAGTAGGTAGCGGCCGGCGGGGAGTAGTATGGAGTCGGCGGCGGGGAG
TAGTATGGAGTTTTCGGTTGATTGGTTGGTTACGT████GTT█GGGT█GGTAG█
█████TC████GG█████TTGT█GGAGGCGGGGCGTTGTTTAACGTATCGAATAGTTACG
GTCGGAGGTCGATTTAG (SEQ ID NO:2)

▓

Probe

Forward primer location

-1000-TSS-exon1 ggttgctagttacaactggaataaattttgtctttcagccccaaagccttaatgctttgcgccaagcaatccagctacaaatttaatttagttcaaa
tacttattgattggctgccatgctcatgtaatacatattatattcaagggtcggaaatgaaaggatgcaagccacttgtgctggtattatttaaagt
cttcatcttttgagaaaggctgacggcaaaggaacagatctatgctgtcatgtgtcggcatcgcgcggagcagaggtggcctggatgggta
acttccagcacaggccctcaaagaaggacgggcacatttccggtaacagcctcatttcccccggttcccggggggaaggggggcggcta
gcactgctgatggcatcgcctgacatcacttgttccggaggataggagagcgtgggcctgcgtggcccacctcatccgtggcctgactgc
gttaacctctcggttccctgctcttgccacgtgaggtgcccaaatatggtcggactcaggaggagccagggagcgcttgccttctcctgcta
atggggaggaggctggaacaaatgtttggagttaaacacacaatctgcaggaaagcaaatgGGGACTCGGACTCGCTCCT
GGGCGAGCTGAAAGTCGGCTGCAGCAGAAGCTCCTGCCTTGGgtgatccatcatttaataaacccc
agagaatccagtgtcccggcaggcttttgctccctgctctcttgccttctgaggccctgggtcgtccccgcagctctagtcgccctgttag
aaacgggaggcgcccgagggccgggtgggcggctgcctggacctgggctggcgcgtcgcagcgcctctggtccggcagcctgggg
gcagatgctgctgcagggcgtgtctggggctgtgctcatgtgatgaagcgagggaaaaaccggggggagggggcggaggctaagag
gtggcctttttttttttttccttttctttttaagcAGTTTGCCGCGAGCGCGTCTCCTTCATTCGCAGGCTGGG
CGCGTTCGCAGTCGGCTGGCGGCGAAGGAAGGCGCTCTCGGGACCTCGCGGGCGCG
CGTCTTTTGGCTCTTGCCCCTGTCCCTGCGGCTTGGGGAAGGCGTAACCCGGCGGCT
AGGCGCGGGAGAAGTGCGGAGGAGCCATGGGCGCCGGGAGCTCCACCGAGCAGCG
CAGCCCGGAGCAGCCGCCCGAGGGGAGCTCCACGCCGGCTGAGCCCGAGCCCAGC
GGCGGCGGCCCCTCGGCCGAGGCGGCGCCAGACACCACCGCGGACCCCGCCATCGC
TGCCTCGGACCCCGCCACCAAG (SEQ ID NO:3)

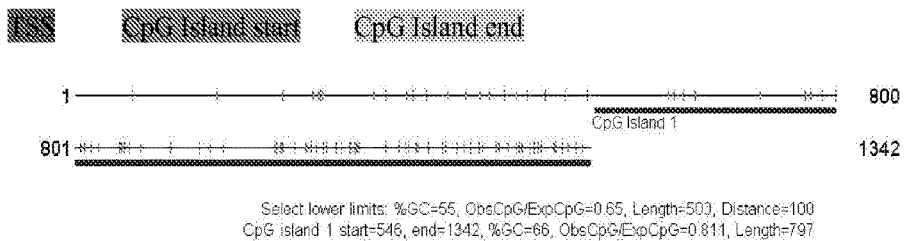

Select lower limits: %GC=55, ObsCpG/ExpCpG=0.65, Length=500, Distance=100
CpG island 1 start=546, end=1342, %GC=66, ObsCpG/ExpCpG=0.811, Length=797

FIG. 2A

-1000-TSS-exon1 ggttgTtagttaTaaTtggaataaattttgtTttttTagTTTTaaagTTttaatgTtttgCgTTaagTaatTTagTtaTaaatttaatt
tagttTaaataTttattgattggTtgTTatgTtTatgtaataTatattatattTaagggtCggaaatgaaaggatgTaagTTaTtttgtg
TtggtattatttaaagtTttTatTttttgagaaaggTtgaCggTaaaggaaTagatTtatgTtgtTatgtgtCggTatCgCgCggag
TagaggtggTTtggatgggtaaTttTTagTaTaggTTTtTaaagaaggaCgggTaTatttTCggtaaTagTTtTatttTTT
TTCgttTTTCggggggaagggggggCggTtagTaTtgTtgatggTatCgTTgaTatTaTtttgttTCggaggataggagag
CgtgggTTtgCgtggTTTaTTtTatTCgtggTTtgaTtgCgttaaTTtTtCggttTTTTgTtTttgTTaCgtgaggtgT
TTaaatatggtCggaTtTaggaggagTTagggagCgTtttgTTtttTtTTtgTtaatgggaggaggTtggaaTaaatgtttgg
agttaaaTaTaatTtgTaggaaagTaaatgGGGATTCGGATTCGTTTTTGGGCGAGTTGAAAGTCGG
TTGTAGTAGAAGTTTTTGTTTTGGgtgatTTatTatttaataaaTTTTagagaatTTagtgtTTTCggTagg
TtttttgTtTTTTtgTtTtTttgTTttTtgaggTTTtgggtCgtTTTCgTagTtTtagtCgTTTtgttagaaaCgggaggC
gTTCgaggg [highlighted] ggTagTTtgggg
gTagatgTtgTtgTagggCgtgtTtggggTtgtgTtTatgtgatgaagCgagggaaaaaTCgggggggagggggggCggaggT
taagaggtggTTtttttttttttttTTttttTttttaag [highlighted] AGTTTGTCGCGAGCGCGTTTTTTTTATTCGTAGGT
TGGGCGCGTTCGTAGTCGGTTGGCGGCGAAGGAAGGCGTTTTCGGGATTTCGCGGG
CGCGCGTTTTTGGTTTTTGTTTTTGTTTTTGCGGTTTGGGGAAGGCGTAATTCGGCG
GTTAGGCGCGGGAGAAGTGCGGAGGAGTTATGGGCGTCGGGAGTTTTATCGAGTAG
CGTAGTTCGGAGTAGTCGTTCGAGGGGAGTTTTACGTCGGTTGAGTTCGAGTTTAGC
GGCGGCGGTTTTTCGGTCGAGGCGGCGTTAGATATTATCGCGGATTTCGTTATCGTT
GTTTCGGATTTCGTTATTAAG  (SEQ ID NO:4)

▨

Probe

Forward primer location

Reverse primer location

FIG. 2B

-1000-TSS-exon1

Ttgctttggctatcaggaagctcttatccaaatcagagcaaatacattagaatttgggcttgtcatttcagtttgctgaacttttccttctggccca
gattttctattttggttcataaattctattgcacaaatgtcctttattgtaaaacaccttaaattctttctaagggaaggctgcatggaaatgatacag
taaggtcttccctgcattttcttagattcctattagggaaggcagacctagatgtccctcttaccctcagtcccaaagcccccatttataaaatc
ccttaagcagtgactactgctgttctgagtacctggaggtagttcagagcttctgaaaggtaacatccatatacaaaaagaagttccttccgat
ccagatcccagctttggtgccagatgcacatttgaggagtaggtggctagtcagactctcacctgagcagttaataaaatctattgccccttaa
tggaattttttctgcaagctcgaattgatctgtcatctttgtgatttgtgagatggcagggaagcaccaaacaccatcatgacttgggccacagt
gggggaaaaaaggaaaaaagaaaaaaaaaatccactgccaagccttgccaggcgtagaaagggctggaactgctggggccattttatc
tgatttattggaaatagagtggatcttattaacattţtaataaagagaatcttttgcactaggctggaagtggccgccagtccccgtgcaattc
cattctctggaaaagtggaatcagctggcattgcccagcgtgatttgtgaggctgagccccaacagtccaaagaagcaaatgggatgccac
ctccgcggggctcgctcctcgcgaggtgctcaccccgtatctgccatgcaaaacgagggagcgttaggaaggaatccgtcttgtaaagcc
attggtcctggtcatcagcctctacccaatgctttcgtgatgctgctgctgatctattţGGAAGTTGGCTGGCTGGCGAG
GCAGAGCCTCTCCTCAAAGCCTGGCTCCCACGGAAAATATGCTCAGTGCAGCCGCG
TGCATGAATGAAAACGCCGCCGGCGCTTCTAGTCGGACAAAATGCAGCCGAGAAC
TCCGCTCGTTCTGTGCGTTCTCCTGTCCCAĢ  (SEQ ID NO:5)

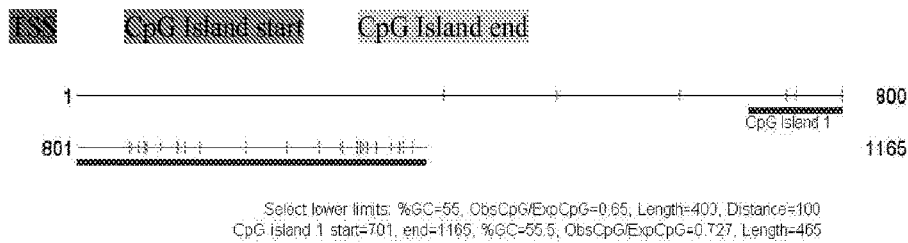

FIG. 3A

-1000-TSS-exon1 ttgTtttggTtatTaggaagTtTttatTTaaatTagagTaaataTattagaatttgggTttgtTatttTagtttgTtgaaTttttTTttTt
ggTTTagattttTtattttggttTataaattTtattgTaTaaatgtTTtttattgtaaaaTaTTttaaattTtttTtaagggaaggTtgTat
ggaaatgataTagtaaggtTttTTTtgTattttTttagattTTtattagggaaggTagaTTtagatgtTTTtTttaTTTtTagtTT
TaaagTTTTTTatttataaaatTTTttaagTagtgaTtaTtgTtgttTtgagtaTTtggaggtagttTagagTttTtgaaaggtaa
TatTTatataTaaaaagaagttTTttTCgatTTagatTTTagTtttggtgTTagatgTaTatttgaggagtaggtggTtagtTag
aTtTtTaTTtgagTagttaataaaatTtattgTTTTTttaatggaattttttTtgTaagTtCgaattgatTtgtTatTtttgtgatttgtga
gatggTagggaagTaTTaaaTaTTatTatgaTttgggTTaTagtggggggaaaaaaggaaaaaagaaaaaaaaaaatTTaTtg
TTaagTTttgTTaggCgtagaaagggTtggaaTtgTtggggTTattttatTtgatttattggaaatagagtggatTttattaaTatttt
aataaagagaatTttttgTaTtaggTtggaagtggTCgTTagtTTTTCgtgTaattTTattTtTtggaaaagtggaatTagTt
ggTattgTTTagCgtgatttgtgaggTtgagTTTTaaTagtTTaaagaagTaaatgggatgTTaTTtTCgCggggTtCg
TtTTtCgCgaggtgTtTaTTTCgtatTtgTTatgTaaaaCgagggagCgttaggaaggaatTCgtTttgtaaagTTattggt
TTtggtTatTagTTtTtaTTTaatgTtttCgtgatgTtgTtgTtgatTtattt GGAAGTTGGTTGGTTGGCGA
GGTAGAGTTTTTTTTAAAGTTTGGTTTTTACGGAAAATATGTTTAGTGTAGT C T
GTATGAATGAAAA T T GG TTTTACT CGGATAAAATGTAGTCGAGAATT
TCGTTCGTTTTGTGCGTTTTTTTGTTTTAG (SEQ ID NO:6)

Probe

Forward primer location

Reverse primer location

FIG. 3B

-1000-TSS-exon1 tggagcccgctctcccttcccggacgccgctgcccggccgatgctcccggcaacccacccgcggcgtatgcagaggagcctttctctt
tctctcagaccacttgtcccgaccaatctgaccttccaaacacatctgaccgcacctcccaggtggacacactaataggctacgggctgga
gaggagcgggtgatgaggagagggattcaaacctgcgaacgcttgggctgggtcggagctgcgggggggcctgggaggagagaggg
gagaagagagaaggaaggagagcgcctgccgggatggctgagctgcctcggcgagcagccttggggttgcacgctcttgtgggagat
gctgctgttgcttccaggtcggcaagagcggttctaacaccatcgcctctcaccctctttcctgtaaatcccctagagaaacgtccctggcctct
ccgccgcgacattcccagcctgcatcccctacagcctaggcggcgcgctcccgcacgctggagcgccggtcgccagcaggacgccct
ctcccgcgccgactcgccctctctgccctgctgctgctgctcctctgacacctccgccccaccatctccagctcggagagacgccaccc
agccgcggcccgcactcgcggcccggggtcacgcgcggaagaggggcgctagtccggaccccgccttcggtaggggcgtcctgga
gcggagagtgaggcgaatggtatatgagtgtgcgggtagcccaccctgaagcccgagcttctcatttgagccatccccgcctagccccac
tcgggccagcgcctggcgagcgagcccatctgtggcttccgcggccgcctcctccttgcatccttgcacctcctcgtcgacccctccctcc
cgggacctgcatcctgctccaccaatcagagcccgactgcctcttcccacgtgacccggcgggctgaggacctgctgcttcccaaacg
ccagagggatgcgggcg CAGAGCTCGAGAGGCGGCTGCCGGGCTGCGGGCGCCTTGACT
CTCCCTCCACCCTGCCTCCTCGGGCTCCACTCGTCTGCCCCTGGACTCCCGTCTCCTC
CTGTCCTCCGGCTTCCCAGAGCTCCCTCCTTATGGCAGCAGCTTCCCGCGTCTCCGG
CGCAGCTTCTCAGCGGACGACCCTCTCGCTCCGGGGCTGAGCCCAGTCCCTGGATGT
TGCTGAAACTCTCGAGATCATGCGCGGGTTTGGCTGCTGCTTCCCCGCCGGGTGCCA
CTGCCACCGCCGCCGCCTCTGCTGCCGCCGTCCGCGGGATGCTCAGTAGCCCGCTGC
CCGGCCCCCGCGATCCTGTGTTCCTCGGAAGCCGTTTGCTGCTGCAGAGTTGCACGA
ACTAGTCATGGTGCTGTGGGAGTCCCCGCGGCAGTGCAGCAGCTGGACACTTTGCG
AGGGCTTTTGCTGGCTGCTGCTGCTGCCCGTCATGCTACTCATCGTAGCCCGCCCGG
TGAAGCTCGCTGC (SEQ ID NO:7)

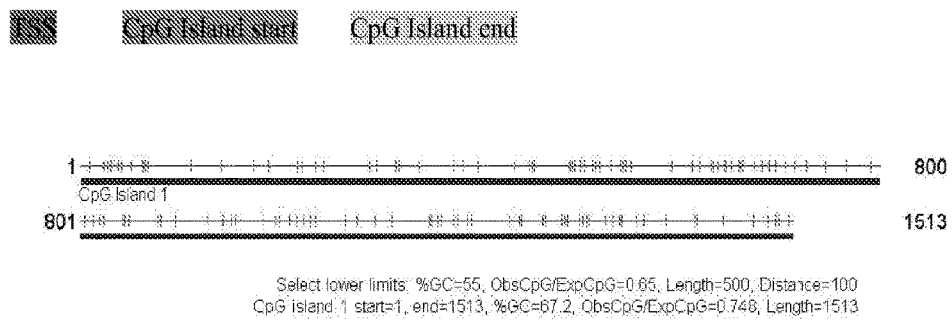

FIG. 4A

-1000-TSS-exon1 atggagTTCgTtTtTTTTttTTCggaCgTCgTtgTTCggTCgatgTtTTCggTaaTTTaTTCgCggCgtatgTa
gaggagTTtttTtTtttTtTtTagaTTaTtttgtTTCgaTTaatTtgaTTttTTaaaTaTatTtgaTCgTaTTtTTTaggtg
gaTaTaTtaataggTtaCgggTtggagaggagCgggtgatgaggagagggattTaaaTTtgCgaaCgTttgggTtgggtCg
gagTtgCggggggTTtgggaggagagaggggagaagagagaaggaaggagagCgTTtgTCgggatggTtgagTtgTTtC
ggCgagTagTTttggggttgTaCgTtTtttgtgggagatgTtgTtgttgTttTTaggtCggTaagagCggttTtaaTaTTatC
gTTtTtTaTTTtTtttTTtgtaaatTTTtagagaaaCgtTTTtggTTtTtTCgTCgCgaTattTTTagTTtgTatTTT
TTtaTagTTtaggCggCgCgTtTTCgTaCgTtggagCgTCggtCgTTagTaggaCgTTTtTtTTCgCgTCga
TtCgTTTTtTtTtgTTTtgTtgTtgTtgTtTTtTtgaTaTTtTCgTTTTTaTTatTtTTagTtCggagagaCgTTa
TTTagTCgCggTTCgTaTtCgCggTTCggggtTaCgCgCggaagaggggCgTtagtTCggaTTTCgTTttCg
gtaggggCgtTTtggagCggagagtgaggCgaatggtatatgagtgtgCgggtagTTTaTTTtgaagTTCgagTttTtTa
tttgagTTatTTTCgTTtagTTTTaTtCgggTTagCgTTtggCgagCgagTTTatTtgtggTttTCgCggTCgTTt
TTtTTttgTatTTttgTaTTtTTtCgtCgaTTTTtTTTtTTCgggaTTtgTatTTtgTtTTaTTaatTagagTTCga
TtgTTtTttTTTaCgtgaTTTCgggCgggTtgaggaTTtgTtgTttTTTaaaCgTTagagggatgCgggCg TAG
AGTTCGAGAGGCGGTTGTCGGGTTGCGGGGCGTTTTGATTTTTTTTTATTTTGTTTT
TTCGGGTTTTATTCGTTTGTTTTGGATTTTCGTTTTTTTTGTTTTCGGTTTTTAGA
GTTTTTTTTTATGGTAGTAGTTTTTCGCGTTTTCGGCGTAGTTTTTAGCGGACGAT
TTTTTCGTTTCGGGGTTGAGTTTAGTTTTTGGATGTTGTTGAAATTTTCGAGATTATG
CGCGGGTTTGGTTGTTGTTTTTCGTCGGTGTTATTGTTATCGTCGTCGTTTTTGTTG
TCGTCGTT   GGATGTTTAGTAGTT  TTGTT  GTTTTCG  ATTTTGTGTTTT
         G AGT GTTGTTGTTGTAGAGTTGTACGAATTAGTTATGGTGTTGTGGGAGTTT
TCGCCGTAGTGTAGTAGTTGGATATTTGCGAGGGTTTTTGTTGGTTGTTGTTGTTGT
TCGTTATGTTATTTATCGTAGTTCGTTCGGTGAAGTTCGTTGTTTTTTTATTTTTTA
AGTGATTGTTAAACGTTATCGGTTGGAATTGTTTT (SEQ ID NO:8)

▓

Probe

Forward primer location

▓▓▓ Reverse primer location

FIG. 4B

-1000-TSS-exon1

Cttgccggcaagtagaaaacaaagcccagcccagcttttctctccagagaatgttgtggtgggagagggaiaagaaggtggaggtcccg
gaggaattgcacatggggccaaaatgtgactatgaaagaagagtgggcttttgataataccattaagaaaatcacgcaagaaagaaaaaaa
gatggttaggaattaccccctatgtggcagcatctgccctgcagaatgagaaggtttgcaaatagacttcccaaacccaaccacagctcgct
ccgcctcgaggaccccttttctgcacccccacctcagcgccctcttcctgcacccacaaagagagtactcagtcataggggttcaacagga
gagaggagacagaaggtacaggcggtgagcagggactcagccatcatcccccctcaggtccctcccacccagttgacagagcgaatcc
cgagtaattgttttccgaggggggtccgtgcgcgctcggtggcgccgcctcggtctgggttccccgaggaaaaatacccaccc gcgagg
gctcggcggcttttcgactcggcggggatgaactgtggcaacttcggcagcccccaccgcggtgcggaagtaaagagggcaacattggc
gactgcggctcggagggctggagcgcgtgaagccgtggggcgccgtgcgcctccgctctctcgtttcggccgcaggtcctgggac
tccgacttcggtgctccgggtgatagcggctgcggcgcctgcagtccagatcctcgcagttctgcgggcgaaggaggcgaacggaatcg
gccccagtggggagcgcaacaagccacagtagccaaaccccgcgctcctgcccggctcccagacgaacgcagccgcagcgggg
ggccgggccccgagccccacgccgccgccgccgcgccagcggtgggggcggctggggcgggcggccggggctgccttccc
gggcgcatatgcgagcgcagcacc.GCGCTGCCGAGCCACCTCCCCCGCCGCCCGCTAGCAAGT
TGGCGGCTCCAAGCCAGGCGCGCCTCAGGATCCAGGCTCATTTGCTTCCACCTAGC
TTCGGTGCCCCCTGCTAGGCGGGGACCCTCGAGAGCGATGCCGATGGATTTGATTTT
AGTTGTGTGGTTCTGTGTGTGCACTGCCAGGACAG (SEQ ID NO:9)

FIG. 5A

-1000-TSS-exon1

TttgTCggTaagtagaaaaTaaagTTTagTTTagTttttTtTtTTagagaatgttgtggtgggagagggaaaagaaggtggag
gtTTCggaggaattgTaTatggggTTaaaatgtgaTtatgaaagaagagtgggTttttgataataTTattaagaaaatTaCgTaa
gaaagaaaaaaagatggttaggaattaTTTTtatgtggTagTatTtgTTTtgTagaatgagaaggtttgTaaatagaTttTTTaa
aTTTTaaTTaTagTtCgTtTCgTTtCgaggaTTTTttttTtgTaTTTTTaTTtTagCgTTTtTttTTtgTaTTTa
TaaagagagtaTtTagtTatagggggttTaaTaggagagaggagaTagaaggtaTaggCggtgagTagggaTtTagTTatTat
TTTTTtTaggtTTTtTTTTaTTTagttgaTagagCgaatTTCgagtaattgttttTCgagggggtTCgtgCgCgTtCg
gtggCgTCgTTtCggtTtgggttTTTTCgaggaaaaataTTTaTTCgCgagggTtCggCggTttttCgaTtCggCgg
ggatgaaTtgtggTaaTttCggTagTTTTTaTCgCggtgCggaagtaaagagggTaaTattggCgaTtgCggTtCggag
gggTtggagCgCgtgaagTCgtggggCgTCgtgCgTTtTTCgTtTtTtCgtttCggTCgTaggtTTtgggaTtTCg
aTttCggtgTtTCgggtgatagCggTtgCggCgTTtgTagtTTagatTTtCgTagttTtgCgggCgaaggaggCgaaC
ggaatCggTTTTTagtggggagCgTaaTaagTTaTagtagTTaaaTTTCgCgTtTTtgTTCgggTtTTTagaCg
aaCgTagTCgTagCgggggggT ggTTTC agTTTTa T TCg T TTa gggggCgg
gTtggggCgggCggTCggggTtgTTttTTCgggCgTatatgCgagCgTagTaTTCgGCGTTGTCGAGTT
ATTTTTTTCGTCGTTCGTTAGTAAGTTTGGCGGTTTTAAGTTAGGCGCGTTTTAGGAT
TTAGGTTTATTTGTTTTTATTTAGTTTCGGTGTTTTTTGTTAGGCGGGGATTTTCGAG
AGCGATGTCGATGGATTTGATTTTAGTTGTGTGGTTTTGTGTGTGTATTGTTAGGATA
G  (SEQ ID NO:10)

▓

Probe

Forward primer location

-1000-TSS-exon1 cagccggagcgcacgggcccaagaagaagtggggttggacccgcagaggccactttccaccCgcatggagaaagaaaattctctcct
ctgaaagcgagggcccttagcttttgcagccactgctgtttttcttttgccaccgacgcgcgtaccgtttcacgatgcaggaccgtggttacatg
cgtaaaggaaaaaaagaaaaacgcattttgcaggcctcgtcgtgtttttcaaagagccacaggccgccacaacgaagaacgacgccgcg
aggcctgcaagatcctgaaacttgttttgaggggagagcagagaggaaaggggttgttggccccaggctacttagggtccctaggagact
cccttccgcctgtccccggtttggcacaggggccacccgaggctgggaccaaagccgcgcagggctgggagcagcaaaggccgccgg
ccgggcgtggacgacgcgcaaaatcccgtgtggggtggaggctcttgggtcagaataatgtgcgggacgagggaggtgagtaacctctt
tggggcggctcccagtgcggcgtcaccggccctgagacccCgcggccccagcccggggttgcagaagtcacaggcccgaagcagc
aagagctggggaagcccggccgcgccagcggggaggaggagcgaaggggttgcgcccagcgtcagggagctacgaccCgaga
gagggcggcaagggcgccttccgtgggaccCggacgttctaagcaaatttctagcatttgccccgggctcccagagctctcggggccct
gggctgtggcactggggcctcctccgcggggtggCgccttccgcccctcccCgttgggcggcctccggcaggcccCgttcctcccCgcg
aacgccaccgaggtgcccgcgatgggggctccgccgattggctgtgcgacgcgtcgctccgccagcccCgccccgcgggcccCggg
ggtactaaccccgcgcgggcggccgcgcCCGCCACTTGATTCTGGAGGATTTGTTCTGGGGCTGC
GGCCGCGGAGTCGGGGCGGCCGCGGGCGAGCTTCGGGGCGGGAGGCGGCGGCAGC
GGCACAGCCCCGCGCGGGCCCCGCCGCGGCCCAGGCAGCCGGGACAGCCACGAGG
GGCGGCCGCACGCGGGGCCGCGCGCCGAGGATGCGGGACTAGCCGGGCAGGCTGC
GGGCGGCCGTCGGGCCAGCGAGGCCTCGCAGCGGGCGGGCCCTGGCGAGTAGTGG
CCGGGCGCCGCCCCCTGCGCCCTGAGGCCCGGCCCCGCCGCTTCTGCTTTCCCGCT
TCTCGCGGCAGCGGCGGCCGAGGAGGCGCCCGCGCCGGCCGCCCCCGGGGAAGC
CGCGCCGTCTCCGCCTGCCCGGCGCCCTGACGGCCGCTGTTATGCGTATTCCCGTAG
ACCCAAGCACCAGCCGCCGCTTCACACCTCCCTCCCCGGCCTTCCCCTGCGGCGGCG
GCGGCGGCAAGATGGGCGAGAACAGCGGCGCGCTGAGCGCGCAGGCGGCCGTGGG
GCCCGGAGGGCGCGCCCGGCCCGAGGTGCGCTCGATGGTGGACGTGCTGGCGGACC
ACGCAGGCGAGCTCGTGCGCACCGACAGCCCCAACTTCCTCTGCTCCGTGCTGCCCT
CGCACTGGCGCTGCAACAAGACGCTGCCCGTCGCCTTCAAG (SEQ ID NO:11)

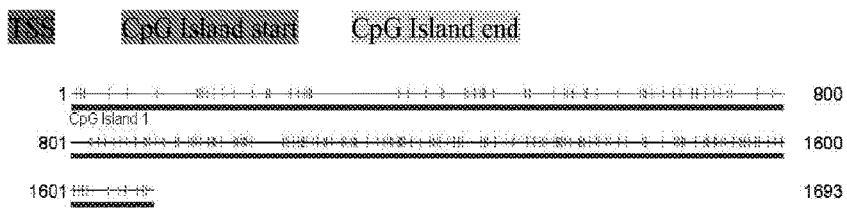

FIG. 6A

-1000-TSS-exon1 gTagTCggagCgTaCgggTTTaagaagaagtggggttggaTTCgTagaggTTaTtttTTaTTCgTatggagaaagaa
aattTtTtTTtTtgaaagCgagggTTTtttagTtttgTagTTaTtgTtgttttttTttttgTTaTCgaCgCgCgtaTCgtttTaC
gatgTaggaTCgtggttaTatgCgtaaaggaaaaaaagaaaaaCgTattttgTaggTTtCgtCgtgtttttTaaagagTTaTag
gTCgTTaTaaCgaagaaCgaCgTCgCgaggTTtgTaagatTTtgaaaTtttgttttgaggggagagTagagaggaaaggg
gttgttggTTTTaggTtaTtttagggtTTTtaggagaTtTTTttTCgTTtgtTTTCggtttggTaTagggggTTaTCgagg
TtgggaTTaaagTCgCgTagggTtgggagTagTaaaggTCgTCggTCgggCgtggaCgaCgCgTaaaatTTCgtg
tggggtggaggTtTttgggtTagaataatgtgCgggaCgagggaggtgagtaaTTtTttttggggCggTtTTTagtgCggCgt
TaTCggTTTTtgagaTTTCgCggTTTTTagTTCggggttgTagaagtTaTaggTTCgaagTagTaagagTtgggg
aagTTCggTCgCggTTagCggggaggaggagCgaaggggttgCgTTTTagCgtTagggagTtaCgaTTCgagaga
gggCggTaagggCgTTttTCgtgggaTTCggaCgttTtaagTaaatttTtagTattgTTTCgggTtTTTagagTtTtC
gggggTTTtgggTtgtggTaTtggggTTtTTtTCgCggggtggCgTTttTCgTTTTtTTTCgttgggCggTTtTC
ggTaggTTTCgttTTtTTTCgCgaaCgTTaTCgaggtgTTCgCgatggggggTtTCgTCgattggTtgtgCgaCg
CgtCgTtCgTTagTTTCgTTTCgCgggTTTCgggggtaTtaaTTTCgCgCgggCggTCgCggT**TCGT
TATTTGATTTTGGAGGATTTGTTTTGGGGTTGCGGTCGCGGAGTCGGGGCGGTCGCG
GGCGAGTTTCGGGGCGGGAGGCGGCGGTAGCGGTATAGTTTCGCGCGGGTTTCGTC
GCGGTTTAGGTAGTCGGGATAGTTACGAGGGGCGGTCGTACGCGGGGTCGCGCGTC
GAGGATGCGGGATTAGTCGGGTAGGTTGCGGGCGGTCGTCGGGTTAGCGAGGTTTC
GTAGCGGGCGGGTTTTGGCGAGTAGTGGTCGGGCGTCGTTTTTGCGTTTTGAGGTT
CGGGTTTCGTCGTTTTGTTTTTCGTTTTTCGCGGTAGCGGCGGTCGAGGAGGGT
CGGGTCGGTCGTTTCGGGGGAAGTCGCGTCGTTTTCGTTTGTTCGGCGTTTTGACG
GTCGTTGTTATGCGTATTTTCGTAGATTTAAGTATTAGTCGTCGTTTTATATTTTTTT
TTCGGTTTTTTTTTGCGGCGGCGGCGGCGGTAAGATGGGCGAGAATAGCGGCGCGT
TGAGCGCGTAGGCGGTCGTGGGGTTCGGAGGGCGCGTTCGGTTCGAGGTGCGTTCG
ATGGTGGACGTGTTGGCGGATTACGTAGGCGAGTTCGTGCGTATCGATAGTTTTAAT
TTTTTTTGTTTCGTGTTGTTTTCGTATTGGCGTTGTAATAAGACGTTGTTCGTCGTTTT
TAA (SEQ ID NO:12)

▓ TSS

▓ Probe

▓ Forward primer location

▓ Reverse primer location

FIG. 6B

-1000-TSS-exon1 gtTaTatatgttTtgggagttTTtagaTTttatatgtTtaaaTtggggTttTTtgaTataaaaTtatgTttaTCggTTaggaatTtg
ttagaaaaTtTagagTtTagtagaaggaaTaTtggTtttggaatgtggaggtTtggttttgTtTaaagtgtgTagtatgtgaaggaga
aTaatttaTtgaTTattaTtTtgTTttaTtgattTaaattTtgaggtttattgaataatttTttagattgTTttTTagTtTtaaatttTtTa
gTaTTaaaatgaagtTTattTaatTtTtTtTtTtTtTtttTTTtTTCgtaTatataTaTaTtTataTatatatatggtTaTa
atagaaaggTaggtagatTagaagtTtTagttgTtgagaaagagggagggagggtgagTTagaggtaTTttTtTTTTTattgta
gagaaaagtgaagttTttttagagTTTCgttaTatTttTaaggTtttttatgagataatgaggaaataaagagggTtTagtTTttTta
TtgtTTatatttTattTtTaaatTtgttattagaggaatgattTtgatTtTTaTTtaTTataTaTatgTTTtgttgTttgttgggTTtt
TTtaaaatgttagagtatgatgaTagatggagttgtTtgggtaTatttgtgtgTatttaagggtgatagtgtatttgTtTtttaagagTtgag
tgtttgagTTtTtgtttgtgtgtaattgagtgtgTatgtgtgggagtgaaattgtggaatgtgtatgTtTatagTaTtgagtgaaaataaaa
gattgtataaatCgtggggTatgtggaattgtgtgtgTTtgtgCgtgtgTagtattttttttttttttaagtaagTTaTtttagatTttgtTaT
TtTTTTtgtTttTtgtgattgattttgCgaggTtaatggtgCgtaaaagggTtggtgagatTtggggg.........
..............GTTTGTTGATTCGCGTTTAGAGTTTGATTAGTTATTTTT
TAGTTCGGTTTTCGCGGCGTCGAGATGTTGTTTTGTCGTTTTTAGTGCGCGTTGGTTG
CGTTGTTTATCGTTTTGGTTTTGGGTTGTGTTATCGGCGTTTTTTCGGATTTTAGATTT
CGTTAGTTTTTGTAGAAGTTTTTGGTTGTTGTCGCGGGGAAGTAG (SEQ ID NO:13)

Probe

Forward primer location

FIG. 7A

-1000-TSS-exon1 gtcacatatgttctgggagttcctagaccttatatgtctaaactggggcttcctgacataaaactatgcttaccggccaggaatctgttagaaaa
ctcagagctcagtagaaggaacactggctttggaatgtggaggtctggttttgctcaaagtgtgcagtatgtgaaggagaacaatttactgac
cattactctgccttactgattcaaattctgaggtttattgaataatttcttagattgccttccagctctaaatttctcagcaccaaaatgaagtccattt
caatctctctctctctctttccctcccgtacatatacacacactcatacatatatggtcacaatagaaaggcaggtagatcagaagtctcagtt
gctgagaaagagggagggagggtgagccagaggtaccttctcccccattgtagagaaaagtgaagttcttttagagccccgttacatcttc
aaggcttttatgagataatggaggaaataaagagggctcagtccttctactgtccatatttcattctcaaatctgttattagaggaatgattctga
tctccacctaccatacacatgccctgttgcttgttgggccttcctaaaatgttagagtatgatgacagatggagttgtctgggtacatttgtgtgc
atttaagggtgatagtgtatttgctctttaagagctgagtgtttgagcctctgtttgtgtgtaattgagtgtgcatgtgtggagtgaaattgtgga
atgtgtatgctcatagcactgagtgaaaataaaagattgtataaatcgtggggcatgtggaattgtgtgtgcctgtgcgtgtgcagtattttttttt
ttttaagtaagccactttagatcttgtcacctcccctgtcttctgtgattgattttgcgaggctaatggtgcgtaaaagggctggtgagatctggg
ggcgcctcctagcctgacgtcagagagagagtttaaaacaga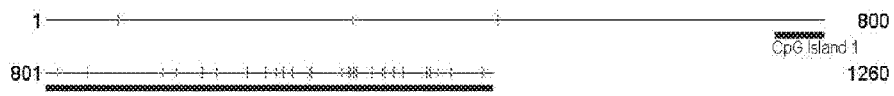GGAGACGGTTGAGAGCACACAAGCCGCT
TTAGGAGCGAGGTTCGGAGCCATCGCTGCTGCCTGCTGATCCGCGCCTAGAGTTTGA
CCAGCCACTCTCCAGCTCGGCTTTCGCGGCGCCGAGATGCTGTCCTGCCGCCTCCAG
TGCGCGCTGGCTGCGCTGTCCATCGTCCTGGCCCTGGGCTGTGTCACCGGCGCTCCC
TCGGACCCCAGACTCCGTCAGTTTCTGCAGAAGTCCCTGGCTGCTGCCGCGGGGAA
GCAG  (SEQ ID NO:14)

FIG. 7B

-1000-TSS-exon1 ataTtaaaaaatTataattaattgaaaaatataataTttTatatgtaaaggggagaaaaTtaTtTTaTTaaagatgtTaTatTtttaatt
TatttggagatTaaagaaatgtgtTtgTTaggTaaTTaagggTtTatggaaaggtgtggtttTtgtaTaaatgTtatttgtTtaatatt
ttgtgTtgttaatgaTtgtTTTattagTatTttTaTtaTaTttaTtttTatagaaaggagaaaTatgatttatagagTTTtttagtgaTa
agggtgaggatTTtaTaTaTtatgttgTtggtttTTtagtTttTagTaagaaagtgtaggagagaagTaaaaaaCgtTTtgttTaa
TTTTtgTtTTtggatgtggTaaggaagaggagttaTTCggTttgaaaTaaaagaaatTTtaagtTtgaTaTaTaatgtTatgtt
taaattTTTTtttTtTTaaaatgtaaaataaatTtgTttTTatTttTtaaaataTtatgggaTtaaaTatTTtttgttatgTtaaggaa
aagTTagtattCgCgttgatttagaagagggatgttTtggttatagaaCgatgTtgtgtTtTagaaaTaTttaaataTtattaagTtag
aaatagaagggaaaataatgTttTTTCgTatTtTTTTtTaagtgtagtTTtTttttttagTTtgatttTCgaCgaaatgtTtgaat
gTTtaTagttatttggTTatTTtgaaaagtgTaaTttatTTtgaCgtTtCgagggaCggaaaagttaTCgaagtTTaaggaatg
agtTaTtttgTtTaaatttgatgagtaatatTaggtgtTatgaaaTTTagtttCgaaggagagggaggggCgtTagatTtgTag
aCggaagTaggTCgTtTCggattggatggCgagaTTtCgattttTTtaaaattgCgtTatttagaaTTTaattgggtTTagat
gttatgggTatCgaCgagttaTCgtTtCggaaaTtTtTaat§ACGTAAGCGAAAGGAGAGGAGGCCGTT
AATTAAATATTGAGTAGAAAGTCGCGTGGGGAGAATGTTACCTGGGTTTGGAGGTT
TAAGGAGGTTGGGATAAATATCGTAAGGTATTGAGTAGG AAAGAG TT G
XXXXTTTTCGGCGGTAGTTATCGAGAGTGCGGAGCGATTAGCGTGCGTTCGGAGG
AATTAGAGAAATTTAGTATTTCGCGGGATTGTTCGTCGTA (SEQ ID NO:15)

▓ TSS

▓ Probe

Forward primer location

▓ Reverse primer location

FIG. 8A

-1000-TSS-exon1 atactaaaaaatcataattaattgaaaaatataatacttcatatgtaaaggggagaaaactactccaccaaagatgtcacatcttttaattcatttg
gagatcaaagaaatgtgtctgccaggcaaccaagggctcatggaaaggtgtggtttctgtacaaatgctatttgtctaatattttgtgctgttaat
gactgtcccattagcatcttcactacacttactttcatagaaaggagaaacatgatttatagagcccctttagtgacaagggtgaggatcctaca
cactatgttgctggtttcctagtcttcagcaagaaagtgtaggagagaagcaaaaaacgtcctgttcaacccctgctcctggatgtggcaagg
aagaggagttacccggcttgaaacaaaagaaatcctaagtctgacacacaatgtcatgtttaaattccccttctccaaaatgtaaaataaatct
gcttccatcttctaaaatactatgggactaaacatccttttgttatgctaaggaaaagccagtattcgcgttgatttagaagagggatgttctggtt
atagaacgatgctgtgtctcagaaacacttaaatactattaagctagaaatagaagggaaaataatgcttcccogcatctcccctcaagtgta
gtcctcttttttagcctgatttccgacgaaatgtctgaatgcctacagttatttggccatcctgaaaagtgcaactTtcctgacgtctcgaggg
acggaaaagttaccgaagtccaaggaatgagtcactttgctcaaatttgatgagtaatatcaggtgtcatgaaacccagtttcgaaggagag
gggagggggcgtcagatctgcagacggaagcaggccgctccggattggatggcgagacctcgattttcctaaaattgcgtcatttagaac
ccaattgggtccagatgttatgggcatcgacgagttaccgtctcggaaactctcaat<u>A</u>ACGCAAGCGAAAGGAGAGGA
GGCGGCTAATTAAATATTGAGCAGAAAGTCGCGTGGGGAGAATGTCACGTGGGTCT
GGAGGCTCAAGGAGGCTGGGATAAATACCGCAAGGCACTGAGCAGGCGAAAGAGC
GCGCTCGGACCTCCTTCCCGGCGGCAGCTACCGAGAGTGCGGAGCGACCAGCGTGC
GCTCGGAGGAACCAGAGAAACTCAGCACCCCGCGGGACTGTCCGTCGCA (SEQ ID
NO:16)

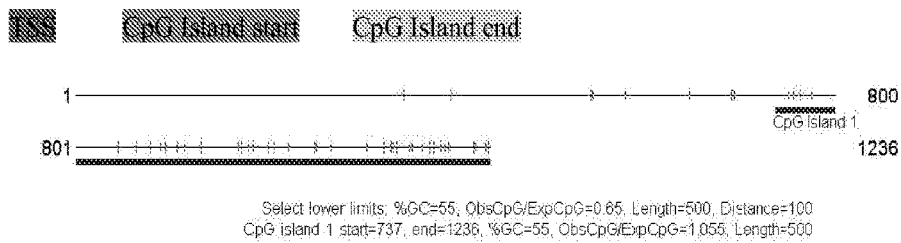

Select lower limits: %GC=55, ObsCpG/ExpCpG=0.65, Length=500, Distance=100
CpG island 1 start=737, end=1236, %GC=55, ObsCpG/ExpCpG=1.055, Length=500

FIG. 8B

A. 8-marker panel in combined model
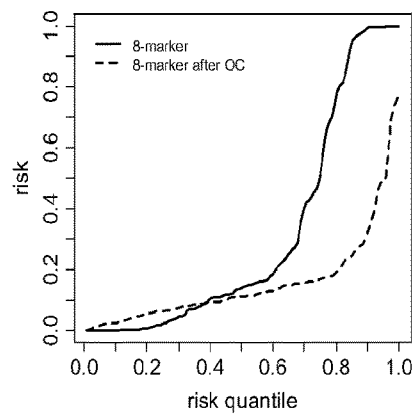
B. Age and 8-marker panel plus age in combined model
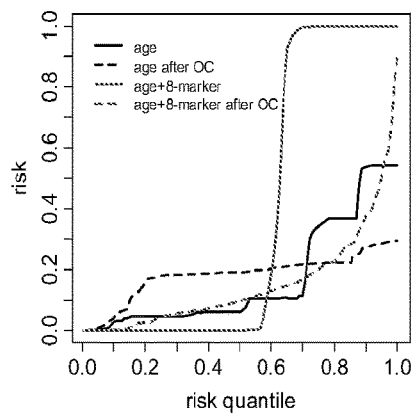
C. 8-marker panel in 2-year model
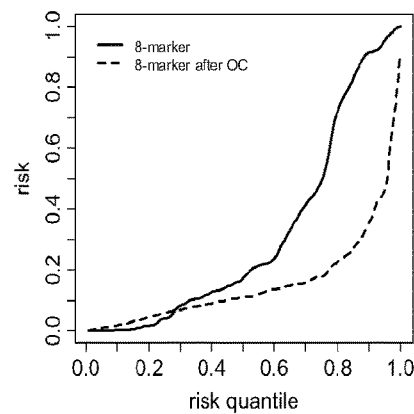
D. Age and 8-marker panel plus age in 2-year model
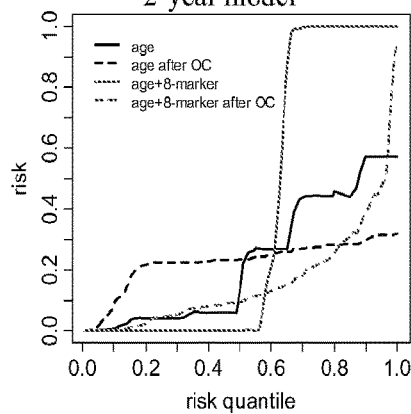
E. 8-marker panel in 4-year model
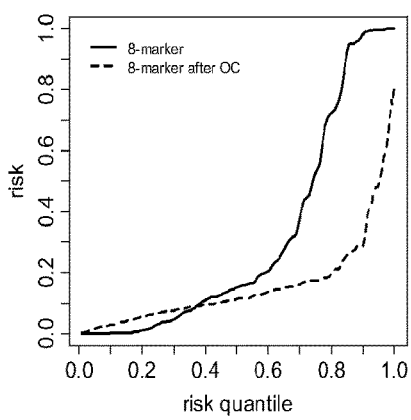
F. Age and 8-marker panel plus age in 4-year model
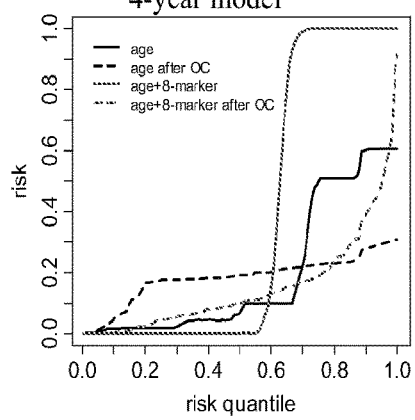
FIG. 13

SEQUENCE LISTING

<160> NUMBER OF SEQ ID NOS: 295

<210> SEQ ID NO 1
<211> LENGTH: 1362

```
<212> TYPE: DNA
<213> ORGANISM: Homo sapiens

<400> SEQUENCE: 1
ataattcaag agctaacagg tattagctta ggatgtgtgg cactgttctt aaggcttata      60
tgtattaata catcatttaa actcacaaca acccctataa agcaggggc actcatattc      120 ccttcccct ttataattac gaaaaatgca aggtattttc agtaggaaag agaaatgtga      180
gaagtgtgaa ggagacagga cagtatttga agctggtctt tggatcactg tgcaactctg     240
cttctagaac actgagcact ttttctggtc taggaattat gactttgaga atggagtccg     300
tccttccaat gactccctcc ccattttcct atctgcctac aggcagaatt ctccccgtc     360 cgtattaaat aaacctcatc ttttcagagt ctgctcttat accaggcaat gtacacgtct     420
gagaaaccct tgccccagac agccgtttta cacgcaggag gggaagggga ggggaaggag     480
agagcagtcc gactctccaa aaggaatcct ttgaactagg gtttctgact tagtgaaccc     540
cgcgctcctg aaaatcaagg gttgagggg taggggaca cttctagtc gtacaggtga       600 tttcgattct cggtggggct ctcacaacta ggaaagaata gttttgcttt tccttatgat     660
taaaagaaga agccatactt tccctatgac accaaacacc ccgattcaat ttggcagtta     720
ggaaggttgt atcgcggagg aaggaaacgg ggcggggcg gatttctttt taacagagtg     780
aacgcactca aacacgcctt tgctggcagg cggggagcg cggctgggag cagggaggcc     840
ggagggcggt gtggggca ggtggggagg agcccagtcc tccttccttg ccaacgctgg       900
ctctggcgag ggctgcttcc ggctggtgcc ccgggggag acccaacctg gggcgacttc     960
aggggtgcca cattcgctaa gtgctcggag ttaatagcac ctcctccgag cactcgctca    1020
cggcgtcccc ttgcctggaa agataccgcg gtccctccag aggattgag ggacagggtc     1080 ggagggggct cttccgccag caccggagga agaaagagga ggggctggct ggtcaccaga    1140
gggtggggcg gaccgcgtgc gctcggcggc tgcggagagg gggagagcag gcagcgggcg    1200
gcggggagca gcatggagcc ggcggcgggg agcagcatgg agccttcggc tgactggctg    1260
gccacggccg cggcccgggg tcgggtagag gaggtgcggg cgctgctgga ggcggggcg    1320 ctgcccaacg caccgaatag ttacggtcgg aggccgatcc ag                       1362

<210> SEQ ID NO 2
<211> LENGTH: 1362
<212> TYPE: DNA
<213> ORGANISM: Homo sapiens

<400> SEQUENCE: 2
ataatttaag agttaatagg tattagttta ggatgtgtgg tattgttttt aaggtttata      60
tgtattaata tattatttaa atttataata atttttataa agtagggggt atttatattt     120
tttttttttt ttataattac gaaaaatgta aggtattttt agtaggaaag agaaatgtga    180
gaagtgtgaa ggagatagga tagtatttga agttggtttt tggattattg tgtaattttg   240
tttttagaat attgagtatt ttttttggtt taggaattat gattttgaga atggagttcg    300
tttttttaat gatttttttt ttattttttt atttgtttat aggtagaatt tttttttcgtt    360 cgtattaaat aaatttatt ttttagagt ttgttttat attaggtaat gtacgtttt         420 gagaaatttt tgttttagat agtcgtttta tacgtaggag gggaagggga ggggaaggag    480
agagtagttc gattttttaa aaggaatttt ttgaattagg ttttttgatt tagtgaattt     540
cgcgtttttg aaaattaagg gttgagggg taggggata ttttttagtc gtataggtga       600
```

```
tttcgatttt cggtggggtt tttataatta ggaaagaata gttttgtttt tttttatgat    660
taaaagaaga agttatattt tttttatgat attaaatatt tcgatttaat ttggtagtta    720
ggaaggttgt atcgcggagg aaggaaacgg ggcgggggcg gattttttt taatagagtg     780 aacgtattta aatacgtttt tgttggtagg cggggggagcg cggttgggag tagggaggtc   840
ggagggcggt gtgggggta ggtggggagg agtttagttt tttttttttg ttaacgttgg    900
ttttggcgag ggttgttttc ggttggtgtt ttcgggggag atttaatttg gggcgatttt    960
aggggtgtta tattcgttaa gtgttcggag ttaatagtat tttttcgag tattcgttta    1020 cggcgttttt ttgtttggaa agatatcgcg gttttttttag aggatttgag ggataggtc   1080 ggaggggggtt ttttcgttag tatcggagga agaaagagga ggggttggtt ggttattaga  1140
gggtggggcg gatcgcgtgc gttcggcggt tgcggagagg gggagagtag gtagcgggcg   1200
gcggggagta gtatggagtc ggcggcgggg agtagtatgg agttttcggt tgattggttg   1260
gttacggtcg cggttcgggg tcgggtagag gaggtgcggg cgttgttgga ggcggggggcg  1320 ttgtttaacg tatcgaatag ttacggtcgg aggtcgattt ag                       1362

<210> SEQ ID NO 3
<211> LENGTH: 1342
<212> TYPE: DNA
<213> ORGANISM: Homo sapiens

<400> SEQUENCE: 3
ggttgctagt tacaactgga ataaattttg tctttcagcc ccaaagcctt aatgctttgc    60
gccaagcaat ccagctacaa atttaattta gttcaaatac ttattgattg ctgccatgc   120 tcatgtaata catattatat tcaagggtcg gaaatgaaag gatgcaagcc acttgtgctg   180
gtattattta aagtcttcat cttttgagaa aggctgacgg caaaggaaca gatctatgct   240
gtcatgtgtc ggcatcgcgc ggagcagagg tggcctggat gggtaacttc cagcacaggc   300
cctcaaagaa ggacgggcac atttccggta acagcctcat ttcccccgt tccccgggg    360 aaggggggcg gctagcactg ctgatggcat cgcctgacat cacttgttcc ggaggatagg   420
agagcgtggg cctgcgtggc ccacctcatc cgtggcctga ctgcgttaac ctctcggttc   480
cctgctcttg ccacgtgagg tgcccaaata tggtcggact caggaggagc cagggagcgc   540 ttgccttttct cctgctaatg gggaggaggc tggaacaaat gtttggagtt aaacacaatc   600
tgcaggaaag caaatgggga ctcggactcg ctcctgggcg agctgaaagt cggctgcagc   660
agaagctcct gccttgggtg atccatcatt taataaaccc cagagaatcc agtgtccccg   720
gcaggctttt tgctcccctg ctctcttgcc ttctgaggcc ctgggtcgtc cccgcagctc   780
tagtcgccct gttagaaacg ggaggcgccc gagggccggg tggcggctg cctgacctg    840 ggctggcgcg tcgcagcgcc tctggtcccg gcagcctggg ggcagatgct gctgcagggc   900
gtgtctgggg ctgtgctcat gtgatgaagc gagggaaaaa ccggggggag ggggcggag    960 gctaagaggt ggccttttt tttttttcct tttcttttaa ggagtttgcc gcgagcgcgt   1020
ctccttcatt cgcaggctgg gcgcgttcgc agtcggctgg cggcgaagga aggcgctctc   1080
gggacctcgc gggcgcgcgt cttttggctc ttgcccctgt ccctgcggct tggggaaggc   1140
gtaacccggc ggctaggcgc gggagaagtg cggaggagcc atgggcgccg ggagctccac   1200
cgagcagcgc agcccggagc agccgcccga ggggagctcc acgccggctg agcccgagcc   1260
cagcggcggc ggcccctcgg ccgaggcggc gccagacacc accgcggacc ccgccatcgc   1320
tgcctcggac cccgccacca ag                                           1342
```

<210> SEQ ID NO 4
<211> LENGTH: 1342
<212> TYPE: DNA
<213> ORGANISM: Homo sapiens

<400> SEQUENCE: 4

| ggttgttagt | tataattgga | ataaattttg | ttttttagtt | ttaaagtttt | aatgttttgc | 60 |
| gttaagtaat | ttagttataa | atttaattta | gtttaaatat | ttattgattg | gttgttatgt | 120 |
| ttatgtaata | tatattatat | ttaagggtcg | gaaatgaaag | gatgtaagtt | atttgtgttg | 180 |
| gtattattta | aagttttat | tttttgagaa | aggttgacgg | taaaggaata | gatttatgtt | 240 |
| gttatgtgtc | ggtatcgcgc | ggagtagagg | tggtttggat | gggtaatttt | tagtataggt | 300 |
| ttttaaagaa | ggacgggtat | attttcggta | atagttttat | ttttttttcgt | ttttcggggg | 360 |
| aaggggggcg | gttagtattg | ttgatggtat | cgtttgatat | tatttgtttc | ggaggatagg | 420 |
| agagcgtggg | tttgcgtggt | ttatttttatt | cgtggtttga | ttgcgttaat | ttttcggttt | 480 |
| tttgttttttg | ttacgtgagg | tgtttaaata | tggtcggatt | taggaggagt | tagggagcgt | 540 |
| ttgttttttt | tttgttaatg | gggaggaggt | tggaataaat | gtttggagtt | aaatataatt | 600 |
| tgtaggaaag | taaatgggga | ttcggattcg | tttttgggcg | agttgaaagt | cggttgtagt | 660 |
| agaagttttt | gttttgggtg | atttattatt | taataaattt | tagagaattt | agtgttttcg | 720 |
| gtaggttttt | tgtttttttg | ttttttttgtt | ttttgaggtt | ttgggtcgtt | ttcgtagttt | 780 |
| tagtcgtttt | gttagaaacg | ggaggcgttc | gagggtcggg | tgggcggttg | tttggattg | 840 |
| ggttggcgcg | tcgtagcgtt | tttggtttcg | gtagtttggg | ggtagatgtt | gttgtagggc | 900 |
| gtgtttgggg | ttgtgtttat | gtgatgaagc | gagggaaaaa | tcggggggag | ggggcggag | 960 |
| gttaagaggt | ggttttttttt | tttttttttt | ttttttttaa | ggagtttgtc | gcgagcgcgt | 1020 |
| tttttttatt | cgtaggttgg | gcgcgttcgt | agtcggttgg | cggcgaagga | aggcgttttc | 1080 |
| gggatttcgc | gggcgcgcgt | tttttggttt | ttgttttttgt | ttttgcggtt | tggggaaggc | 1140 |
| gtaattcggc | ggttaggcgc | gggagaagtg | cggaggagtt | atgggcgtcg | ggagttttat | 1200 |
| cgagtagcgt | agttcggagt | agtcgttcga | ggggagtttt | acgtcggttg | agttcgagtt | 1260 |
| tagcggcggc | ggttttcgg | tcgaggcggc | gttagatatt | atcgcggatt | tcgttatcgt | 1320 |
| tgtttcggat | ttcgttatta | ag | | | | 1342 |

<210> SEQ ID NO 5
<211> LENGTH: 1165
<212> TYPE: DNA
<213> ORGANISM: Homo sapiens

<400> SEQUENCE: 5

| ttgctttggc | tatcaggaag | ctcttatcca | aatcagagca | aatacattag | aatttgggct | 60 |
| tgtcatttca | gtttgctgaa | cttttccttc | tggcccagat | tttctatttt | ggttcataaa | 120 |
| ttctattgca | caaatgtcct | ttattgtaaa | acaccttaaa | ttctttctaa | gggaaggctg | 180 |
| catggaaatg | atacagtaag | gtcttccctg | cattttctta | gattcctatt | agggaaggca | 240 |
| gacctagatg | tccctcttac | cctcagtccc | aaagccccccc | atttataaaa | tcccttaagc | 300 |
| agtgactact | gctgttctga | gtacctggag | gtagttcaga | gcttctgaaa | ggtaacatcc | 360 |
| atatacaaaa | agaagttcct | tccgatccag | atcccagctt | tggtgccaga | tgcacatttg | 420 |
| aggagtaggt | ggctagtcag | actctcacct | gagcagttaa | taaaatctat | tgcccctaa | 480 |

| | | |
|---|---|---|
| tggaatttttt tctgcaagct cgaattgatc tgtcatctttt gtgatttgtg agatggcagg | 540 | |
| gaagcaccaa acaccatcat gacttgggcc acagtgggggg gaaaaaagga aaaagaaaa | 600 | |
| aaaaaatcca ctgccaagcc ttgccaggcg tagaaagggc tggaactgct ggggccattt | 660 | |
| tatctgatttt attggaaata gagtggatct tattaacatt ttaataaaga gaatctttttt | 720 | |
| gcactaggct ggaagtggcc gccagtcccc cgtgcaattc cattctctgg aaaagtggaa | 780 | |
| tcagctggca ttgcccagcg tgatttgtga ggctgagccc caacagtcca agaagcaaa | 840 | |
| tgggatgcca cctccgcggg gctcgctcct cgcgaggtgc tcaccccgta tctgccatgc | 900 | |
| aaaacgaggg agcgttagga aggaatccgt cttgtaaagc cattggtcct ggtcatcagc | 960 | |
| ctctacccaa tgctttcgtg atgctgctgc tgatctatttt gggaagttgg ctggctggcg | 1020 | |
| aggcagagcc tctcctcaaa gcctggctcc cacggaaaat atgctcagtg cagccgcgtg | 1080 | |
| catgaatgaa aacgccgccg ggcgcttcta gtcggacaaa atgcagccga gaactccgct | 1140 | |
| cgttctgtgc gttctcctgt cccag | 1165 | |

<210> SEQ ID NO 6
<211> LENGTH: 1165
<212> TYPE: DNA
<213> ORGANISM: Homo sapiens

<400> SEQUENCE: 6

| | | |
|---|---|---|
| ttgttttggt tattaggaag ttttttattta aattagagta aatatattag aatttgggtt | 60 | |
| tgttatttta gtttgttgaa tttttttttt tggtttagat tttttatttt ggtttataaa | 120 | |
| ttttattgta taaatgtttt ttattgtaaa atattttaaa ttttttttaa gggaaggttg | 180 | |
| tatggaaatg atatagtaag gttttttttg tatttttttta gatttttatt agggaaggta | 240 | |
| gatttagatg tttttttttat ttttagtttt aaagttttttt atttataaaa ttttttaagt | 300 | |
| agtgattatt gttgttttga gtatttggag gtagtttaga gttttttgaaa ggtaatattt | 360 | |
| atatataaaa agaagttttt ttcgatttag attttagttt tggtgttaga tgtatatttg | 420 | |
| aggagtaggt ggttagttag attttttattt gagtagttaa taaaatttat tgttttttaa | 480 | |
| tggaatttttt tttgtaagtt cgaattgatt tgttattttt gtgatttgtg agatggtagg | 540 | |
| gaagtattaa atattattat gatttgggtt atagtggggg gaaaaaagga aaaagaaaa | 600 | |
| aaaaaattta ttgttaagtt ttgttaggcg tagaaagggt tggaattgtt ggggttatttt | 660 | |
| tatttgatttt attggaaata gagtggattt tattaatatt ttaataaaga gaatttttttt | 720 | |
| gtattaggtt ggaagtggtc gttagttttt cgtgtaatttt tatttttttgg aaaagtggaa | 780 | |
| ttagttggta ttgtttagcg tgatttgtga ggttgagttt taatagttta agaagtaaa | 840 | |
| tgggatgtta ttttcgcggg gttcgttttt cgcgaggtgt ttatttcgta ttttgttatgt | 900 | |
| aaaacgaggg agcgttagga aggaattcgt tttgtaaagt tattggttttt ggttattagt | 960 | |
| tttttattttaa tgttttcgtg atgttgttgt tgatttattt gggaagttgg ttggttggcg | 1020 | |
| aggtagagtt ttttttttaaa gtttggttttt tacggaaaat atgttagtg tagtcgcgtg | 1080 | |
| tatgaatgaa aacgtcgtcg ggcgttttta gtcggataaa atgtagtcga gaatttcgtt | 1140 | |
| cgttttgtgc gtttttttgt tttag | 1165 | |

<210> SEQ ID NO 7
<211> LENGTH: 1513
<212> TYPE: DNA
<213> ORGANISM: Homo sapiens

<400> SEQUENCE: 7

```
atggagcccg ctctcccctt cccggacgcc gctgcccggc cgatgctccc ggcaacccac    60
ccgcggcgta tgcagaggag cctttctctt tctctcagac cacttgtccc gaccaatctg   120
accttccaaa cacatctgac cgcacctccc aggtggacac actaataggc tacgggctgg   180
agaggagcgg gtgatgagga gagggattca aacctgcgaa cgcttgggct gggtcggagc   240 tgcgggggc ctgggaggag agaggggaga agagagaagg aaggagagcg cctgccggga    300
tggctgagct gcctcggcga gcagccttgg ggttgcacgc tcttgtggga gatgctgctg   360
ttgcttccag gtcggcaaga gcggttctaa caccatcgcc tctcaccctc tttcctgtaa   420
atccctagag aaacgtccct ggcctctccg ccgcgacatt cccagcctgc atcccctac    480 agcctaggcg gcgcgctccc gcacgctgga gcgccggtcg ccagcaggac gccctctccc   540
gcgccgactc gccctctct gcctgctgc tgctgctcct ctgacaccc cgcccccacc     600 atctccagct cggagagacg ccacccagcc gcggcccgca ctcgcggccc ggggtcacgc   660
gcggaagagg ggcgctagtc cggacccgc cttcggtagg gggcgtcctg gagcggagag    720
tgaggcgaat ggtatatgag tgtgcgggta gcccacctg aagcccgagc ttctcatttg    780
agccatcccc gcctagcccc actcgggcca gcgcctggcg agcgagccca tctgtggctt   840
ccgcggccgc ctcctccttg catccttgca cctcctcgtc gaccctccc tcccgggacc    900 tgcatcctgc tccaccaatc agagcccgac tgcctcttcc cacgtgaccc cgggcgggct   960
gaggacctgc tgcttcccaa cgccagagg gatgcgggcg gcagagctcg agaggcggct   1020
gccgggctgc ggggcgcctt gactctccct ccaccctgcc tctcgggct ccactcgtct   1080 gccctgggac tcccgtctcc tcctgtcctc cggcttccca gagctccctc cttatggcag   1140
cagcttcccg cgtctccggc gcagcttctc agcggacgac cctctcgctc cggggctgag   1200
cccagtccct ggatgttgct gaaactctcg agatcatgcg cgggtttggc tgctgcttcc   1260
ccgccgggtg ccactgccac cgccgccgcc tctgctgccg ccgtccgcgg gatgctcagt   1320 agccccgctgc ccggccccg cgatcctgtg ttcctcggaa gccgtttgct gctgcagagt   1380
tgcacgaact agtcatggtg ctgtgggagt cccgcggca gtgcagcagc tggacacttt   1440
gcgagggctt ttgctggctg ctgctgctgc ccgtcatgct actcatcgta gcccgcccgg   1500
tgaagctcgc tgc                                                     1513
```

<210> SEQ ID NO 8
<211> LENGTH: 1565
<212> TYPE: DNA
<213> ORGANISM: Homo sapiens

<400> SEQUENCE: 8

```
atggagttcg tttttttttt ttcggacgtc gttgttcggt cgatgttttc ggtaatttat    60
tcgcggcgta tgtagaggag tttttttttt tttttagat tatttgtttc gattaatttg   120
attttttaaa tatatttgat cgtatttttt aggtggatat attaataggt tacgggttgg   180
agaggagcgg gtgatgagga gagggattta aatttgcgaa cgtttgggtt gggtcggagt   240 tgcgggggt ttgggaggag agaggggaga agagagaagg aaggagagcg tttgtcggga    300
tggttgagtt gtttcggcga gtagttttgg ggttgtacgt ttttgtggga gatgttgttg   360 ttgttttag gtcggtaaga gcggttttaa tattatcgtt tttatttttt tttttgtaa    420 atttttagag aaacgtttt ggttttttcg tcgcgatatt tttagtttgt atttttttat    480
agtttaggcg gcgcgttttc gtacgttgga gcgtcggtcg ttagtaggac gtttttttc    540
```

```
gcgtcgattc gttttttttt gttttgttgt tgttgttttt ttgatatttt cgttttattt   600
atttttagtt cggagagacg ttatttagtc gcggttcgta ttcgcggttc ggggttacgc   660
gcggaagagg ggcgttagtt cggatttcgt tttcggtagg gggcgttttg gagcggagag   720
tgaggcgaat ggtatatgag tgtgcgggta gtttattttg aagttcgagt ttttattg     780
agttattttc gtttagtttt attcgggtta gcgtttggcg agcgagttta tttgtggttt   840
tcgcggtcgt ttttttttg tattttttgta tttttcgtc gattttttt tttcgggatt    900
tgtattttgt tttattaatt agagttcgat tgttttttt tacgtgattt cgggcgggtt    960
gaggatttgt tgttttttaa acgttagagg gatgcgggcg gtagagttcg agaggcggtt  1020
gtcgggttgc ggggcgtttt gatttttttt ttattttgtt ttttcgggtt ttattcgttt  1080
gtttttggat tttcgttttt ttttgttttt cggtttttta gagttttttt tttatggtag  1140
tagtttttcg cgttttcggc gtagttttt agcggacgat ttttcgttt cggggttgag    1200
tttagttttt ggatgttgtt gaaattttcg agattatgcg cgggtttggt tgttgttttt  1260
tcgtcgggtg ttattgttat cgtcgtcgtt tttgttgtcg tcgttcgcgg gatgtttagt  1320
agttcgttgt tcggttttcg cgattttgtg ttttcggaa gtcgtttgtt gttgtagagt   1380
tgtacgaatt agttatggtg ttgtgggagt tttcgcggta gtgtagtagt tggatatttt  1440
gcgagggttt tgttggttg ttgttgttgt tcgttatgtt atttatcgta gttcgttcgg   1500
tgaagttcgt tgttttttt attttttaa gtgattgtta aacgtttatc ggttggaatt    1560
gtttt                                                              1565
```

<210> SEQ ID NO 9
<211> LENGTH: 1189
<212> TYPE: DNA
<213> ORGANISM: Homo sapiens
<400> SEQUENCE: 9

```
cttgccggca agtagaaaac aaagcccagc ccagcttttc tctccagaga atgttgtggt    60
gggagaggga aagaaggtg gaggtcccgg aggaattgca catggggcca aaatgtgact   120
atgaaagaag agtgggcttt tgataatacc attaagaaaa tcacgcaaga aagaaaaaaa   180
gatggttagg aattacccct atgtggcagc atctgccctg cagaatgaga aggtttgcaa   240
atagacttcc caaaccccaa ccacagctcg ctccgcctcg aggacccctt ttctgcaccc   300
ccacctcagc gccctcttcc tgcacccaca aagagagtac tcagtcatag gggttcaaca   360
ggagagagga gacagaaggt acaggcggtg agcaggact cagccatcat cccctcagg    420
tccctcccca cccagttgac agagcgaatc ccgagtaatt gttttccgag ggggtccgtg   480
cgcgctcggt ggcgccgcct cggtctgggt tcccccgagg aaaaatacc acccgcgagg    540
gctcggcggc ttttcgactc ggcggggatg aactgtggca acttcggcag cccccaccgc   600
ggtgcggaag taaagagggc aacattggcg actgcggctc ggaggggctg gagcgcgtga   660
agccgtgggg gcgccgtgcg cctcccgctc tctcgtttcg gccgcaggtc ctgggactcc   720
gacttcggtg ctccgggtga tagcggctgc ggcgcctgca gtccagatcc tcgcagttct   780
gcgggcgaag gaggcgaacg gaatcggccc ccagtgggga gcgcaacaag ccacagtagc   840
caaaccccgc gctcctgccc gggctcccag acgaacgcag ccgcagcggg gggccgggcc   900
ccgagcccca cgccgccgcc gccgcgccag cggtggggg cgggctgggg gcggggcggc   960
cggggctgcc ttcccgggcg catatgcgag cgcagcaccc ggcgctgccg agccacctcc  1020
cccgccgccc gctagcaagt ttggcggctc caagccaggc gcgcctcagg atccaggctc  1080
```

| | |
|---|---|
| atttgcttcc acctagcttc ggtgccccct gctaggcggg gaccctcgag agcgatgccg | 1140 |
| atggatttga ttttagttgt gtggttctgt gtgtgcactg ccaggacag | 1189 |

<210> SEQ ID NO 10
<211> LENGTH: 1189
<212> TYPE: DNA
<213> ORGANISM: Homo sapiens

<400> SEQUENCE: 10

| | |
|---|---|
| tttgtcggta agtagaaaat aaagtttagt ttagttttt tttttagaga atgttgtggt | 60 |
| gggagaggga aagaaggtg gaggtttcgg aggaattgta tatgggtta aaatgtgatt | 120 |
| atgaaagaag agtgggtttt tgataatatt attaagaaaa ttacgtaaga aagaaaaaaa | 180 |
| gatggttagg aattattttt atgtggtagt atttgttttg tagaatgaga aggtttgtaa | 240 |
| atagattttt taaattttaa ttatagttcg tttcgtttcg aggattttt ttttgtattt | 300 |
| ttattttagc gtttttttt tgtatttata aagagagtat ttagttatag ggtttaata | 360 |
| ggagagagga gatagaaggt ataggcggtg agtagggatt tagttattat ttttttagg | 420 |
| ttttttta tttagttgat agagcgaatt tcgagtaatt gttttcgag ggggttcgtg | 480 |
| cgcgttcggt ggcgtcgttt cggtttgggt ttttcgagg aaaatattt attcgcgagg | 540 |
| gttcggcggt ttttcgattc ggcggggatg aattgtggta atttcggtag tttttatcgc | 600 |
| ggtgcggaag taagagggt aatattggcg attgcggttc ggaggggttg gagcgcgtga | 660 |
| agtcgtgggg gcgtcgtgcg tttttcgttt tttcgttttcg gtcgtaggtt ttgggatttc | 720 |
| gatttcggtg tttcgggtga tagcggttgc ggcgtttgta gtttagattt tcgtagtttt | 780 |
| gcgggcgaag gaggcgaacg gaatcggttt ttagtgggga gcgtaataag ttatagtagt | 840 |
| taaatttcgc gtttttgttc gggttttag acgaacgtag tcgtagcggg gggtcgggtt | 900 |
| tcgagtttta cgtcgtcgtc gtcgcgttag cggtggggg cgggtgggg gcggggcggt | 960 |
| cggggttgtt ttttcgggcg tatatgcgag cgtagtattc ggcgttgtcg agttattttt | 1020 |
| ttcgtcgttc gttagtaagt ttggcggttt taagttaggc gcgttttagg atttaggttt | 1080 |
| atttgtttt atttagtttc ggtgtttttt gttaggcggg gattttcgag agcgatgtcg | 1140 |
| atggatttga ttttagttgt gtggttttgt gtgtgtattg ttaggatag | 1189 |

<210> SEQ ID NO 11
<211> LENGTH: 1693
<212> TYPE: DNA
<213> ORGANISM: Homo sapiens

<400> SEQUENCE: 11

| | |
|---|---|
| gcagccggag cgcacgggcc caagaagaag tggggttgga cccgcagagg ccactttcca | 60 |
| cccgcatgga gaaagaaaat tctctcctct gaaagcgagg gcccttagct ttgcagccac | 120 |
| tgctgttttt cttttgccac cgacgcgcgt accgttcac gatgcaggac cgtggttaca | 180 |
| tgcgtaaagg aaaaaaagaa aaacgcattt tgcaggcctc gtcgtgtttt tcaaagagcc | 240 |
| acaggccgcc acaacgaaga acgacgccgc gaggcctgca agatcctgaa acttgttttg | 300 |
| aggggagagc agagaggaaa ggggttgttg gccccaggct acttagggtc cctaggagac | 360 |
| tcccttccgc ctgtccccgg tttggcacag gggccaccga ggctgggacc aaagccgcgc | 420 |
| agggctggga gcagcaaagg ccgccggccg ggcgtgacg acgcgcaaaa tcccgtgtgg | 480 |
| ggtggaggct cttgggtcag aataatgtgc gggacgaggg aggtgagtaa cctctttggg | 540 |

```
gcggctccca gtgcggcgtc accggccctg agaccccgcg gccccagcc cggggttgca      600
gaagtcacag gcccgaagca gcaagagctg gggaagcccg gccgcggcca gcggggagga      660
ggagcgaagg ggttgcgccc cagcgtcagg gagctacgac ccgagagagg gcggcaaggg      720
cgccttccgt gggaccccgga cgttctaagc aaatttctag catttgcccc gggctcccag     780
agctctcggg ggccctgggc tgtggcactg gggcctcctc cgcggggtgg cgccttccgc      840
ccctccccgt tgggcggcct ccggcaggcc ccgttcctcc ccgcgaacgc caccgaggtg      900
cccgcgatgg gggctccgcc gattggctgt gcgacgcgtc gctccgccag ccccgccccg      960
cggggccccg gggtactaac cccgcgcggg cggccgcggc cccgccactt gattctggag     1020
gatttgttct ggggctgcgg ccgcggagtc ggggcggccg cggggcgagct tcggggcggg    1080
aggcggcggc agcggcacag ccccgcgcgg gccccgccgc ggcccaggca gccgggacag     1140
ccacgagggg cggccgcacg cggggccgcg cgccgaggat gcgggactag ccgggcaggc     1200
tgcgggcggc cgtcgggcca gcgaggcctc gcagcgggcg ggccctggcg agtagtggcc     1260
gggcgccgcc ccctgcgccc tgaggcccgg gccccgccgc ttctgctttc ccgcttctcg     1320
cggcagcggc ggccgaggag gcgcccgcgc cggccgcccc cggggaagc cgcgccgtct      1380
ccgcctgccc ggcgccctga cggccgctgt tatgcgtatt cccgtagacc caagcaccag     1440
ccgccgcttc acacctccct ccccggcctt ccctgcggc ggcggcggcg gcaagatggg      1500
cgagaacagc ggcgcgctga gcgcgcaggc ggccgtgggg cccggagggc gcgcccggcc     1560
cgaggtgcgc tcgatggtgg acgtgctggc ggaccacgca ggcgagctcg tgcgcaccga     1620
cagccccaac ttcctctgct ccgtgctgcc ctcgcactgg cgctgcaaca agacgctgcc     1680
cgtcgccttc aag                                                       1693

<210> SEQ ID NO 12
<211> LENGTH: 1692
<212> TYPE: DNA
<213> ORGANISM: Homo sapiens

<400> SEQUENCE: 12
gtagtcggag cgtacgggtt taagaagaag tggggttgga ttcgtagagg ttatttttta      60
ttcgtatgga gaaagaaaat ttttttttt gaaagcgagg gtttttagtt ttgtagttat      120
tgttgttttt tttttgttat cgacgcgcgt atcgttttac gatgtaggat cgtggttata      180
tgcgtaaagg aaaaaaagaa aaacgtattt tgtaggtttc gtcgtgtttt ttaaagagtt      240
ataggtcgtt ataacgaaga acgacgtcgc gaggtttgta agattttgaa atttgttttg     300
aggggagagt agagaggaaa ggggttgttg gttttaggtt atttagggtt tttaggagat     360
ttttttttcgt ttgttttcgg tttggtatag gggttatcga ggttgggatt aaagtcgcgt    420
aggggttggga gtagtaaagg tcgtcggtcg ggcgtggacg acgcgtaaaa tttcgtgtgg    480
ggtgagggtt tttgggttag aataatgtgc gggacgaggg aggtgagtaa ttttttttggg   540
gcggttttta gtgcggcgtt atcggttttg agatttcgcg gttttttagtt cggggttgta    600
gaagttatag gttcgaagta gtaagagttg gggaagttcg gtcgcggtta gcgggagga     660
ggagcgaagg ggttgcgttt tagcgttagg gagttacgat tcgagagagg gcggtaaggg    720
cgttttttcgt gggattcgga cgtttttaagt aaatttttag tatttgtttc gggttttttag  780
agttttcggg ggtttttgggt tgtggtattg gggttttttt cgcggggtgg cgttttttcgt   840
tttttttcgt tgggcggttt tcggtaggtt tcgttttttt tcgcgaacgt tatcgaggtg     900
ttcgcgatgg gggtttcgtc gattggttgt gcgacgcgtc gtttcgttag tttcgtttcg     960
```

```
cgggtttcgg gggtattaat ttcgcgcggg cggtcgcggt ttcgttattt gattttggag    1020
gatttgtttt ggggttgcgg tcgcggagtc ggggcggtcg cgggcgagtt tcggggcggg    1080
aggcggcggt agcggtatag tttcgcgcgg gtttcgtcgc ggtttaggta gtcgggatag    1140
ttacgagggg cggtcgtacg cggggtcgcg cgtcgaggat gcgggattag tcgggtaggt    1200
tgcgggcggt cgtcgggtta gcgaggtttc gtagcgggcg ggttttggcg agtagtggtc    1260
gggcgtcgtt ttttgcgttt tgaggttcgg gtttcgtcgt ttttgttttt tcgttttcg     1320 cggtagcggc ggtcgaggag gcgttcgcgt cggtcgtttt cggggaagt cgcgtcgttt     1380 tcgtttgttc ggcgttttga cggtcgttgt tatgcgtatt ttcgtagatt taagtattag    1440
tcgtcgtttt atattttttt tttcggtttt ttttgcggc ggcggcggcg gtaagatggg     1500
cgagaatagc ggcgcgttga gcgcgtaggc ggtcgtgggg ttcggagggc gcgttcggtt    1560
cgaggtgcgt tcgatggtgg acgtgttggc ggattacgta ggcgagttcg tgcgtatcga    1620
tagttttaat tttttttgtt tcgtgttgtt ttcgtattgg cgttgtaata agacgttgtt    1680
cgtcgttttt aa                                                        1692

<210> SEQ ID NO 13
<211> LENGTH: 1260
<212> TYPE: DNA
<213> ORGANISM: Homo sapiens

<400> SEQUENCE: 13
gttatatatg ttttgggagt ttttagattt tatatgttta aattgggtt ttttgatata      60 aaattatgtt tatcggttag gaatttgtta gaaaatttag agtttagtag aaggaatatt    120
ggttttggaa tgtggaggtt tggttttgtt taaagtgtgt agtatgtgaa ggagaataat    180
ttattgatta ttattttgtt ttattgattt aaattttgag gttattgaa taattttta     240 gattgttttt tagttttaaa tttttttagta ttaaaatgaa gttattttta attttttttt    300
tttttttttt ttttcgtata tatatatata tttatatata tatatggtta aatagaaaag    360
gtaggtagat tagaagtttt agttgttgag aaagagggag ggagggtgag ttagaggtat    420
tttttttttt attgtagaga aaagtgaagt tttttagag tttcgttata ttttaaggt     480 tttttatgag ataatggagg aaataaagag ggtttagttt ttttattgtt tatatttat    540 ttttaaattt gttattagag gaatgatttt gattttatt tattatatat atgttttgtt    600
gtttgttggg ttttttaaa atgttagagt atgatgatag atggagttgt ttgggtatat    660
ttgtgtgtat ttaagggtga tagtgtattt gtttttaag agttgagtgt ttgagttttt    720
gtttgtgtgt aattgagtgt gtatgtgtgg gagtgaaatt gtggaatgtg tatgtttata   780
gtattgagtg aaaataaaag attgtataaa tcgtggggta tgtggaattg tgtgtgtttg    840
tgcgtgtgta gtatttttt ttttttaagt aagttatttt agattttgtt atttttttg     900 tttttgtga ttgattttgc gaggttaatg gtgcgtaaaa gggttggtga gatttggggg    960
cgttttttag tttgacgtta gagagagagt ttaaaataga gggagacggt tgagagtata   1020
taagtcgttt taggagcgag gttcggagtt atcgttgttg tttgttgatt cgcgtttaga   1080
gtttgattag ttatttttta gttcggtttt cgcggcgtcg agatgttgtt ttgtcgtttt   1140
tagtgcgcgt tggttgcgtt ttttatcgtt ttggttttgg gttgtgttat cggcgttttt   1200
tcggatttta gatttcgtta gttttgtag aagttttgg ttgttgtcgc ggggaagtag    1260

<210> SEQ ID NO 14
```

<211> LENGTH: 1260
<212> TYPE: DNA
<213> ORGANISM: Homo sapiens

<400> SEQUENCE: 14

```
gtcacatatg ttctgggagt tcctagacct tatatgtcta aactggggct tcctgacata      60
aaactatgct taccggccag gaatctgtta gaaaactcag agctcagtag aaggaacact     120
ggctttggaa tgtggaggtc tggttttgct caaagtgtgc agtatgtgaa ggagaacaat     180
ttactgacca ttactctgcc ttactgattc aaattctgag gtttattgaa taatttctta     240
gattgccttc cagctctaaa tttctcagca ccaaaatgaa gtccatttca atctctctct     300
ctctctttcc ctcccgtaca tatacacaca ctcatacata tatatggtca caatagaaag     360
gcaggtagat cagaagtctc agttgctgag aaagagggag ggagggtgag ccagaggtac     420
cttctccccc attgtagaga aaagtgaagt tcttttagag ccccgttaca tcttcaaggc     480
tttttatgag ataatggagg aaataaagag ggctcagtcc ttctactgtc catatttcat     540
tctcaaatct gttattagag gaatgattct gatctccacc taccatacac atgccctgtt     600
gcttgttggg ccttcctaaa atgttagagt atgatgacag atggagttgt ctgggtacat     660
ttgtgtgcat ttaagggtga tagtgtattt gctctttaag agctgagtgt ttgagcctct     720
gtttgtgtgt aattgagtgt gcatgtgtgg gagtgaaatt gtggaatgtg tatgctcata     780
gcactgagtg aaaataaaag attgtataaa tcgtggggca tgtggaattg tgtgtgcctg     840
tgcgtgtgca gtattttttt ttttttaagt aagccacttt agatcttgtc acctcccctg     900
tcttctgtga ttgattttgc gaggctaatg gtgcgtaaaa gggctggtga gatctggggg     960
cgcctcctag cctgacgtca gagagagagt ttaaaacaga gggagacggt tgagagcaca    1020
caagccgctt taggagcgag gttcggagcc atcgctgctg cctgctgatc cgcgcctaga    1080
gtttgaccag ccactctcca gctcggcttt cgcggcgccg agatgctgtc ctgccgcctc    1140
cagtgcgcgc tggctgcgct gtccatcgtc ctggccctgg gctgtgtcac cggcgctccc    1200
tcggacccca gactccgtca gtttctgcag aagtccctgg ctgctgccgc ggggaagcag    1260
```

<210> SEQ ID NO 15
<211> LENGTH: 1237
<212> TYPE: DNA
<213> ORGANISM: Homo sapiens

<400> SEQUENCE: 15

```
atattaaaaa attataatta attgaaaaat ataatatttt atatgtaaag gggagaaaat      60
tatttttatta aagatgttat attttttaat ttatttggag attaaagaaa tgtgtttgtt     120
aggtaattaa gggtttatgg aaaggtgtgg tttttgtata aatgttattt gtttaatatt     180
ttgtgttgtt aatgattgtt ttattagtat ttttattata tttatttttta tagaaaggag     240
aaatatgatt tatagagttt tttagtgata agggtgagga tttatatat  tatgttgttg     300
gttttttagt ttttagtaag aaagtgtagg agagaagtaa aaaacgtttt gtttaatttt     360
tgttttttgga tgtggtaagg aagaggagtt attcggtttg aaataaaaga aattttaagt     420
ttgatatata atgttatgtt taaattttt  tttttttaaa atgtaaaata aatttgtttt     480
tatttttttaa aatattatgg gattaaatat ttttttgtta tgttaaggaa aagttagtat     540
tcgcgttgat ttagaagagg gatgttttgg ttatagaacg atgttgtgtt ttagaaatat     600
ttaaatatta ttaagttaga aatagaaggg aaaataatgt ttttcgtat  tttttttaa      660
gtgtagtttt tttttttag tttgattttc gacgaaatgt ttgaatgttt atagttattt     720
```

```
ggttattttg aaaagtgtaa tttattttga cgtttcgagg gacgaaaaag ttatcgaagt      780
ttaaggaatg agttattttg tttaaatttg atgagtaata ttaggtgtta tgaaatttag      840
tttcgaagga gaggggaggg ggcgttagat ttgtagacgg aagtaggtcg tttcggattg      900
gatggcgaga tttcgatttt tttaaaattg cgttatttag aatttaattg ggtttagatg      960
ttatgggtat cgacgagtta tcgtttcgga aattttttaat tacgtaagcg aaaggagagg     1020
aggcggttaa ttaaatattg agtagaaagt cgcgtgggga gaatgttacg tgggtttgga     1080
ggtttaagga ggttgggata aatatcgtaa ggtattgagt aggcgaaaga gcgcgttcgg     1140 atttttttt cggcggtagt tatcgagagt gcggagcgat tagcgtgcgt tcggaggaat     1200
tagagaaatt tagtatttcg cgggattgtt cgtcgta                             1237
```

<210> SEQ ID NO 16
<211> LENGTH: 1237
<212> TYPE: DNA
<213> ORGANISM: Homo sapiens

<400> SEQUENCE: 16

```
atactaaaaa atcataatta attgaaaaat ataatacttc atatgtaaag gggagaaaac       60
tactccacca aagatgtcac atcttttaat tcatttggag atcaaagaaa tgtgtctgcc      120
aggcaaccaa gggctcatgg aaaggtgtgg tttctgtaca aatgctattt gtctaatatt      180
ttgtgctgtt aatgactgtc ccattagcat cttcactaca cttactttca tagaaaggag      240
aaacatgatt tatagagccc tttagtgaca agggtgagga tcctacacac tatgttgctg      300
gtttcctagt cttcagcaag aaagtgtagg agagaagcaa aaaacgtcct gttcaacccc      360
tgctcctgga tgtggcaagg aagaggagtt acccggcttg aaacaaaaga atcctaagt      420 ctgacacaca atgtcatgtt taaattcccc tttctccaaa atgtaaaata aatctgcttc      480
catcttctaa aatactatgg gactaaacat ccttttgtta tgctaaggaa aagccagtat      540
tcgcgttgat ttagaagagg gatgttctgg ttatagaacg atgctgtgtc tcagaaacac      600
ttaaatacta ttaagctaga aatagaaggg aaaataatgc ttccccgcat ctcccctcaa      660
gtgtagtcct ctttttttag cctgatttcc gacgaaatgt ctgaatgcct acagttattt      720
ggccatcctg aaaagtgcaa cttatcctga cgtctcgagg gacggaaaag ttaccgaagt      780
ccaaggaatg agtcactttg ctcaaatttg atgagtaata tcaggtgtca tgaaacccag      840
tttcgaagga gaggggaggg ggcgtcagat ctgcagacgg aagcaggccg ctccggattg      900
gatggcgaga cctcgatttt cctaaaattg cgtcatttag aacccaattg ggtccagatg      960
ttatgggcat cgacgagtta ccgtctcgga aactctcaat cacgcaagcg aaaggagagg     1020
aggcggctaa ttaaatattg agcagaaagt cgcgtgggga gaatgtcacg tgggtctgga     1080
ggctcaagga ggctgggata aataccgcaa ggcactgagc aggcgaaaga gcgcgctcgg     1140
acctccttcc cggcggcagc taccgagagt gcggagcgac cagcgtgcgc tcggaggaac     1200
cagagaaact cagcaccccg cgggactgtc cgtcgca                             1237
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

-continued tttgggaagt tggttggttg gc                                    22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actaaaaacg cccgacgacg                                       20

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tatgtttagt gtagtcgcgt gtatgaatga a                          31

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgttggcaa ggtagtcgat agtg                                  24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgctccctg tgttctcatt g                                     21

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ccagaaaggt ccaagttccg gctcact                               27

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
gttatcgtcg tcgttttttgt tgtc                                          24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggaattttc ggttgattgg tt                                             22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gggttttggc gagtagtggt c                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttgggaagt tggttggttg gc                                             22

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcggttaat taaatattga gtagaaagtc gc                                  32

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 gggttttag acgaacgtag tcgtagc                                         27

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttttgttag aaacgggagg cgttc                                          25
```

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggggcgtttt ttagtttgac gt                                          22

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggtgatgga ggaggtttag taagt                                       25

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gacttccgaa aaacacaaaa tcg                                         23

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacaacgtcc gcacctcct                                              19

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgaccgacg cgaacg                                                 16

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
actaaaaacg cccgacgacg                                             20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
aaatccgaac gcgctctttc g                                        21

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ccaccgctaa cgcgacga                                            18

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gaaaccaaaa acgctacgac gcg                                      23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
aacaacgata actccgaacc tcg                                      23

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
aaccaataaa acctactcct cccttaa                                  27

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
ccgaacaacg aactactaaa catcccgcg                                29

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
acccgacccc gaaccgcg                                                   18

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cgttttgagg ttcgggtttc gtcgtt                                          26

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tatgtttagt gtagtcgcgt gtatgaatga a                                    31

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
agaatgttac gtgggtttgg aggtttaagg ag                                   32

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
acgacgtaaa actcgaaacc cgaccc                                          26

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tcgggtgggc ggttgtttgg att                                             23

<210> SEQ ID NO 48

```
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
aacgacttat atactctcaa ccgtctccct cta                                    33

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
accaccaccc aacacacaat aacaaacaca                                        30

<210> SEQ ID NO 50
<211> LENGTH: 601
<212> TYPE: DNA
<213> ORGANISM: Homo sapiens
<220> FEATURE:
<223> OTHER INFORMATION: Pro H2AFY_2

<400> SEQUENCE: 50
gcggtaaacc aatttaggaa gacgtggcgg gctttgtggc ggctcctcct ctttcggcct        60
gtccgcagtt tttaaaaaac gtgtgtgatg ataaggaatc actgtctaca ttagtaattc      120
ccaacttggg tccgaaagtg aactttttgct gaagcgaagt agctaaccgc ttccatgtgc     180
aaggcaggtt ccagacttcg gggtgaggag gattaactga aggaccccag ggaaccggg       240 tgcgcagtaa ttgatcttgg ggcagaccag ggcttggcgg tggcctgtat ctaaagacag      300
cggggtctct gaggcgggggc aggggggagt tggcattgac tggggaggga agagcgatcg    360
ctggtaacag ccattgtgcc ttcccactgg gttagtggga aggttcctaa agatgccgtg      420
gcagcgacag tcccgtgctc agagccaggc acacagtagg cgttcactcg agacgcagag     480
tctgggacgc gccctgaaga agctcctctc caggggcctg gcccttccca aggactgggc     540
tctgggcgtc cccggggtca tgggtcagac ctcgcgtccg gggtgcgggc tggtgcctgg     600
g                                                                      601

<210> SEQ ID NO 51
<211> LENGTH: 601
<212> TYPE: DNA
<213> ORGANISM: Homo sapiens
<220> FEATURE:
<223> OTHER INFORMATION: Pro RND2-VAT1

<400> SEQUENCE: 51
tgcgggggtg ggaggagggg ccggggggggc gcggccgcct ggctggggc ggggcggagg       60 gggggccgcg gacccggggc gggggctcgg cgcgggcccg cgagatgccg gtgttggcgg      120
cccgagcggc tgcagttgca ggggcggggg aggcggcggc ggggcccggg agaggggtgg      180
cgtgggggac cggcgcgtag ccgggaccat ggaggggcag agcggccgct gcaagatcgt      240
ggtggtggga gacgcagagt gcggcaagac ggcgctgctg caggtgttcg ccaaggacgc      300
ctatcccggg gtgagggacc tgcgtcttgg gagggggacg ctaaggctgc tgggggtgg      360 gtgacagggg ccctggcgac ggatgggaat gggtactcgg gtaaccaggg acaagagaca     420
```

```
ggggtcgga ggacgcgggg aggccttgag ggctcaggaa ggactgcaga ggattggggt    480
gggaggaatt agggagcagg gtgagataga tggggtttgg gagaaccaga gcatccggga    540
gggagggcga ggggaatgtc ggaggtcctg ggcaatggag aggggaagaa ctaggggct     600 g                                                                    601
```

<210> SEQ ID NO 52
<211> LENGTH: 601
<212> TYPE: DNA
<213> ORGANISM: Homo sapiens
<220> FEATURE:
<223> OTHER INFORMATION: Pro RND2

<400> SEQUENCE: 52

```
tgcggggtg ggaggagggg ccggggggc gcggccgcct ggctgggggc ggggcggagg     60 ggggccgcg gacccggggc gggggctcgg cgcgggcccg cgagatgccg gtgttggcgg    120
cccgagcggc tgcagttgca ggggcgggg aggcggcggc ggggcccggg agaggggtgg    180
cgtgggggac cggcgcgtag ccgggaccat ggaggggcag agcggccgct gcaagatcgt    240
ggtggtggga gacgcagagt gcggcaagac ggcgctgctg caggtgttcg ccaaggacgc    300
ctatcccggg gtgagggacc tgcgtcttgg gaggggggacg ctaaggctgc tggggggtgg    360
gtgacagggg ccctggcgac ggatgggaat gggtactcgg gtaaccaggg acaagagaca    420 ggggggtcgga ggacgcgggg aggccttgag ggctcaggaa ggactgcaga ggattggggt    480
gggaggaatt agggagcagg gtgagataga tggggtttgg gagaaccaga gcatccggga    540
gggagggcga ggggaatgtc ggaggtcctg ggcaatggag aggggaagaa ctaggggct     600 g                                                                    601
```

<210> SEQ ID NO 53
<211> LENGTH: 601
<212> TYPE: DNA
<213> ORGANISM: Homo sapiens
<220> FEATURE:
<223> OTHER INFORMATION: Pro WT1-WIT1_2

<400> SEQUENCE: 53

```
gtacgacccc aacggatcca catgcccgga agcccaggcg acactaagcc agcgctgggg    60
aactgacgta ctcctgcagt cgcagggcgc tccatgcctc tctgtcctct tctttgttgt    120
gggtaacgtt ctctgcggga gacctgaggt tttccaaggg ggacatgcca gctacactgg    180
ccttggcgcc ctgagctaag caccaggact cacagcctag cacgaaggca ggtagcacct    240
tcacccgccg cggacgatag gcgctctcct gtacctcctt tagctcgcga ggcccgccct    300
tcgcgaggtc ccagagaaaa gcaggctgtg gaaaactggg cgccccttc tttcacccac    360 cttcttaccc ctgtcagcgc cgagatctgt agcagaggtt cctggtctga accaccgatt    420
ggcaaagaaa gctgcagatt aaacttctcg ttttacagag aaggaaactg aggcccagac    480
agccgaagga gaggcagtct atggagcgca gcggtaaaga gcaagggtt ggtggcccca    540 gaatggaacc tcagctctgc caggtaacca acagctgtgt gaccctagac gagttccgca    600
g                                                                    601
```

<210> SEQ ID NO 54
<211> LENGTH: 601
<212> TYPE: DNA
<213> ORGANISM: Homo sapiens
<220> FEATURE:

<223> OTHER INFORMATION: Pro WT1-WIT1_1

<400> SEQUENCE: 54

```
gcttgggctg ctgagtgaat ggagcggccg agcctcctgg ctcctcctct tccccgcgcc    60
gccggcccct cttatttgag cttttgggaag ctgagggcag ccaggcagct ggggtaagga   120
gttcaaggca gcgcccacac ccgggggctc tccgcaaccc gaccgcctgt ccgctccccc   180
acttcccgcc ctccctccca cctactcatt caccaccca cccacccaga gccgggacgg    240
cagcccaggc gcccgggccc cgccgtctcc tcgccgcgat cctggacttc ctcttgctgc   300
aggacccggt ttccacgtgt gtcccggagc cggcgtctca gcacacgctc cgctccgggc   360
ctgggtgcct acagcagcca gagcagcagg gagtccggga cccgggcggc atctgggcca   420
agttaggcgc cgccgaggcc agcgctgaac gtctccaggg ccggaggagc cgcggggcgt   480
ccgggtctga gccgcagcaa atgggctccg acgtgcggga cctgaacgcg ctgctgcccg   540
ccgtcccctc cctgggtggc ggcggcggct gtgccctgcc tgtgagcggc gcggcgcagt   600
g                                                                   601
```

<210> SEQ ID NO 55
<211> LENGTH: 601
<212> TYPE: DNA
<213> ORGANISM: Homo sapiens
<220> FEATURE:
<223> OTHER INFORMATION: Pro WIT1_1

<400> SEQUENCE: 55

```
gtacgacccc aacggatcca catgcccgga agcccaggcg acactaagcc agcgctgggg    60
aactgacgta ctcctgcagt cgcagggcgc tccatgcctc tctgtcctct tctttgttgt   120
gggtaacgtt ctctgcggga gacctgaggt ttttccaaggg ggacatgcca gctacactgg   180
ccttggcgcc ctgagctaag caccaggact cacagcctag cacgaaggca ggtagcacct   240
tcacccgccg cggacgatag gcgctctcct gtacctcctt tagctcgcga ggcccgccct   300
tcgcgaggtc ccagagaaaa gcaggctgtg gaaaactggg cgcccccttc tttcacccac   360
cttcttaccc ctgtcagcgc cgagatctgt agcagaggtt cctggtctga accaccgatt   420
ggcaaagaaa gctgcagatt aaacttctcg ttttacagag aaggaaactg aggcccagac   480
agccgaagga gaggcagtct atggagcgca gcggtaaaga gcaagggtt ggtggcccca    540
gaatggaacc tcagctctgc caggtaacca acagctgtgt gaccctagac gagttccgca   600
g                                                                   601
```

<210> SEQ ID NO 56
<211> LENGTH: 601
<212> TYPE: DNA
<213> ORGANISM: Homo sapiens
<220> FEATURE:
<223> OTHER INFORMATION: Pro WIT1_2

<400> SEQUENCE: 56

```
agtagagaag agctacctgg gccttcgtct ggcaactggg atatgcagcc gctggtcagc    60
agagggatgt gtattcatta gcggtggaag acgaggaaag cgcccgggag tgaggaagag   120
gaatggacag aattcctggc agaagcttac caagacaaaa atcagacaca atgtttaagc   180
agcaattgct cgtgaagttc ataaccatgg ctctctgtaa atcttggcaa attgggacat   240
tctttgcttt ttggaaatga ttgttttcaa gactttttt aaaaaatcaa gttgtccacc   300
agaaaaatgg aatagctcac cttccccatc ttttttttaa agcagggata tcctcatcct   360
```

```
ttccgtgcca ttcattcttt cattcattca ctcaccgtgc aacaaagatt gttgggcatt      420
gtagcagcaa gtaggagcac agggtaatga caggctcacc ccgctctcac agtttatatt      480
ccagtaggta tgacagatac attacaagga acaatgaga tattttcata tagtagtaat      540
tgctataaaa gaacaaggag atctgtaaga ctagagaatg actaaaggtg agatgggaat      600
g                                                                     601
```

<210> SEQ ID NO 57
<211> LENGTH: 601
<212> TYPE: DNA
<213> ORGANISM: Homo sapiens
<220> FEATURE:
<223> OTHER INFORMATION: Pro CNTNAP5

<400> SEQUENCE: 57

```
cgcccaggct gctcttatag gcgagcgcgg ggcgggcctg gctgggggcg gtgccgcgcg       60
gccccgctcg cctataagga gctgtccgcc acccgggtgc tgattccagc tctcgcgccc      120
gacgaggtgg atttggctgt ccaccgagct ccggcgcctg tcgttctaat tgggtttgga      180
tttgcaccgt taaggagggg ggaagagaag gaagaggcgg gcgaggaagg cgagtccagc      240
tagcggctgt tgcggggacc gtagcccag ctgcagctcc gaagaatccc ccgccacggt       300
ttcggtggag cgtctgggca cgggatggag tgaaagagcg agtgcctctc caagcggggg      360
tgggaggggg tcaggctgtg cagaggagag agacagcgag aagaagccgc ggctggctac      420
tgcgaatttg ggattcgatt gggagggacc gctcactcgg gggaaatgga ttctttacca      480
cggctgacca gcgttttgac tttgctgttc tctggcttgt ggcatttagg attaacagcg      540
acaaactgtg agtacgagga gctgggggcg ggaaggtgag gtggaaaacg atcgcattca      600
g                                                                     601
```

<210> SEQ ID NO 58
<211> LENGTH: 601
<212> TYPE: DNA
<213> ORGANISM: Homo sapiens
<220> FEATURE:
<223> OTHER INFORMATION: Pro KCNG2

<400> SEQUENCE: 58

```
gggcggacgc gctcccccag ctcagccctc gcgaccctaa cgcggtccgt tccttttgca       60
ggagccgggc aggagcccct cggtccggtc cggccctgcg catggagcca tggccctgct      120 ccccgggcg cggcggcggg acccgcgcgcc ggcacgtcat catcaacgtg ggcggctgcc      180
gcgtgcgcct ggcatgggcc gcgctggcgc gatgccccct cgcgcgcctg gagcgcctgc      240
gcgcctgccg cggccacgac gacctgctgc gcgtgtgtga cgactacgac gtgagccgcg      300
acgagttctt cttcgaccgc agcccgtgcg ccttccgcgc catcgtggcg cttttgcgcg      360
cagggaagct gcgactgctg cggggcccgt gcgcgctggc cttccgcgac gagctggcct      420
actggggcat cgacgaggcg cgcctggagc gctgctgcct gcgccgcctg cgccgccgcg      480
aggaggaggc ggccgaggcc cgcgcgggcc cgacggagcg cggggcgcag gggagcccgg      540
cgcgcgccct gggacctcgg gggcggctgc agcgcggccg gcgcgcctg cgcgacgtgg       600 t                                                                     601
```

<210> SEQ ID NO 59
<211> LENGTH: 601
<212> TYPE: DNA

<213> ORGANISM: Homo sapiens
<220> FEATURE:
<223> OTHER INFORMATION: Pro ACTRT2

<400> SEQUENCE: 59

| | | | | | |
|---|---|---|---|---|---|
| gggggatggg | ggactcagag | ccccacccc | agggcctctg | aggctcagga | caatcgttgc | 60 |
| cttggctaga | ttgttaccta | ggagacaacc | ccctggcccc | ctggaagagg | cctcagcagg | 120 |
| cccaggccac | ctggagggag | agcagacctg | cggctgagga | tgcagggctc | ccgggcacgg | 180 |
| tgctagccct | gccttgagac | accccgagag | ctgtgggaag | agctgtggga | tccctattg | 240 |
| catcacaaag | cggccctgga | gggctggtct | ttattttgat | gaggctgaga | agggaaggct | 300 |
| gcgggcatgt | ttaatccgca | cgctttagac | tccccggctg | tgattttga | caatggctcg | 360 |
| gggttctgca | aagcgggcct | gtctgggag | tttggacccc | ggcacatggt | cagctccatc | 420 |
| gtggggcacc | tgaaattcca | ggctccctca | gcagaggcca | accagaagaa | gtactttgtg | 480 |
| ggggaggagg | ccctgtacaa | gcaggaggcc | ctgcagctgc | actcccctt | cgagcgtggc | 540 |
| ctgatcacag | ggtgggatga | cgtggagaga | ctctggaagc | acctctttga | gtgggagcta | 600 |
| g | | | | | | 601 |

<210> SEQ ID NO 60
<211> LENGTH: 601
<212> TYPE: DNA
<213> ORGANISM: Homo sapiens
<220> FEATURE:
<223> OTHER INFORMATION: Pro PHC2

<400> SEQUENCE: 60

| | | | | | |
|---|---|---|---|---|---|
| cgtgtccgcc | ccgcccctcc | cgcggccccg | ccctccccg | ccccgctccc | tcgcccgcc | 60 |
| cccggcggag | gcgccgcgg | gagccgtccc | agactcgccg | cattgtctcc | gcggcggctg | 120 |
| cagccctcga | gcgcccgccg | cgcgcgcg | cgcaacccg | gccgccgccc | gcgctcccgc | 180 |
| cccggcctcg | cgccccgtc | ccggcctcgc | gccccggcg | ccctttgttg | acgcggcca | 240 |
| ggccggtgcg | gtcggatgcg | ccgcggcagc | cccgggcccc | ggctcggagg | ctcccggcgg | 300 |
| agaggaggcg | gcccgcccgg | gcccgggacc | ccgcgcgagt | cggcgcccgg | ccgagggggct | 360 |
| gcgtaggccc | cgcccggcca | ggcccagccg | ggccctggac | aggtcagtgc | cggggcgggg | 420 |
| gaggggttct | cgccagtagg | gaggccgggg | gccgcgctcg | ccgcactgga | agtcgggcac | 480 |
| cgccctcggt | gccctaacg | gcccgggcct | acgcggctgc | caggccgtgc | cagtcgcggc | 540 |
| tctcgtccgc | gcggcgcctg | ggaggtgccc | tgctccccag | cctcgctcgc | ctggggaccc | 600 |
| t | | | | | | 601 |

<210> SEQ ID NO 61
<211> LENGTH: 601
<212> TYPE: DNA
<213> ORGANISM: Homo sapiens
<220> FEATURE:
<223> OTHER INFORMATION: Pro OTOP1

<400> SEQUENCE: 61

| | | | | | |
|---|---|---|---|---|---|
| gaatcggaag | ggagttgaaa | agggaggtgc | tggttggcag | aggcgtcggg | gcaaggacag | 60 |
| gagccaggag | cgcaggcggg | gcccgacggc | agccaccccc | gggaccagac | ttggcgcggg | 120 |
| tgtctcgaag | atgctcgagg | gctgggggtc | gcccgcctcg | cccgggcag | ctgcaagcgc | 180 |
| ctcggtcgca | gggtcgtcgg | ggccagcggc | ctgctcgcct | ccctcgtcct | cggccccgag | 240 |
| gtccccggaa | tccccggccc | ccggcgggg | cggtgtgcgc | gccagcgtcc | cacagaaact | 300 |

```
ggccgagatg ctgagcagcc agtatgggct gatcgtgttc gtggcggggc tgctgctgct    360
gctggcctgg gccgtgcacg ccgcgggcgt gagcaagagc gacctgctgt gcttcctgac    420
ggcgctcatg ctgctgcagc tgctgtggat gctgtggtac gtgggccgca gctccgcgca    480
ccgccgcctc ttccgcctca aggacacgca cgcgggtgcc ggctggctgc gcggtgagtc    540
caggcgccgg gcgagcgggt ctccgcctcc tcgcccgctg gctgcatcct gaggctgctc    600
t                                                                  601

<210> SEQ ID NO 62
<211> LENGTH: 601
<212> TYPE: DNA
<213> ORGANISM: Homo sapiens
<220> FEATURE:
<223> OTHER INFORMATION: Pro TUSC3

<400> SEQUENCE: 62
ctcctcagcg ctggtccggg aaaggcaagc tccgggcggg agcgcacgcc gcgcccccga     60
agcctggctc cctcgccacg cccacttcct gcccccatcc cgcgcctttc caggtcttct    120
cccggtgaac cggatgctct gtcagtctcc tcctctgcgt cctcggccgc ggcccgggtc    180
cctcgcaaag ccgctgccat cccggagggc ccagccagcg ggctcccgga ggctggccgg    240
gcaggcgtgg tgcgcggtag gagctgggcg cgcacggcta ccgcgcgtgg aggagacact    300
gccctgccgc gatgggggcc cggggcgctc cttcacgccg taggcaagcg gggcggcggc    360
tgcggtacct gcccaccggg agctttccct tccttctcct gctgctgctg ctctgcatcc    420
agctcggggg aggacagaag aaaaaggagg tagaatggat ccccttggcc ttcccctgtg    480
ggcgggggcg ggccagggtg ggccgcgttg ccaggcagcc ctgccgtgtt gctaggcagc    540
ctggtcgccg gcgtgggcga tgccggcgct ggggcgggag ccgcgagggt gggaggccct    600
g                                                                  601

<210> SEQ ID NO 63
<211> LENGTH: 601
<212> TYPE: DNA
<213> ORGANISM: Homo sapiens
<220> FEATURE:
<223> OTHER INFORMATION: Pro CEBPD_1

<400> SEQUENCE: 63
ggagagagcc tttaatgcgt tttaaaagcg acagaccctc tctcctgagt agctcgggcc     60
tgcgccccat ccccccgccc ccccacaca cacacctggc gcccgggctc cctggtgctc    120
gctggctgcg ggtccggaac gcaccctttcc cgagccgggt cctgcgccac cggcgggcgg    180
gcgggagtca ctgcgaatat aggaagcagg ggcgatttca aatgctgctt tattcttaca    240
aatactgtaa aaattaatat aaaaaagtga gcatgctcag tctttcctc ttatctacaa    300 tacaaagggt ttgtctgaaa agtctggttt tttttctttt tacaaatgta ccttagctgc    360
atcaacagga gtaagatgta gaaaaagcta ccattacaaa ataatttaa gggaaaataa    420 acacgtttag cttctctcgc agtttagtgg tggtaagtcc aggctgtagc ttctttgcgc    480
tcctatgtcc caagaaactg cagcgggcac ccggcggctc tggctgcgcc agggcaggge    540 gcgctccgct ccgggccgtc gggtctgagg tatgggtcgt tgctgagtct ctcccgcccc    600
g                                                                  601

<210> SEQ ID NO 64
```

<211> LENGTH: 601
<212> TYPE: DNA
<213> ORGANISM: Homo sapiens
<220> FEATURE:
<223> OTHER INFORMATION: Pro CEBPD_2

<400> SEQUENCE: 64

| | | | | | | |
|---|---|---|---|---|---|---|
| cccttccccc | gcggcccgg | ggcgccccg | cggtgccgga | gtcggggcgg | ggcgtgcacg | 60 |
| tcagccgggg | ctagaaaagg | cggcggggct | gggcccagcg | aggtgacagc | ctcgcttgga | 120 |
| cgcagagccc | ggcccgacgc | cgccatgagc | gccgcgctct | tcagcctgga | cggcccggcg | 180 |
| cgcggcgcgc | cctggcctgc | ggagcctgcg | cccttctacg | aaccgggccg | ggcgggcaag | 240 |
| ccgggccgcg | gggccgagcc | aggggcccta | ggcgagccag | gcgccgccgc | cccgccatg | 300 |
| tacgacgacg | agagcgccat | cgacttcagc | gcctacatcg | actccatggc | cgccgtgccc | 360 |
| accctggagc | tgtgccacga | cgagctcttc | gccgacctct | tcaacagcaa | tcacaaggcg | 420 |
| ggcggcgcgg | ggccctgga | gcttcttccc | ggcggccccg | cgcgcccctt | gggcccgggc | 480 |
| cctgccgctc | cccgcctgct | caagcgcgag | cccgactggg | gcgacggcga | cgcgcccggc | 540 |
| tcgctgttgc | ccgcgcaggt | ggccgcgtgc | gcacagaccg | tggtgagctt | ggcggccgca | 600 |
| g | | | | | | 601 |

<210> SEQ ID NO 65
<211> LENGTH: 601
<212> TYPE: DNA
<213> ORGANISM: Homo sapiens
<220> FEATURE:
<223> OTHER INFORMATION: Pro WDR5

<400> SEQUENCE: 65

| | | | | | | |
|---|---|---|---|---|---|---|
| gctgtcgctg | cccgtagcgc | tcctccgaga | ggccggcttt | gtgagctcgc | cccgccccc | 60 |
| ggacaccgcc | ccctcccctc | gcgcacgcgc | actgcgcccc | cgccgcctgg | cgcccgcccg | 120 |
| agctgccgcc | ttgtcgagct | gagtccgcgc | tcccgcccag | gcggcggccg | acgcgacgcc | 180 |
| ccgagcgccc | ggccccgccg | ccgcggcccg | gcaggtaagc | gggcagccgc | ccggcccggg | 240 |
| gaacacaagg | cgggcagcgg | ggcggcgcca | gaagcttcca | aaccgcaccc | ggccgccgca | 300 |
| cgtgttcccc | gccgggcctc | gggccaggcc | cagccccggg | cgctgctccc | gctgcagcgg | 360 |
| ccccgccccgg | gaccccgcc | ccggcccctc | ggtggacggc | cgcgcgcgca | gttccctcca | 420 |
| cccggtccgc | ccccactcgc | gcccccacct | ccgcctcccc | ggcggaccgc | tgacaaggcc | 480 |
| agagcgccgg | cactgggtcc | tctttccgc | aggcagcgtg | cccggcctca | catcgcccct | 540 |
| ctccctccac | tgcccttca | gggaaggacc | ccagacccac | caagccactc | agtccctgga | 600 |
| c | | | | | | 601 |

<210> SEQ ID NO 66
<211> LENGTH: 601
<212> TYPE: DNA
<213> ORGANISM: Homo sapiens
<220> FEATURE:
<223> OTHER INFORMATION: Pro CALML3

<400> SEQUENCE: 66

| | | | | | | |
|---|---|---|---|---|---|---|
| gtctaaacag | gacaggcccg | ggcaaccgca | gggcaggggc | gtctgccaat | gatgggggag | 60 |
| gactctgctg | cttcttaagc | tccagcgtct | caagccaggg | cgagacagcc | cgccggccgc | 120 |
| ccggatctcc | acctgccacc | ccagagctgg | gacagcagcc | gggctgcggc | actgggaggg | 180 |
| agaccccaca | gtggcctctt | ctgccacccca | cgcccccacc | cctggcatgg | ccgaccagct | 240 |

```
gactgaggag caggtcacag aattcaagga ggccttctcc ctgtttgaca aggatgggga    300
cggctgcatc accacccgcg agctgggcac ggtcatgcgg tccctgggcc agaaccccac    360
ggaggccgag ctgcgggaca tgatgagtga gatcgaccgg gacggcaacg gcaccgtgga    420
cttccccgag ttcctgggca tgatggccag gaagatgaag gacacggaca acgaggagga    480
gatccgcgag gccttccgcg tgttcgacaa ggacggcaac ggcttcgtca gcgccgccga    540
gctgcgacac gtcatgaccc ggctggggga gaagctgagt gacgaggagg tggacgagat    600
g                                                                   601
```

<210> SEQ ID NO 67
<211> LENGTH: 601
<212> TYPE: DNA
<213> ORGANISM: Homo sapiens
<220> FEATURE:
<223> OTHER INFORMATION: Pro CIDEA_1

<400> SEQUENCE: 67

```
agagcgcgaa gtcgcgatcc tcggcggtgg agagctcgtg ccaaaacgtc ctcccctgcg     60
ccagtcaggc cttcgcgggg ctggcaggcg ggcggggggcg gggccgccgc actttaagag   120
gctgtgcagg cagacagacc tccaggcccg ctaggggatc cgcgccatgg aggccgcccg   180
ggactatgca ggagccctca tcaggcgagt gccccgcgtc ccctgattg ccgtgcgctt    240 ccaatcgcct tgcgttcggt ggcctcatat tccctgtgc gcctctagta ccgtaccccg    300
ctcccttcag ccccctgctc cccgcattct cttgcgctcc gcgaccccgc gcacacaccc    360
atccgcccca ctggtgccca agccgtccag ccgcgcccgc gggcagagcc caatcccgtc    420
ccgcgcctcc tcaccctctt gcagctgggc acaggtacca ggtgtggctc ttgcgaggtg    480
cgcgggcgtc tgcaaaccag gtgacagctg gcgagtggct gcatgcatct ctggccgctg    540
ctgcagtcgc gggcgcagaa gagggtccgg tcccaggaac cccgagcaaa gcttccgcga    600
t                                                                   601
```

<210> SEQ ID NO 68
<211> LENGTH: 601
<212> TYPE: DNA
<213> ORGANISM: Homo sapiens
<220> FEATURE:
<223> OTHER INFORMATION: Pro CIDEA_2

<400> SEQUENCE: 68

```
cccctgctc cccgcattct cttgcgctcc gcgaccccgc gcacacaccc atccgcccca    60
ctggtgccca agccgtccag ccgcgcccgc gggcagagcc caatcccgtc ccgcgcctcc   120
tcaccctctt gcagctgggc acaggtacca ggtgtggctc ttgcgaggtg cgcgggcgtc   180
tgcaaaccag gtgacagctg gcgagtggct gcatgcatct ctggccgctg ctgcagtcgc   240
gggcgcagaa gagggtccgg tcccaggaac cccgagcaaa gcttccgcga tgcgagggga   300
ccgggcttct gggggtcctg gaaatcacaa cgggagctgg gcgcgggagg gcccaggct    360 tggccccctcc tggaagcgcg ggctctggtc tccgagggga ggccccaacc gtccggcgga   420
gccctccagg ttggtggtgc tgggagaagc gctcctcctt gcctcgggt ccaagggcgg    480 agacgctgcc tggggagcag ggggggacaag gggcgggtgg accctgagga gtcttccctg    540
cgcttcgcac ccgctcgtgg tcgaacaggc agcattggct attttcctgc ttgggttaat    600
a                                                                   601
```

<210> SEQ ID NO 69
<211> LENGTH: 601
<212> TYPE: DNA
<213> ORGANISM: Homo sapiens
<220> FEATURE:
<223> OTHER INFORMATION: Pro CAMK2N2

<400> SEQUENCE: 69

| | |
|---|---|
| gctcatcgtc attccgctct tgccgccgcc gccgccaccc ccgcccccg ccccgcccc | 60 |
| cgcccggtcc ccgccaccgc cgccgccgcc gcctgcccag cggcccggga ggcggaggcg | 120 |
| cgggggagga ggccccgctt ggctcctcag ccccggatgc tgcatgactt catccttccg | 180 |
| ccggctcccc tgctgaggta gggccggtcc ggcagcaagc ccgccgcccg cgccccgccc | 240 |
| cagtcccgct cccgcccgc gcccaccccg cgccgccat gtccgagatc ctgccctaca | 300 |
| gcgaagacaa gatgggccgc ttcggcgcag acccgaggg ctccgacctc tccttcagct | 360 |
| gccgcctgca ggacaccaac tccttcttcg cgggcaacca ggccaagcga ccccccaagc | 420 |
| tgggccagat cggccgagcc aagcgaggta cgcggcccgg gccggagtc gccgcctgac | 480 |
| ccagaaaccc tccgccgggc gccccccggc tgccgttccc cgccgagtgc ccgcagctct | 540 |
| tgccgcagac cagcgcacca gccgctctcc agcccgggct ggaggggggg gtccccgctg | 600 |
| c | 601 |

<210> SEQ ID NO 70
<211> LENGTH: 601
<212> TYPE: DNA
<213> ORGANISM: Homo sapiens
<220> FEATURE:
<223> OTHER INFORMATION: Pro STX1A

<400> SEQUENCE: 70

| | |
|---|---|
| gggtggggcg gggccgggt cccggggcc ggggcgggc cgggctggcg ctgcgcagcc | 60 |
| gcggggcggc cgtcgcgcat gcggggctca cacggctgca gccggcgccg ctgccactcc | 120 |
| cgggagcatg aaggaccgaa cccaggagct ccgcacggtg agtccggccc cagcgcgcgg | 180 |
| ccgcccgccg cccgccgcca gcgccaacgc gccggacact tcccgcccgg ctcccgcggc | 240 |
| caggatggtg gccgctcctg cgcccccagc cagggctgaa gggagcgggg cgagccaggg | 300 |
| acctcgaccc ccctccgggt tccgccctc ggaccactc ggggtcaggc tcgcgtgagc | 360 |
| tcggccgcgc tgacacgtgg acggtcggct ggagtccggg gtcctggata aacttttcgg | 420 |
| ggccctcttg atttggggg ttcggagggt atgatgggt tttggtggcg ggacctcttc | 480 |
| ccctccgc agagcaggcc ctttctctgg ccccctcact gcccctcatc tctgacctcc | 540 |
| cgtgcccct cggtgtagac agacgagggg accgcggtgg gaacctcctt ggtgtagaca | 600 |
| g | 601 |

<210> SEQ ID NO 71
<211> LENGTH: 601
<212> TYPE: DNA
<213> ORGANISM: Homo sapiens
<220> FEATURE:
<223> OTHER INFORMATION: Pro SMARCD3

<400> SEQUENCE: 71

| | |
|---|---|
| cggcggcggg cggcggcgg cggcgtgggc cgtgggccgt cagggcagcc ctgaagggc | 60 |
| cccctccca ctccgctcga gtagaagtgt gagagagccc agcaggactc agaggggaga | 120 |
| gttggaggaa aaaaaaggc agaaaaggga aagaaagagg aagagagaga gagagtgaga | 180 |

```
ggagccgctg agcccacccc gatggccgcg gacgaagttg ccggaggggc gcgcaaagcc      240
acgaaaagca aacttttttga gtttctggtc catggggtgg tgagtggggg aaagttagcg     300
ggggagggca agcgagctgg ctcgggctga atggagggct gatcgggagg ggccgggagg     360
gcgctcccgc tctcccaccc ctctagtggg gggcgtcatg gccacgcc cggccgcggg      420 actgtgctgg cgccctggca cccgaacacg tcgccaggcg gccggccggg tctgacgcga     480
ggcggggaag ggaggcgttt gcatggctct tgtcaggggc gggggtggga cttggggact    540 ctaccccccca agtagggggt cctcgctgta gccgacaggt tgactttcgt tcttttcctt    600
g                                                                      601

<210> SEQ ID NO 72
<211> LENGTH: 601
<212> TYPE: DNA
<213> ORGANISM: Homo sapiens
<220> FEATURE:
<223> OTHER INFORMATION: Pro LOC728489_1

<400> SEQUENCE: 72
ctgcgcacag acaaggctgg gagacaaacc ccacacacct cggagggccc tggggacgtc      60
cagagcgctg tccaccgagg gaaggaggcc caggtggctc ccccgggagg ggtctggagc     120
tcctaacaca cggccacgcc atagctgctc gtcctgcctg gccagcagg cagcctggtt     180 tgctcactgt ttcgccgacg gccggcggcc gaggaccagg gctcaggtct gcactggctc    240
acggaaggga ggccgccaga gctggccagg ggggcggcaa gggccttgca gaggaaggct    300
gaggctcaca ggggtggtga cctgctcaaa gtcacgcagc gacagccagg aagggctctg    360
acgccacatc cagccccctt tccacgcgac tgtggcctct gtgggcaaga gctgggtgac    420
tctgtgtaga aggaactgtg gtgaggcgag aggtcctgcg gctcctatgt cccacccagc    480
agcaccaggg attcagagca atcgttctaa ctccagaaaa agaaaggcca cgagggccac    540
aggccccagc atctggaagt aatgtctgtt tattgataga aaacaggcca cgtccagaga    600
g                                                                     601

<210> SEQ ID NO 73
<211> LENGTH: 601
<212> TYPE: DNA
<213> ORGANISM: Homo sapiens
<220> FEATURE:
<223> OTHER INFORMATION: Pro LOC728489_2

<400> SEQUENCE: 73
ggggtgcgag ctgcacgtgg acgcagggcc ccctcaggcc gccagggggc ggcatagcgc      60
agcgcgcccc cgaccggaa gacgaagcc caagaacgcc gcttccgccc ggcgcccact    120
tccaagatgg cggcggggcg gggccggggc agggcggacg gagccggcga gcgggatgct    180
gcggactgcg ctgcgcggcg cgccgaggtt gctgagtcgc gtgcagcccc gggcgccctg    240
cctgaggcgg ctgtggggcc gcggggcccg tccagaggtc gcggggaggc ggcgggcctg    300
ggcctggggc tggcggcgct caagctccga gcaggggccg ggcccgcgg cggctctggg    360 gcgcgtggag gcgcgcact accagctcgt ctacacctgc aaggtaggcg cgcggcggga    420
cggaaccggg gacagacccg tatctgacgc tacacggcct gcggggagaa gcggcccgcc    480 gggatccgg gaggcggcgt ggtcaagtca caggaaggag tggagccacc ccttggggct    540
tctgggaggg agcggaggcg gaccatgagg aggggtggag ccgtccctgg ggcggggcct    600
```

```
t                                                               601

<210> SEQ ID NO 74
<211> LENGTH: 601
<212> TYPE: DNA
<213> ORGANISM: Homo sapiens
<220> FEATURE:
<223> OTHER INFORMATION: Pro CALCA_1

<400> SEQUENCE: 74
ggcgggaata agagcagtcg ctggcgctgg gaggcatcag agacactgcc cagcccaagt     60
gtcgccgccg cttccacagg gctctggctg gacgccgccg ccgccgctgc caccgcctct    120
gatccaagcc acctcccgcc aggtgagccc cgagatcctg gctcaggtat atgtctctcc    180
ctccctctcc ctccattcgt cattttctca ctcccttttcc tcctctccct ctctctccgt    240
tagtctcttc atcagatagt ctctgttagt ccgcgattta taccaggctc gtgccctagg    300
ttggatcgga cagtctcaat cccccggctc gctcttcctg ctcggctgcg gactccagtc    360
ttactctctc gcactgcaca caggcttagg ccagtctcgg gacactcagg ctccccaggg    420
accgcgcaca gagcctgagg caagagaaac tttccgcaga cggtgcgatc agggacggcg    480
tctggagccc agcagtccca gggaaattgg ttcagaacct ggaacagagc ggatgggtgg    540
caaataggca cgacgactga gggacaagca gccctaaact gcaagcccca gtcacaggct    600
c                                                               601

<210> SEQ ID NO 75
<211> LENGTH: 601
<212> TYPE: DNA
<213> ORGANISM: Homo sapiens
<220> FEATURE:
<223> OTHER INFORMATION: Pro CALCA_2

<400> SEQUENCE: 75
ctcctccttc ttaactacag cgagggaata acaactcggg gctggggact gggtatctaa     60
gactcgctct ccgcagggtc cgccggcagg gcggccacag gacccgggac tggaactggc    120
ccgggaggac accggcgcgt gtcaggcgca gagcgtgaaa caggcaagct gcgcgcagag    180
cagggcttgg atggcggatc ttgggcacaa tgagccccgg atcctgaagg aagataaccc    240
ctgctgagac cctgtccgga gccttggagc ttttcagcag tttaggctcg gatctccggc    300
ctgggttttc ggtgcagagc tgcttgaaga gttgcgaagg ccgcagtgcg ggcactgagt    360
ggggcgtagt gcttgggcct ctgccactgg ggctgtagca gaagggtatt tgcgctcagc    420
taccacatac ttcagcggaa atgattttttt tccaagacca gaggtttcta acataagaac    480
ctcctgaaac cgtttgtaag tgtgtgtgtc tgtgatgtgt gttttcctaa agagagagtt    540
catagctttc gcccgtgcca cggtgaccgc aaaatgaaag ccagtagacg cagatttttgt    600
g                                                               601

<210> SEQ ID NO 76
<211> LENGTH: 601
<212> TYPE: DNA
<213> ORGANISM: Homo sapiens
<220> FEATURE:
<223> OTHER INFORMATION: Pro COL2A1

<400> SEQUENCE: 76
gctccggggg cgggcggttc aggttacagc ccagcggggg gcaggggggcg gcccgcggtt     60
tgggcgagtt cgccagcctc gaaaggggcc gggcgcatat aacgggcgcc gcggcgggga    120
```

```
gaagacgcag agcgctgctg ggctgccggg tctcccgctt cccctcctg ctccaagggc    180
ctcctgcatg agggcgcggt agagacccgg acccgcgccg tgctcctgcc gtttcgctgc   240
gctccgcccg ggcccggctc agccaggccc cgcggtgagc catgattcgc ctcggggctc   300
cccagacgct ggtgctgctg acgctgctcg tcgccgctgt ccttcggtgt cagggccagg   360
atgtccgtaa gtcttccccc gcccctgcct gcctgcctgc tttccatgcg tccctcagca   420
tccttctccc cggcccgctc cagctctgga cccgcggct ccgggctaaa acggctcccg    480
gggtcgtagc gcgccgactt aggcacagga cacgcagaag ttcaccaaga agagttctgc   540
caatcaagga ctctgtccca gggtcctcgg tgcccatcgc agttgcaagt atttgcaggt   600
c                                                                   601

<210> SEQ ID NO 77
<211> LENGTH: 601
<212> TYPE: DNA
<213> ORGANISM: Homo sapiens
<220> FEATURE:
<223> OTHER INFORMATION: Pro DPY19L2

<400> SEQUENCE: 77
gctgccctca ccggaagctg cacgctctgg gaagcgcaga ggcgggggtg ctgctcgcgc    60
tggggagcac gtgaggggac actcagggac tgcccgcgcg aatggcttcc aacgcatgcg   120
ccccacccca catttcacag tcgccatgac gaccgggagg tccgcaacgg ctgcggggac   180
aagtccgttg aggctgccag gcgagtcagg tctctctgga cctcgcctga ctcggctggg   240
ctgtgcctga aattgaccca gctccaccat actccttgat tatgagaaaa caaggagtaa   300
gctcaaagcg gctgcaatct tccggccgca gccagtctaa ggggcggcgc ggggcctccc   360
tcgcccggga gccggaggta gaggaggaga tggaaaagtc ggccctaggc ggcgggaaac   420
tgccaagggg ctcctggagg tcctccccgg ggaggatcca aagtctgaaa gagcgaaaag   480
gcttggagct agaggtggtg gccaagacct ttcttctcgg cccccttccag ttcgtccgta   540
attccctggc gcagctccgg gaaaaggtgc aggaactgca ggcgcggcgg ttctccagca   600
g                                                                   601

<210> SEQ ID NO 78
<211> LENGTH: 601
<212> TYPE: DNA
<213> ORGANISM: Homo sapiens
<220> FEATURE:
<223> OTHER INFORMATION: Pro NULP1

<400> SEQUENCE: 78
gtcctgcccc cacccctcgc gccaagagtg cgcaggcgcg cagccagctc cccgccccc     60
gaccccgcgc gaagagtgcg caggcgcgcc gacagccgag ttttctgcgc ttccttctcc   120
ctctctccag acgtcgtggt cgttcggtcc tatgtcgcgc cgggccctcc ggaggctgag   180
ggggaacag cgcggccagg agcccctcgg gcccggcgcc ttgcatttcg atctccgtga    240
tgacgatgac gcggaagaag aagggcccaa gcgggagctt ggtgtccggc gtcccggggg   300
cgcagggaag gagggcgtcc gagtcaacaa ccgcttcgag ctggtgagga gcgcggcggc   360
ccgggtgggg gtggggtggc ccttgacgtt gtgggcggg gcgagcgtcc agccgggtcg    420
gggagcgggg ttgtgatgcc aggggtggga agggtgacgt gggtcccagc cgcagtgggg   480
agggcggggc cgtgcgtcgg ggccagggcg acgcggtgg gcgtggcgt ggggtgaaga    540
```

```
cggcgggccg cggagttaga ctgggttcta accccggtga ggtgggcggg gctaagggat    600
g                                                                    601
```

<210> SEQ ID NO 79
<211> LENGTH: 601
<212> TYPE: DNA
<213> ORGANISM: Homo sapiens
<220> FEATURE:
<223> OTHER INFORMATION: Pro TIMP2

<400> SEQUENCE: 79

```
gggctgctgg gagcgcccag agcctgcatt ggccgccagc caccgggagg aggagcagaa     60
aatcctccga gcgcaataaa actgcggccc ggcccaagcc cgcagcaaac acatccgtag    120
aaggcagcgc ggccgccgag aaccgcagcg ccgctcgccc gccgccccc acccogcgc      180
cccgcccggc gaattgcgcc ccgcgccct cccctcgcgc ccccgagaca aagaggagag     240
aaagtttgcg cggccgagcg gggcaggtga ggagggtgag ccgcgcggga ggggcccgcc    300
tcggccccgg ctcagccccc gcccgcgccc ccagcccgcc gccgcgagca cgccccggac    360
ccccagcgg cggccccgc ccgcccagcc cccggcccg ccatgggcgc gcgggcccgc       420
accctgcggc tggcgctcgg cctcctgctg ctggcgacgc tgcttcgccc ggccgacgcc    480
tgcagctgct ccccggtgca cccgcaacag gcgttttgca atgcagatgt aggtaaggag    540
cggcgacccc agccccgcg cggggcccca cctccccgc gaccccgagg gttcgcagac      600
g                                                                    601
```

<210> SEQ ID NO 80
<211> LENGTH: 601
<212> TYPE: DNA
<213> ORGANISM: Homo sapiens
<220> FEATURE:
<223> OTHER INFORMATION: Pro TPTE

<400> SEQUENCE: 80

```
gctcgctcgc gtcccggagg cggagtctgc ggcggcgggc ggaacggggg cgcgcctatg     60
ctagtcacgt gggcgctggg gcggggccgg cggccgttc aaggcagggg gcggggcgtc     120
tccgagcggc ggggccaagg gagggcacaa cagctgctac ctgaacagtt tctgacccaa    180
cagttaccca gcgccggact cgctgcgccc cggcggctct agggaccccc ggcgcctaca    240
cttagctccg cgcccgaggt gagcccaggc cctaagtcct ccgggcgggg gtaggggtgg    300
gggacgctcc tttttgttgg gggggggtct tggaggcgcg aaggcactag gcgcctcggc    360
ggatggctga accctcgcc cgcggctccc cgtgtctttt gggggccgg gtgcgggcgc      420
ggaatccggg aggtgtccgc acaaaaggcc gagaaaaact ccgcgacgcc tccctccctc    480
cctccgccct cccgtcccc tcctctccgc gccgctcct cctcattcaa accggccgg      540
cctgagtggt gttagctcag tcccggccgc cgccgcgtga ggaaatggcc taggagccgg    600
a                                                                    601
```

<210> SEQ ID NO 81
<211> LENGTH: 601
<212> TYPE: DNA
<213> ORGANISM: Homo sapiens
<220> FEATURE:
<223> OTHER INFORMATION: Pro SNX7_1

<400> SEQUENCE: 81

```
aaaccctgtc tctactaaaa atacaaaaaa ttagctgggc gtggtggcgc acgcctgtag     60
```

```
tcccacctac tcaggaggct gaggcaggag aatcgcttga acccggggagg cggaggttgc    120 agtgagcaga gatcacgcca ctgcactcta gcctcggcga gggagtgaga ctctgtctca    180
aaaacaaaca aacaaacaaa caaaaaaacc cagtgatagt cccacttaat aggaagctga    240
gactacagga ggaatagaca tactgctttg gagttgtact aataatgagt aggtttggga    300
ttatctccct ttgaggggct gtgaactgca tgctcaggtg ctcaaagcat ggaggtaggg    360
ggagtatgtg aagaaaggta atattaattg gacagccaaa ggggcaaatt atagtcacgt    420
tttccctact cttcttcctc atcctacccc tcttcctatt tttcttgttt ttggttgaca    480
agcatcaata tggcctttct atgtttagaa aattctctgc cttaggaatt tccatgaaac    540
ttggccagat tggccaagca cacatactct ccagggtttt aatactagaa aaatcaacac    600
a                                                                    601

<210> SEQ ID NO 82
<211> LENGTH: 601
<212> TYPE: DNA
<213> ORGANISM: Homo sapiens
<220> FEATURE:
<223> OTHER INFORMATION: Pro SNX7_2

<400> SEQUENCE: 82
ggggatgcgc ccggcccggg ccagcgctgg tcccggcagt tccgcgtctg cgcagcgggc     60
gaggggctgg agcggggccg gccggggagg tgcaggagac gtgggagcca atgggcacgc    120 tcggggagc cgggctggcg gcgcggtgg cggccggctg ggcgcgcact tcgggatgg       180 agggcgagcg ccgggcatcg caggcgccct cctcgggcct cccggccggg ggcgccaacg    240
gggagagccc gggggggcggc gccccctttc cgggcagcag tggctcttcc gccctgctgc    300
aggcggaggt gctggatctg gacgaggacg aggacgacct ggaggtgttc agcaaggtga    360
gggcggcggc ggcgagtccc gggaaacttc caaggcaact ccgggcgttg ccagcattgc    420
gccgacggct gcctctggcg cgcttgccct cccggggcgg tggctctgag ctggggacga    480
gtgaggtccc ccgggctgct ggaccccgcc tgccagctct ggccgcaccc ggggccgcgt    540
cgcctcgggg cctcaaaccg cagccgctcc ctcctccgca ctttgacctt ccgttcggcg    600
g                                                                    601

<210> SEQ ID NO 83
<211> LENGTH: 601
<212> TYPE: DNA
<213> ORGANISM: Homo sapiens
<220> FEATURE:
<223> OTHER INFORMATION: Pro SNX7_3

<400> SEQUENCE: 83
gccctcctcg ggcctccgg ccggggggcgc caacggggag agcccggggg gcggcgcccc     60
ctttccgggc agcagtggct cttccgccct gctgcaggcg gaggtgctgg atctggacga    120
ggacgaggac gacctggagg tgttcagcaa ggtgagggcg gcggcggcga gtcccgggaa    180
acttccaagg caactccggg cgttgccagc attgcgccga cggctgcctc tggcgcgctt    240
gccctcccgg ggcggtggct ctgagctggg gacgagtgag gtccccgggg ctgctggacc    300
ccgcctgcca gctctggccg caccggggc cgcgtcgcct cggggcctca aaccgcagcc    360
gctccctcct ccgcactttg accttccgtt cggcggggcg gtggcttagt ggagtctgca    420
aagttgtgat ttgttttccc tttctgcttc tctgacacag acatcttcct cgcggcagct    480
```

```
cccgaacctg ggaggctggt ggctcaaaac cgctcccgcc agctgctttt cgggcgaggc      540
cagccctgaa ctctgggaga gcagccaagt ttagagaaat tattcttaat ttagtgttgt      600
t                                                                     601

<210> SEQ ID NO 84
<211> LENGTH: 601
<212> TYPE: DNA
<213> ORGANISM: Homo sapiens
<220> FEATURE:
<223> OTHER INFORMATION: Pro KIAA0746

<400> SEQUENCE: 84
ctgggcaggg aggcagaggg gagggagggg acggggacgg ggaggcgggg aggagccggc       60
gctcggctgg ggctgcgggg gcggcgacgg cgggagcggc agtggcgggg gcggcgggtc      120
cggaggtggc ggcaggtggc cccgcgcgcg gcggccggcc cggccggggg cgggcgggaa      180
ggtggcgcct cgggcggggg ccggtccctg caccaggtga cctgttccgg cccggatccg      240
ggcggcctcg ccatgcagcg gcgcggcgcg gggctcgggt ggccgcggca gcagcagcag      300 caaccccgc cgctcgcggt cggccccgg gccgcagcca tggtcccgag tggcggcgtc       360
ccccagggcc tcggcggccg ctctgcctgc gcgctgctcc tgctctgcta cctggtgagc      420
gccggaccct gcccgggtct tcccctccgc gcggggcccc ggggacgcgg gtggggggcgg      480 ccggggacac ccgccacgcg gggcggggac gccgctgcta gttttctctc ttcctcgtcg      540
ctgcgccccg ggcgttcccg gcacctggga taggtacccc gggcgtggag aggggcgctt      600
g                                                                     601

<210> SEQ ID NO 85
<211> LENGTH: 601
<212> TYPE: DNA
<213> ORGANISM: Homo sapiens
<220> FEATURE:
<223> OTHER INFORMATION: Pro NQO2

<400> SEQUENCE: 85
gacgggcgcg gagcgaggca ccgcaccgcc ggggcgggga gtgggcgggg ctcggggcg       60 gggcggggtg tgggcggggc tcacgggcgg ggcgggtgag tgggcggggc ctcggcgtgg      120
taggcgcgct gcgtaaagag gcctgcagtc ccgcggcgcg gggcaggttc cgggctgctt      180
aggttggcac cggtccgtgg tccccggggg cgcagtcgca gcgctcccgc cctccaggcg      240
tcagcgagtg cgcggtccag tgcggccgga acctggcgca actcctagag cggtccttgg      300
ggagacgcgg gtcccagtcc tgcggctcct actggggagt gcgctggtcg gaaggtgagt      360
gatcccctgt cggggaccgg gggacttggg aaggacagtt cccggactgg acggccagaa      420
cgctctcagg gatttcagct ggccggccat atggccctgt gggtcgtcgc gcccgggcca      480
gggaccattc tgtacatagg atcgtgcttg gctctcacgg aacgcgccca cacgcagggt      540
cccggtgtcg aatcgtctgg tggaatctgc cctcaaccct atggagcggg tgctggtatc      600
a                                                                     601

<210> SEQ ID NO 86
<211> LENGTH: 601
<212> TYPE: DNA
<213> ORGANISM: Homo sapiens
<220> FEATURE:
<223> OTHER INFORMATION: Pro FKBP5

<400> SEQUENCE: 86
```

| | |
|---|---|
| cgcgccttttt gggggcggac tgacagcccc ggggccctat ggaaggcggg tcctgcggcc | 60 |
| ggctggggcg ggacggcgcc gggcgctgcc ccggggattc gggccggctc gcgggcgctg | 120 |
| ccagtctcgg gcggcggtgt ccggcgcgcg ggcggcctgc tgggcgggct gaagggttag | 180 |
| cggagcacgg gcaaggcgga gagtgacgga gtcggcgagc ccccgcggcg acaggtaccg | 240 |
| gcgccatggc cacggagatg gggcggccgg ccgcggcgcc ccgggagccg aacgccctcc | 300 |
| ttccaggtcc cgccgcggtc gcactcgctg cctcagctcc accccacg cggcttcgca | 360 |
| gcccaggagc cgcgtgtcgc gggggagcgg ggtccggaag cctcgagggg agcgcgcggg | 420 |
| aggcctcggc cccactgcgg cgcccctcgc cgcgcccag gggccgcggg gccggtgctc | 480 |
| cccgcgggag gcgcggagac tagtgaccgc gggcgccgct ctccgccccc gccggcctct | 540 |
| cccggcagag gcgaggcggg tcgcgcccgc ccgtcctcac tgggcttttg tttcccgccc | 600 |
| g | 601 |

<210> SEQ ID NO 87
<211> LENGTH: 601
<212> TYPE: DNA
<213> ORGANISM: Homo sapiens
<220> FEATURE:
<223> OTHER INFORMATION: Pro ABCA1

<400> SEQUENCE: 87

| | |
|---|---|
| acggggcggg gaggagggag agcacaggct ttgaccgata gtaacctctg cgctcggtgc | 60 |
| agccgaatct ataaaaggaa ctagtcccgg caaaaacccc gtaattgcga gcgagagtga | 120 |
| gtggggccgg gacccgcaga gccgagccga cccttctctc ccgggctgcg gcagggcagg | 180 |
| gcggggagct ccgcgcacca acagagccgg ttctcagggc gctttgctcc ttgttttttc | 240 |
| cccggttctg ttttctcccc ttctccggaa ggcttgtcaa ggggtaggag aaagagacgc | 300 |
| aaacacaaaa gtggaaaaca ggtaagaggc tctccagtga cttacttggg cgttattgtt | 360 |
| ttgtttcgag gccaaggagg cttcgggaag tgctcggttt cggggacttt gatccggagc | 420 |
| cccacatccc caccacttgc aactcagatg ggaccggagg cggtgttaaa tggggagacg | 480 |
| atgtcctagt acgagctctg gtgacccccag gactctgcgc tgctgcgctt ggggcttgcc | 540 |
| cgacggtgga gaccggggag catctctggg cgtggagacc cgggcgcagt accccgggct | 600 |
| c | 601 |

<210> SEQ ID NO 88
<211> LENGTH: 601
<212> TYPE: DNA
<213> ORGANISM: Homo sapiens
<220> FEATURE:
<223> OTHER INFORMATION: Pro FAM86A_1

<400> SEQUENCE: 88

| | |
|---|---|
| acgacgttcc tcctgacccc cggggacccc ccgggccccg ccccctctct gccccgcctc | 60 |
| actgccctgg gcccgccccc tcttcagtcc aggccgggct ccgcccggt ctgccggcaa | 120 |
| cgctgcggcc ccgcccacgt catggcgccc gaggagaacg cggggaccga actcttgctg | 180 |
| cagagtttcg agcgccgctt cctggcgcca cgcacactgc gctccttccc ctggcaggtg | 240 |
| ggcggcgggg cgagcggaga ggcccgcggg gctcgcggga gtccaggggc agacgggacg | 300 |
| ggtctccgtg ctgaagcccc tggcgctccc gccacgtgag ttcctgggct cccgccggtc | 360 |
| agggccgcgc gacccggtcc ccgtccctgg ggcctggcca gagtcgctcg cacccctcct | 420 |

-continued

| | |
|---|---|
| gccccgcgag ctggcggggg aagctggggg cgtctccaca gccttggggg gcagacgcgc | 480 |
| gctcggtgtg gggtacagtt cacgatcatt ttcacgactt tttaaaggca gtaatcgttc | 540 |
| tggtcactgg gacacagctg ccctcgccca ttctaaaaag tcagcgccgt caggaccgca | 600 |
| g | 601 |

<210> SEQ ID NO 89
<211> LENGTH: 601
<212> TYPE: DNA
<213> ORGANISM: Homo sapiens
<220> FEATURE:
<223> OTHER INFORMATION: Pro FAM86A_2

<400> SEQUENCE: 89

| | |
|---|---|
| aatctttttt tctttttttt tttttgaga cggagtttcg ttctcttgtt gcccaggctg | 60 |
| gagtgcaatg gcgcaatctc ggctcactgc aacctctacc tcccgggttc aaccgattct | 120 |
| cctgcttcag cctcccgagt agctgggatt acaggcgtga ccaccatgc cgggccattt | 180 |
| ttgtattttt agtggagaca gggttttaac acgttggcca gctggtctc aaattcctga | 240 |
| ccgcaggtga tccgcccgcc tctgtctccc aaagtgctgg gattacaggc gtgaaccacc | 300 |
| gcgcctggcc agaagaaatc tttatcttgg tgtgcgggtt cagatgaggg acaaatgtca | 360 |
| tctctcttgg atctgaatct ggaaggatca aggcactgaa gggattttt ttgtttcaga | 420 |
| gagtctagag tctccctctg tcgccaggct ggagtgcagc ggcacgatct cggcttctgc | 480 |
| aaattctgcc tcccgggctc aagcgattct cctgccttag cctccggagt agctgggact | 540 |
| acaggcacgc gtcccatgc ccggctaatt tttgtatttt tagtagagac ggggtttcac | 600 |
| c | 601 |

<210> SEQ ID NO 90
<211> LENGTH: 601
<212> TYPE: DNA
<213> ORGANISM: Homo sapiens
<220> FEATURE:
<223> OTHER INFORMATION: Pro ATXN2L_1

<400> SEQUENCE: 90

| | |
|---|---|
| agaaaccccg tctccactaa aaatacaaaa ttagccgggt gtggtggtgc atgactgtaa | 60 |
| tcccaggtac tcaagaggct gaggcaggag aaacgcttga acccgggagg cggaggttgt | 120 |
| ggtgagccga gatcgcgcca ttgcactcca gcctgggcaa taagaacaaa actccatctc | 180 |
| aaaaacaaac aaaaaaacat catttggatc cactcacctt acagatattt cattgagtgc | 240 |
| ctgcagtgtg ctagagtact gcagagcaag aaataagtca agatcctaac ccttagggag | 300 |
| ctgacattag caggaagaca gaattaaagg agctgttaga atacagtggg ataaattgct | 360 |
| cggcgagcac acaggagggg aaactagcac atctgaaggc aggagcgagg cagggcgaag | 420 |
| gactattacc caaaaagtaa ggcagtgttg tagctaggtg tgcatgtgtt tggtgcaggg | 480 |
| gctgggaaga gttccaatgc taacatttag agcgaagaga ttgagacatt gagagtttcg | 540 |
| ctgggattaa gaccacatgg acttaacagc tccactccat tctccacgtt gcaaagagta | 600 |
| a | 601 |

<210> SEQ ID NO 91
<211> LENGTH: 601
<212> TYPE: DNA
<213> ORGANISM: Homo sapiens
<220> FEATURE:
<223> OTHER INFORMATION: Pro ATXN2L_2

```
<400> SEQUENCE: 91
gctccccggc gacgcgcacg cgcgccagcc cggctcgcgc cctctcgctt tcctccagcc    60
gcgagacccc ctccccttcc ggctcgcggc gcttcctcgc gccgcggtct tctctctcca   120
cccccgacac cgcggggctc ccccgcccg cccacggcgg gccccggctg cccgatcccc   180
ctcgcttccc gcgctctcca gcggggcccc agccccggcc cctctctcc ctcccttctc   240 tctaattccc cttccggacg ctgccatcat gttgaagcct cagccgctac aacagccctc   300
ccagccccag cagccgcccc ccacgcaaca ggccgtggcc cgtcggcccc cggggggcac   360
cagccctccc aacggcggcc tcccggggcc gctggccacc tctgcggctc ctcccgggcc   420
tccagcggcc gcctccccct gctgggggcc tgtggccgct gccgggagcg ggctccgccg   480
gggagccgaa ggcatcttgg cgccgcagcc gccgccgccg cagcaacacc aggagaggcc   540
gggggcagcc gccatcggca gcgccaggtg agaagggtgg gctccgggcg agggagccgc   600
g                                                                   601

<210> SEQ ID NO 92
<211> LENGTH: 601
<212> TYPE: DNA
<213> ORGANISM: Homo sapiens
<220> FEATURE:
<223> OTHER INFORMATION: Pro CBFB

<400> SEQUENCE: 92
agttggaggc gggcgggcgc gcgaggagga ggggtggggc cggcgggggc ggggtgggcg    60
gtgagaggaa gtggcggcgg cggcggcggc ggcggccggg ggcggtgagc gctggggctg   120
cgcgggcggc aggcaacggc tgaggcggcg cggcggcgcgg cggcggcgtg ggttgggctc   180
gagcgggcgg cggcgcctca gactccccgg aacgggagcc cacgcgggcg ggcgcctgaa   240
acaaagggaa gcgggcgtcc gggcgccgcg ggtgggcggt cagtcggtca gcgcggagcc   300
agccagcggg tgcccgcgca agccccgagc gcggccggcc ggcgcggcct cagggcggga   360
agatgccgcg cgtcgtgccc gaccagagaa gcaagttcga gaacgaggag tttttttagga   420 agctgagccg cgagtgtgag gtgaggcagg cgggcgggcg gctaggaggc cgcagcgcgc   480
cccgagtggg cccgggcgga gaaaagtttg ggcggcacgg tccccgggag tcccggtcgg   540
tgcgcccgcg gaggggcaat ctcgccgggg cggccatcgc ccgcagcctc tgcttgccct   600
t                                                                   601

<210> SEQ ID NO 93
<211> LENGTH: 601
<212> TYPE: DNA
<213> ORGANISM: Homo sapiens
<220> FEATURE:
<223> OTHER INFORMATION: Pro RAX

<400> SEQUENCE: 93
ggggctgggt ccagggcgag aggggaggag ccgagggcca gttggctccc cgcctttagc    60
gccgagagcc ccagctaccc cgagcccgaa cttccgactt ctgggactaa ggcggcagcg   120
ggctgagcgc tcgccacccc ccagcgtgcg cagcccgggc gggcttcgcc cgcggagctt   180
gacctagggt cgggacccgt cgggttgcac cgccgcactc gggaagaccc ggcttcgagc   240
ctctcctctc cgtctccaaa gcgccctccc gcctcccggc gctccccatg cacctgccgg   300
gctgcgcgcc agccatggcc gacgggagct tctcgcttgc cggccacctg ctccgcagcc   360
```

```
cgggcgggag cacctcgcga cttcacagca tcgaggccat cctggggttt accaaggacg    420
acgggatcct cggcaccttc ccggcggagc ggggcgcccg gggcgcgaag gagcgggata    480
ggaggctggg cgcgcggccc gcctgcccca aggcgcccga ggaaggctcc gagccctccc    540
cgccgccagc cccggcgccc gccccgagt acgaaggtga gtgcgcaccc ctggctgtgc    600
g                                                                    601

<210> SEQ ID NO 94
<211> LENGTH: 601
<212> TYPE: DNA
<213> ORGANISM: Homo sapiens
<220> FEATURE:
<223> OTHER INFORMATION: Pro ZADH2-TSHZ1_1

<400> SEQUENCE: 94
ttcgcggggg ctgcgccggc gccggggagg cggggggagc gggagcgggc gacgcgggga     60 agggggagc cagggggagg gcgccggccg gaggagggc ggacccgccc gccctagccg    120
agcagagcac agccgagccg agcggccgg gcggggccg accccggcca gcgtcggcgc    180
agagagcggg cggaggcgca ggccatgctg cggctggtgc ccaccggggc ccgggccatc    240
gtggacatgt cgtacgcccg ccacttcctg gacttccagg gctccgccat tccccaagcc    300
atgcagaagc tggtggtgac ccggctgagc cccaacttcc gcgaggccgt caccctgagc    360
cgggactgcc cggtgccgct ccccggggac ggagacctcc tcgtccggaa ccggtgagcc    420
cggcgccccc caaccccacg ccccgttct cgccccgggc tcgcgccgcg ccgcgccgct    480
cccgcagtcc ccagcccgcc cgcgtgccca cactccggcg cgcgctcggg cgcacagcct    540
gagtttgcga gatcccggga gttgaaccc gccgccatct ggcgaaggcg aatgtgatgt    600
g                                                                    601

<210> SEQ ID NO 95
<211> LENGTH: 601
<212> TYPE: DNA
<213> ORGANISM: Homo sapiens
<220> FEATURE:
<223> OTHER INFORMATION: Pro ZADH2-TSHZ1_2

<400> SEQUENCE: 95
aattaaaaag attgacaggt atggtttgtg agagacctat ttgtaattgt cagggtgacg     60
ttggcgagag gaggaggagt aaaaactgaa gcaggaaaag cagctcgatg tgtctgtcta    120
tcagttgaga ctgtctgaaa gctctgcgat ccgaatgtgt gttatatttc actgaaaaga    180
ggagagagcg agagtgcatc tccctctctc ccaggagttt gagggggggg gggacagtcc    240
acgctcatct cgcccaccca gtgaatgtct gctcttcacc ccctttgcac acactctccg    300
ggttgttgtt gcctttttt ttcttggag ggggggtgc ttttgtgta tttttcaaat    360 ttttttctgt tggaagatca agaccggcca aaaatccatg atcaaaatgt gtttgcatta    420
gatttcgcat tggaagaagc ggcgatcctg gcggccaagc cccccgggtg gaagcgcggg    480
gcaccaagtg gcgctccggc ggggtgacac tgtttgatct gtgactgttt ggaaggtgga    540
gcagcgcctg acatctcccc ccggcgcatg tatgtacggg ggcttcactc ctctgtcttg    600
t                                                                    601

<210> SEQ ID NO 96
<211> LENGTH: 601
<212> TYPE: DNA
<213> ORGANISM: Homo sapiens
```

```
<220> FEATURE:
<223> OTHER INFORMATION: Pro ECAT8-TDRD12_1

<400> SEQUENCE: 96
ccctagccgg gcctcccagg gcctccgcgc gtcagtcctc ctggccaccg cgtggcgctg      60
tgccttacgt tgtttgggccg ttgggtggac cacgtggtct ccgacgcctc aaggcctgct    120
cagcgtgcgc gggcatccgg tgggtgcggg aggcccgagg ccaggcaggc agggatcccg    180
cagcgagggg ctggttactg ccaggacgga gcgcattgcc tcgagccgac cccggggtcc    240
gcgagggctc ctggggacga ggagtgtggg gcacctgccg cggggggccc aggcgctaaa    300
ggtggaggga aggaacgcac tcgcggcggg ggcctggccg gggcggacgc agccagcctc    360
acccgcgacg gtaggggact tccagggcga gggggcccat ctgccctcgg gcgccaggag    420
gatgctccag ctcctggtgc tgaaggtgag cgccgccaag ccagaccac gccagaccca     480 cgcagtcccc caccccacc ccagccgcgc acagcctccc accccaccc cagctccgca     540 cagcttccta cacccaccgc agccccgcac agcctcccac cccgacccc aaccctacac     600 a                                                                     601

<210> SEQ ID NO 97
<211> LENGTH: 601
<212> TYPE: DNA
<213> ORGANISM: Homo sapiens
<220> FEATURE:
<223> OTHER INFORMATION: Pro ECAT8-TDRD12_2

<400> SEQUENCE: 97
gcctccgcgc gtcagtcctc ctggccaccg cgtggcgctg tgccttacgt tgtttgggccg    60 ttgggtggac cacgtggtct ccgacgcctc aaggcctgct cagcgtgcgc gggcatccgg   120
tgggtgcggg aggcccgagg ccaggcaggc agggatcccg cagcgagggg ctggttactg   180
ccaggacgga gcgcattgcc tcgagccgac cccggggtcc gcgagggctc ctggggacga   240
ggagtgtggg gcacctgccg cggggggccc aggcgctaaa ggtggaggga aggaacgcac   300
tcgcggcggg ggcctggccg gggcggacgc agccagcctc acccgcgacg gtaggggact   360
tccagggcga gggggcccat ctgccctcgg gcgccaggag gatgctccag ctcctggtgc   420
tgaaggtgag cgccgccaag ccagaccac gccagaccca cgcagtcccc caccccacc    480 ccagccgcgc acagcctccc accccaccc cagctccgca cagcttccta cacccaccgc    540
agccccgcac agcctcccac cccgacccc aaccctacac agccccacc cctcccccca    600 t                                                                    601

<210> SEQ ID NO 98
<211> LENGTH: 601
<212> TYPE: DNA
<213> ORGANISM: Homo sapiens
<220> FEATURE:
<223> OTHER INFORMATION: Pro PROKR2_1

<400> SEQUENCE: 98
atgtgggcag ggtgctaggc tcactgaccc tgaaagagca gaaggtctgg accctcaccc     60
ctcgcacctc cctcacacca cttttcttgc agacatcacc atggcagccc agaatggaaa    120
caccagtttc acacccaact ttaatccacc ccaagaccat gcctcctccc tctcctttaa    180
cttcagttat ggtgattatg acctccctat ggatgaggat gaggacatga ccaagacccg    240
gaccttcttc gcagccaaga tcgtcattgg cattgcactg gcaggcatca tgctggtctg    300
```

```
cggcatcggt aactttgtct ttatcgctgc cctcacccgc tataagaagt tgcgcaacct    360
caccaatctg ctcattgcca acctggccat ctccgacttc ctggtggcca tcatctgctg    420 cccccttcgag atggactact acgtggtacg gcagctctcc tgggagcatg ccacgtgct    480 ctgtgcctcc gtcaactacc tgcgcaccgt ctccctctac gtctccacca atgccttgct    540
ggccattgcc attgacaggt gaggatggtg ggtggggtga gtggtgggc tgggccaggc    600 t                                                                    601

<210> SEQ ID NO 99
<211> LENGTH: 601
<212> TYPE: DNA
<213> ORGANISM: Homo sapiens
<220> FEATURE:
<223> OTHER INFORMATION: Pro PROKR2_2

<400> SEQUENCE: 99
tatctcgaga gtggcgggag gcaaagcagc cggaatgccc gagaaaaaag tgggcgtcag     60
aggcccttgt cctagcgact cccccaccgc accgactgag tcccgggact gcaggatct    120 aagcccttac ctgtctcggc gcctcctttc tgtgcgctct gctgctccgg aagccggatc    180
gagagtcaca gtgtggttgg gcgcaggcgg gccgctcggt tttcacctcg aggacccgga    240
cttgcacttg cagagccgct gcgtggggga tgtccctctt ttttcctcgc ccggcgggc    300 tcctccggcg tgtcagggtc tctgggttcc agctggagtt ggcgctccgg ccccacagct    360 cttccagcg tctcggacct gtgcgccccg cccgcgctg gactccgccc cggggtcccc    420
gcctgcctcc tagtccaggc caagggtgga tgcccagctc ccccacccca ccgcgtgctc    480
tcgggctggt gcgtccaggg cgcgggcacc gtagctccgg ccgcgctgac gcgagtcccc    540
ggcagcgggg gcagcctctc gcacggattt cagcgccttc gcatcccgtc tgaatcggac    600
c                                                                    601

<210> SEQ ID NO 100
<211> LENGTH: 601
<212> TYPE: DNA
<213> ORGANISM: Homo sapiens
<220> FEATURE:
<223> OTHER INFORMATION: Pro NCAM2

<400> SEQUENCE: 100
gcctcgcgga agagcggccg ccgtgcagcg cggagggata cgcctcggcc gcacctcccc     60
tcgccgcgcc cccgccccg ccgccctccc gcccggctc tgctgccgcc gcggcggccg    120
ctgctgctgc tgcttctgcc gccgctgccg ccgccgctgc ctggatatag tgcggcaaga    180
gcggagcttg cagtcacttt gcgaggagga gcgcgcgggc tgcgggcggc tggggcaccg    240
cgggagcggc ggcggcggct ctagcagagg cggccggggc agcgaaaggt tctctctcca    300
gggctggact taataacttt gaaactgtcc accggtgtca cgtcctgaac atgagcctcc    360
tcctctcctt ctacctgctg gggttgcttg tcagtagcgg gcaaggtagg agtgtggcgc    420
tttattgcat ttactttccc tcccccttcc accggccaa gagaggcaaa gagggaggcg    480
caggaagaat gaaatgaaag aactaaagtt acagttattg ctgttgttgt tattattatt    540
ttcgttcttt ctcctagctg tccctaaaat tgtatctgtt gtgtggagac ccttaaataa    600
g                                                                    601

<210> SEQ ID NO 101
<211> LENGTH: 601
```

<212> TYPE: DNA
<213> ORGANISM: Homo sapiens
<220> FEATURE:
<223> OTHER INFORMATION: Pro SPEG_1

<400> SEQUENCE: 101

```
agaaaccccg tctctactaa aaatacaaaa ttagctgggt gtggtggtgc atgcctgtaa      60
tcccagctac tcgggaggct gaggcaggag aattgctcga acccgggagg aggaggttgt     120
ggtgagccga gatcacacca ttgcactccg gcctgggcaa caagagtgaa actccgtctc     180
aaaaaaaaaa aaaactttaa tgtatgcaaa ctgtaaaaaa aattattcct caaggttctt     240
aacctctatg gatgtaattc agtgtttaaa tggttcctcc tataccttt acacactgtc      300
tctcgcgctc tctctctttc tctttgactt cagtatccca gaatgaggat ggggaagagg     360
aggcaagggt aagagtaaca ttctctgcct ctgaatactc atggctcctc tcagcccttc     420
ctgggtttca tccctcaggg ctcaaggtca ggcctgggtc tcctacttgg acttcttaaa     480
aaatttttta ctttatgata actgtagatt cacaggcaat tataagaaat aatgcagaga     540
gatcctgaat taccttcact tggtttcctc ctagggtaac atcttgtatg actatagtac     600
a                                                                    601
```

<210> SEQ ID NO 102
<211> LENGTH: 601
<212> TYPE: DNA
<213> ORGANISM: Homo sapiens
<220> FEATURE:
<223> OTHER INFORMATION: Pro SPEG_2

<400> SEQUENCE: 102

```
caggccgccg gccccccaga cttgtctcct agggcaccgt cccgcgggtg cccccgtggc      60
cgcccagttc cggcgtcccc ccagcccagc tctcagtggc catgcagaaa gcccggggca     120
cgcgaggcga ggatgcgggc acgagggcac cccccagccc cggagtgccc ccgaaaaggg     180
ccaaggtggg ggccggcggc ggggctcctg tggccgtggc cggggcgcca gtcttcctgc     240
ggccccctgaa gaacgcggcg gtgtgcgcgg gcagcgacgt gcggctgcgg gtggtggtga     300
gcgggacgcc ccagcccagc ctccgctggt tccgggatgg gcagctcctg cccgcgccgg     360
cccccgagcc cagctgcctg tggctgcggc gctgcggggc gcaggacgcc ggcgtgtaca     420
gctgcatggc ccagaacgag cggggccggg cctcctgcga ggcggtgctc acagtgctgg     480
aggtcggagg taaagggcag gtgggggccg cgcccggcag gggcggggtg ctcagaggta     540
gaaaagggct gcccaggcca cgcgggtaag gtactggata ctggttccgc cgccttcttc     600
c                                                                    601
```

<210> SEQ ID NO 103
<211> LENGTH: 601
<212> TYPE: DNA
<213> ORGANISM: Homo sapiens
<220> FEATURE:
<223> OTHER INFORMATION: Pro VWC2

<400> SEQUENCE: 103

```
agagcggggg cagcagagga gggagcggaa cgggagccgg gcggaggcgg ctgcggcagg      60
gggaggcggg aggcgggcgc gctagctccc atgctggcct cggtgccact cgcgcgccgg     120
ccgcgctccg ggcttctctt ttccctccga cgcgccacgg ctgcccagac attccggctg     180
ccgggtctgg agagctcccc gaacccctcc gcggagagga gcgaggcggc gccagggtgg     240
```

```
ccccgggc gcgcttggtc tcggagaagc ggggacgagg ccggaggatg agcgactgag    300
ggcgacgcgg gcactgacgc gagttggggc cgcgactacc ggcagctgac agcgcgatga    360
gcgactcccc agagacgccc tagcccggtg tgcgcgccag gcggagcgcg caggtggggc    420
tgggctgtta gtggtccgcc ccacgcgggt cgccggccgg cccaggatgg gcgctggcaa    480
cccgggcccg cgcccgccgc tgctacccct gcgcccgctg cgagcccggc gtccggcccg    540
cgccctgcgc tcatgtatgt aggtttggcg ccggtcttca gggctgaggg tgcatgctgg    600
g                                                                   601
```

<210> SEQ ID NO 104
<211> LENGTH: 601
<212> TYPE: DNA
<213> ORGANISM: Homo sapiens
<220> FEATURE:
<223> OTHER INFORMATION: Pro FOXR1

<400> SEQUENCE: 104

```
ttccggatcc ccaggtcctc gaccccggc atgtaagggt agagtcaagg agggtcttct    60
taagcgttcc tcggcgcggt cctgaagaga ttaaaggcgt caaatggacc gctccacacc    120
tgagctgccg ccaagctaac tcaatccgag ccggcgcatt tgagaaggcg cctgtgaggg    180
tcgctcctca gccgccgcgc tcccactccg cgtccccact ccgcgccgcc gcgcctctgc    240
cagccccgaa ggtggacgtg aagctccaac acctcgactt ctgggcccgc ctccatggcc    300
aggtcccggg actgctggac tgggacatgg ggaacgagct ctttctggcc ttcaccacat    360
ctcacctccc cttagcggag cagaaacgtg agtagcgggt ggggtgaggt gggggggctgg   420 gcgtggcgga gggtggccta ggggctcgcg ggaccccggg gcagacggct ccccagcctt    480
cgcccccacc tccggggag gcttgggggg ccgagcgccc cgcgccccc ccccccgacg      540 gcttagctcc gccgccccg ctccacccc actcgcgaac tctactcggg agtggtttgg     600
g                                                                   601
```

<210> SEQ ID NO 105
<211> LENGTH: 601
<212> TYPE: DNA
<213> ORGANISM: Homo sapiens
<220> FEATURE:
<223> OTHER INFORMATION: Pro TARBP2

<400> SEQUENCE: 105

```
gccccttag tcgaagtaac caatctcagt gcacctaggg gaagtaatcg caatgggagt     60
aaccaatgac gccatgaagc ttctcgtgcg tgcttgaccc tgcctctcca gctgcgacac    120
agatggcgcg cgggctcttg ggttctgtag ttttctcgcg atccaaaagg ctccgtgccc    180
aagtgagtcc ttaccgcctc cctacccagc ggcttcccct ccgctagtac gcatgtccac    240
agcttcacgg accgggagag aggggcgcg gaaggaagga ggcggacgg tattacaaac      300 aaaaaaatac ggccttctcg agaagcgacg gcggagggcc cgctcctccc agaaggcggt    360
gcagcctgcc cgggcgagcc acgcacgcag agggttgtgg ggcggatagc tcccctccag    420
atggaggctc acgaagtagg gtgggcgggg gactccatat cccagcgtgc ccgcggcgg     480 gccctaccgg ccgcgactcc gggcttggcc ccggcctag ctcgtcggct gtgtattggg     540
gcgcgtggag gctgcagtca cggtggcgcc cgcggggacg gaggagggaa tgagtgaaga    600
g                                                                   601
```

<210> SEQ ID NO 106
<211> LENGTH: 601
<212> TYPE: DNA
<213> ORGANISM: Homo sapiens
<220> FEATURE:
<223> OTHER INFORMATION: Pro STXBP6

<400> SEQUENCE: 106

| | | |
|---|---|---|
| agccttgtcc ggagcccgga gccccgcgcg gggcagcccc ccggggagga gcctcgtgct | 60 |
| ctgggacgcg tgccgcgcac tggcacggca ggggcgcgag ccaggctgca cggtaggacc | 120 |
| ggggcgaggg gagccaggcg gtcagggcgg aggccaagcc cgggagatgc ggttgcagcc | 180 |
| gccacggctg ttggggcgcc tggcgctccg tccgaggcgg gtggctgtga ggccagggga | 240 |
| gtaggcaggc tcccagagag attcttccaa gttggcgggt ggcgggagag ggggccgcgc | 300 |
| gccccggcgc agctgctttg tgcgcgcaga gagggactcg tgtccctggt tctctccaac | 360 |
| cctgggaccc gttgtgcggg cagtattggg caagccgcag aacggagcga tttcctccga | 420 |
| gaaagttgag gatggagcct tttttccgc accgtccccg cgatggcatg gccccgaga | 480 |
| atgctgcccc gaggctccca gtgtggggga gctcgggtc gctgcgcctc tagcttgagc | 540 |
| gcagaaatcc gcgaatcact ccgatcttcg cgaactctgg catcttctag gaaaatcatt | 600 |
| a | 601 |

<210> SEQ ID NO 107
<211> LENGTH: 601
<212> TYPE: DNA
<213> ORGANISM: Homo sapiens
<220> FEATURE:
<223> OTHER INFORMATION: Pro PRSS21

<400> SEQUENCE: 107

| | | |
|---|---|---|
| acatcaagaa gtgtggttga agacccgccc ctaggggctg aaagccaggg cgctgccagg | 60 |
| catgagaggc cccaaacagc ccttgggccc aggagggtga agctgggagt agagggcaga | 120 |
| gctcccaccc cgccccgccc ccaggggggcg ccccgggccc ggcgcgagag gaggcagagg | 180 |
| gggcgtcagg ccgcgggaga ggaggccatg ggcgcgcgcg gggcgctgct gctggcgctg | 240 |
| ctgctggctc gggctggact caggaagccg ggtgagctcg gggcgctgct ggcgggatgg | 300 |
| ggaggcgggg gagcgtgggg gaggacggga ggtggaggcc gcgggagtc acttcttgtc | 360 |
| tcccgcagag tcgcaggagg cggcgccgtt atcaggtagg gcgcccagga cgcgcgattc | 420 |
| ctgccagggc cgttgggccg aggtggacgg ggggcggtga gggggtagag gggggccttt | 480 |
| actgctctct cgccccgcc cccgggatcg agaactctgt tggcgtggaa agtaactaac | 540 |
| ggacgctgga gggggatggg cgggccctgc agagcacgtg ggaggatctc cagtgtcacc | 600 |
| t | 601 |

<210> SEQ ID NO 108
<211> LENGTH: 601
<212> TYPE: DNA
<213> ORGANISM: Homo sapiens
<220> FEATURE:
<223> OTHER INFORMATION: Pro LOC388335

<400> SEQUENCE: 108

| | | |
|---|---|---|
| ttggccaggc tgctttcgaa ctcctgacct caggtgatcc gcccacctcg gcctcccaca | 60 |
| gtgctgggat tacaggcgtg agccactgcg cccagccctt tctttccttc tttcttttc | 120 |
| tttctttctc tttcttcctc tctcccctcc cgcctgcctt ccttcttttt ttccttcttt | 180 |

| | | |
|---|---|---|
| ttttctttc ttcttttttt ttttttttgt gaggaaggta gctttagtga aaacagggtt | 240 | |
| tggagttgaa cctatacggg ttcaaattcg acttccgtcc accaccgaga cctgcgctcc | 300 | |
| ctgagggact cgctttccca tccgcgaaac caggacggcg ccgcctacac cccgcggcgt | 360 | |
| tcggggcggg ctgaatgggt cgctgagtgg gggctacacc cacgcccttc gctccccgcc | 420 | |
| cccgggcgga gcgacggcca cggcagtgtc cccaaggcac cgaaaccgag gcggggtct | 480 | |
| cggtccctcc gcgcaaggag gaaggcggac cgtacgtggc aggactcacc gccccgcacg | 540 | |
| tggcaggact caccgccccg cgccgtgttc tccgagccat ggcgccagcg ctgtggcggg | 600 | |
| c | 601 | |

```
<210> SEQ ID NO 109
<211> LENGTH: 601
<212> TYPE: DNA
<213> ORGANISM: Homo sapiens
<220> FEATURE:
<223> OTHER INFORMATION: Pro MAN2B1-MORG1_1

<400> SEQUENCE: 109
```

| | | |
|---|---|---|
| agctaggtcc ttccaggacc ctagcgctga aggtccatgg gacgacacc ctggattccc | 60 | |
| atggacacac tacaccggct aggaaaaccc ggccccctta ggaaaagcac ttctgctcct | 120 | |
| accggcatta agaggcattc cgtcttggaa ttccggcatt aagaggcatt ccgtcttcat | 180 | |
| agcccgtgag acgccagtgt caccttagc ccaaccagtg ccctgagggt ggcattttcc | 240 | |
| taccttcctg taacgacccc cgggattgcc cagggctaca gcctctctcc cgtgagcctc | 300 | |
| cagaccgcgc cctggccccg cccccacc cgattggccc ggccgggtct ggggcgggg | 360 | |
| cgtttgcccg gccttccag ggccgggaa ccccaggagg aagctgctga gccatgggcg | 420 | |
| cctacgcgcg ggcttcgggg gtctgcgctc gcggctgcct ggactcagca ggcccctgga | 480 | |
| ccatgtcccg cgcctgcgg ccaccgctcc cgcctctctg ctttttcctt tgttgctgg | 540 | |
| cggctgccgg tgctcgggcc ggggatacg aggtgagtgg ggcctccgag ctgaaacgta | 600 | |
| c | 601 | |

```
<210> SEQ ID NO 110
<211> LENGTH: 601
<212> TYPE: DNA
<213> ORGANISM: Homo sapiens
<220> FEATURE:
<223> OTHER INFORMATION: Pro MAN2B1-MORG1_2

<400> SEQUENCE: 110
```

| | | |
|---|---|---|
| ttcctcctgg ggttccccgg ccctggaaag gccgggcaaa cgccccgccc ccagacccgg | 60 | |
| ccgggccaat cggggtgggg ggcggggcca gggcgcggtc tggaggctca cgggagagag | 120 | |
| gctgtagccc tggcaatcc cggggtcgt tacaggaagg taggaaaatg ccaccctcag | 180 | |
| ggcactggtt gggctaaagg tgacactggc gtctcacggg ctatgaagac ggaatgcctc | 240 | |
| ttaatgccgg aattccaaga cggaatgcct cttaatgccg gtaggagcag aagtgctttt | 300 | |
| cctaagggg ccgggttttc ctagccggtg tagtgtgtcc atgggaatcc agggtgtccg | 360 | |
| tcccatggac cttcagcgct aggtcctgg aaggacctag cttgcctaag gaggatct | 420 | |
| gatgaagagt cctatactgt ggggattggg acgttgggta ataccctg gagtaccagg | 480 | |
| gatgggatcc agcctggttg agaaggatcc ctgggtgttc cggagagaaa agagggtctg | 540 | |
| acaagtgggg aaggaccccg agtctttcat gcctttccca attcctacca gttcattctc | 600 | |
| t | 601 | |

<210> SEQ ID NO 111
<211> LENGTH: 601
<212> TYPE: DNA
<213> ORGANISM: Homo sapiens
<220> FEATURE:
<223> OTHER INFORMATION: Pro MORG1-C19orf56_1

<400> SEQUENCE: 111

```
ttcctcctgg ggttccccgg ccctggaaag gccgggcaaa cgccccgccc ccagacccgg      60
ccgggccaat cggggtgggg ggcggggcca gggcgcggtc tggaggctca cgggagagag     120
gctgtagccc tgggcaatcc cggggtcgt  tacaggaagg taggaaaatg ccaccctcag     180
ggcactggtt gggctaaagg tgacactggc gtctcacggg ctatgaagac ggaatgcctc     240
ttaatgccgg aattccaaga cggaatgcct cttaatgccg gtaggagcag aagtgctttt     300
cctaaggggg ccgggttttc ctagccggtg tagtgtgtcc atgggaatcc agggtgtccg     360
tcccatggac cttcagcgct agggtcctgg aaggacctag cttgcctaag aggaggatct     420
gatgaagagt cctatactgt ggggattggg acgttgggta ataccctg  gagtaccagg     480
gatgggatcc agcctggttg agaaggatcc ctgggtgttc cggagagaaa agagggtctg     540
acaagtgggg aaggaccccg agtctttcat gcctttccca attcctacca gttcattctc     600
t                                                                      601
```

<210> SEQ ID NO 112
<211> LENGTH: 601
<212> TYPE: DNA
<213> ORGANISM: Homo sapiens
<220> FEATURE:
<223> OTHER INFORMATION: Pro MORG1-C19orf56_2

<400> SEQUENCE: 112

```
ccttagaaac ccacgcttgg gtgtaacctt attattgttc ttcctgacct acttcctgtt      60
tatcacttcc gggttcatca tttttggcatt tcggtgatcg ggttggaact attgaagccc    120
gctttcaggt tcttttcccc attttcccctt tgaaaggaag acttctggct tctcctaaat   180
ctccgttctc tgggtaaggg gagtccaagc ctctgtcatg aggaacggaa atgcgagggc    240
ctcgggtgtt actctaaaat ccgccctcag cttgcacgcc ggaagctgcg attcctgcag    300
cggaagaggc gtgatctggc cttcgactcg ctatgtccac taacaatatg tcggacccac    360
ggaggccgaa caaagtgctg aggtgaggac cccagcgtcg tgggcacggg ttcgggttgt    420
gggtgtggat cggggccctg ggaagcgcct gtctatcccg ggggcaggac ctgagcgccc    480
ctgaccctcg agcctgtcgc aggtacaagc ccccgccgag cgaatgtaac ccggccttgg    540
acgacccgac gccggactac atgaacctgc tgggcatgat cttcagcatg tgcggcctca    600
t                                                                      601
```

<210> SEQ ID NO 113
<211> LENGTH: 601
<212> TYPE: DNA
<213> ORGANISM: Homo sapiens
<220> FEATURE:
<223> OTHER INFORMATION: Pro C19orf56-MORG1_1

<400> SEQUENCE: 113

```
ccttagaaac ccacgcttgg gtgtaacctt attattgttc ttcctgacct acttcctgtt      60
tatcacttcc gggttcatca tttttggcatt tcggtgatcg ggttggaact attgaagccc    120
```

```
gctttcaggt tcttttcccc attttcccctt tgaaaggaag acttctggct tctcctaaat    180
ctccgttctc tgggtaaggg gagtccaagc ctctgtcatg aggaacgaaa atgcgagggc    240
ctcgggtgtt actctaaaat ccgccctcag cttgcacgcc ggaagctgcg attcctgcag    300
cggaagaggc gtgatctggc cttcgactcg ctatgtccac taacaatatg tcggacccac    360
ggaggccgaa caaagtgctg aggtgaggac cccagcgtcg tgggcacggg ttcgggttgt    420
gggtgtggat cggggccctg ggaagcgcct gtctatcccg gggcaggac ctgagcgccc     480 ctgaccctcg agcctgtcgc aggtacaagc ccccgccgag cgaatgtaac ccggccttgg    540
acgacccgac gccggactac atgaacctgc tgggcatgat cttcagcatg tgcggcctca    600
t                                                                    601
```

<210> SEQ ID NO 114
<211> LENGTH: 601
<212> TYPE: DNA
<213> ORGANISM: Homo sapiens
<220> FEATURE:
<223> OTHER INFORMATION: Pro C19orf56-MORG1_2

<400> SEQUENCE: 114

```
aagaacctga aagcgggctt caatagttcc aacccgatca ccgaaatgcc aaaatgatga     60
acccggaagt gataaacagg aagtaggtca ggaagaacaa taataaggtt acacccaagc    120
gtgggtttct aaggcgcgga attttccgta cagaccgatt taaggctgca aggaaggagt    180
cctgggagca tggctttccc tgagccaaag ccgcggcctc cagagctgcc gcagaaacgg    240
ttgaagacgc tggactgcgg gcaggggca gtgcgagccg tacgatttaa tggtgagcgc     300
cttcgtcttc attccgggtc ctcctcccgc ctcctgagat cgacggccca gtaaccccgg    360
cctggtgttc cccagtggat ggcaattact gcctgacgtg cggcagtgac aagacgctga    420
agctgtggaa cccgcttcgg gggacgctgc tgcggacgta cagcggccac ggctacgagg    480
tgctggatgc ggccgggtga gccggggacc aggctgggat gggagcgctg aggctgggat    540
ccgaggtcga tgctgatcct cctcctcctt tactccagct cctttgacaa cagtagtctc    600
t                                                                    601
```

<210> SEQ ID NO 115
<211> LENGTH: 601
<212> TYPE: DNA
<213> ORGANISM: Homo sapiens
<220> FEATURE:
<223> OTHER INFORMATION: Pro DUSP4_1

<400> SEQUENCE: 115

```
ggggtccggg cgccccccgc cgcgctgcgc ctccgcctcc cgccgccgca ttccgcgcat     60
tcttccgcgc gggtagggtc tgcgcttccg agcccggtag gcagttcaga cccccccaca    120
cccatcaaag agccgctcct ccccccgca ggcgccttcg ccgcctccct cccttccttt     180
cctttccgct cctcttccga cctgtccacc cgggaggaag ggagctggaa aggggcgga    240 aacctctccc ctccaaaaag cacaacaaaa ctgttcagtg cggaggagcc gggttcgccc    300
ctgccggaca gcgggggggct tgttccccg cagttgtttc ctgcccattt gacctgtcag    360
ctgctgggga aacgctgctg ttgaccttg gttgaactgc taaggcgatt ttgctgattt    420
ttctttcttt ttccgcgagg gctgtctttt gctcctccaa atgagcccag tcccctcccc    480
ttctccccaa agcgctccaa gagaaagtgc caggaagggg cttgtcccgg aaggcctggc    540
ggctgagcgg ggccaggtcc tggttaggcc accagggtgg gcgtccgcgc cattgtttga    600
```

```
g                                                                601

<210> SEQ ID NO 116
<211> LENGTH: 601
<212> TYPE: DNA
<213> ORGANISM: Homo sapiens
<220> FEATURE:
<223> OTHER INFORMATION: Pro DUSP4_2

<400> SEQUENCE: 116
ggggcctggc ggggtagtac ctagcgcccc ctcccccggg agcgcggagg agcattaata     60
aacctctaag ccgaggagaa aactctggct ggggcagtgc gctgagcgcc ggaggagcgt    120
aggcagggca gcgctggcgc cagtggcgac aggagccgcg cgaccggcaa aaatacacgg    180
gaggccgtcg ccgaaaagag tccgcggtcc tctctcgtaa acacactctc ctccaccggc    240 gcctcccct ccgctctgcg cgccgcccgg ctgggcgccc gaggccgctc cgactgctat     300
gtgaccgcga ggctgcggga ggaagggac agggaagaag aggctctccc gcgggagccc    360
ttgaggacca agtttgcggc cacttctgca ggcgtcccct cttagctctc gcccgcccct    420
ttctgcagcc taggcggccc gggttctctt ctcttcctcg cgcgcccagc cgcctcggtt    480
cccggcgacc atggtgacga tggaggagct gcgggagatg gactgcagtg tgctcaaaag    540
gctgatgaac cgggacgaga atggcggcgg cgcgggcggc agcggcagcc acggcaccct    600
g                                                                601

<210> SEQ ID NO 117
<211> LENGTH: 601
<212> TYPE: DNA
<213> ORGANISM: Homo sapiens
<220> FEATURE:
<223> OTHER INFORMATION: Pro ACOT4

<400> SEQUENCE: 117
gatctcattg gcttttggtt tcaccacaaa ttgatcatcc aacaactttc attccaacaa     60
ccgagggtgg tgtgaggcag agaggctttc tacggggtgg gttgggcgcc acaccttgcg    120
cgccccgggg cccaaggaga cgaccctgaa gaggagcctg gctactttg cctcagacga     180 gtccggagcg ccgggttaac cggtctgaag tcccagggc tttctgggac tgctcagcca     240
ccggcagctt ccggcaccag gggacgccgg acgccgtccg acattcggc gcgcttgcca     300 cgatcttgga cgggtctcgg gcctcgacct ttgaattccc cgctccggct ccaagatgtc    360
agcaacgctg atcctggagc ccccaggccg ctgctgctgg aacgagccgg tgcgcattgc    420
cgtgcgcggc ctggccccgg agcagcgggt tacgctgcgc gcgtccctgc gcgacgagaa    480
gggcgcgctc ttccgggccc acgcgcgcta ctgcgccgac gcccgcggcg agctggacct    540
ggagcgcgca cccgcgctgg gcggcagctt cgcgggactc gagcccatgg ggctgctctg    600
g                                                                601

<210> SEQ ID NO 118
<211> LENGTH: 601
<212> TYPE: DNA
<213> ORGANISM: Homo sapiens
<220> FEATURE:
<223> OTHER INFORMATION: Pro SOX13

<400> SEQUENCE: 118
actctctgtc cctcccttct tctgcaagtc cccaccctcc ctccctcctc ccctgcgcg     60
```

```
ctctcggtct ccctccctct ttctcctcta ggctgtccag tcgcctcgca gcagcgagcc      120
gcgagcgccc ttctccagtc ccggcttgga actgaactgt gtgagcacgg gtcctggaac      180
ccgggcccag aaccggcgag cccaggtctg agcccagagc tcagcggtca gcctcgtagg      240
ccctgactcg gaatcgagcc gaggcgctga ggttggagcc ggagagcgtg agagccgaag      300
agcagggagg gcgggccggc tgcgcgtccg acgagtcgca gagcaggacc gcggaaggca      360
gggagacggc cgcaagccca gggcagaggg cagagggcag agagcggcct ggctcggcgg      420
agagggcgcc gcccggccgg aaccaagctc gccgcccggg acgcgggcc ccgtggggcg       480 cggacccagg gtggccgtgg gtccgcagcg actccccggc cgacggcggg gggcgtgccc      540
cctcccagcc cagcctcccc aacccggccc gcccgccgcg tcgcggggc atgtgagcgg       600 g                                                                      601

<210> SEQ ID NO 119
<211> LENGTH: 601
<212> TYPE: DNA
<213> ORGANISM: Homo sapiens
<220> FEATURE:
<223> OTHER INFORMATION: Pro FAM89A

<400> SEQUENCE: 119 gaggggggcgg ggccgggggg gcgtggcgcg ggaggggaag tgggcggggc accgccggga      60 aggggggcggg ccgggggaaa gccttggttc gctgcagcgg ggcaggcgcg tggccgggcc     120
gcggcgcgat gagtggggcc cggcggcgc ccggggccgc gggcaacggc gcggtccggg       180
ggctgcgggt ggacgggctg cccccgctgc caaagagctt gagcgggctg ctgcactcgg      240
cgtcgggcgg cggcgcgtct gggggctggc ggcacctgga gcggctgtac gcgcagaagt      300
cgcgcatcca ggacgagctg agccgcgggg gcccgggcgg cggcggggcc cgggcggcag      360
cgctgcccgc caagcctccc aacctggacg ccgctctggc gctgctccgc aaagagatgg      420
tgagtggggc tccgcgagct ggggctcttc ccggccgggc tcgccgtccc gggaaagttc      480
gcggggaccg cgctctgtcc ggaagtcccc gcgcccaccc gcccttcgg gctcctccgc       540 cccaggcgcc ggcgccgtcc tcccaacgac ccccattttt ctcgcgtgct ccgtgcccac      600
g                                                                      601

<210> SEQ ID NO 120
<211> LENGTH: 601
<212> TYPE: DNA
<213> ORGANISM: Homo sapiens
<220> FEATURE:
<223> OTHER INFORMATION: Pro LOC389151

<400> SEQUENCE: 120
agagcgggtc ctccaggggg cggagcattg cgtgacattt tgcgacttcg gttccgctgc      60
cgtcatttac aacataattg gctttgcagt gcgcatccgg gtctgcatca ggaaggccca     120
agggtccaac gagctaagct gagcccggtg gccggcgagg caccaccagc agcccagact      180
acggtccccc aggaggcgcc ccgggagctc cgaggactcg ccccgcgtcg cgcggtcctg      240
cgccccgctc gtcccaacca gcctccccta ccaccgacat ctgttacttc aaagaggact      300
tcaccgccgc gctccccacg tccgctgcta ggcccaggag cgccgtccac agcgccgtcg      360
aggcgatggt cagccggccc cgcagcccca gcgccttccc tgctccctgg tggggacagc      420
agccaggagg accccggccct gccaagcgcc tccgattgga ggagcccgcg ggccccgaac     480
cccgcgcggc acccagcctg aagacccggg cgggggaccc ggccgtggac gcgctcacct     540
```

```
ccatagtggt cctggccgcg ggctgtgccc tgcgtgtgcc cctggacgac gtcgacctgg    600
t                                                                   601

<210> SEQ ID NO 121
<211> LENGTH: 601
<212> TYPE: DNA
<213> ORGANISM: Homo sapiens
<220> FEATURE:
<223> OTHER INFORMATION: Pro H2AFY_1

<400> SEQUENCE: 121
ccggggcgcc gggcggcacg ggcgcggagg ccggacgctc ggggccgcga agggatgtga    60
cgagcggcgc gctgtgcatt gtgggaagcc ggccgcgagg actggttcca gttcactcgg    120
cagcggcgcc gggcggaggg ggagagcgcg ggccgcgcgg gcgggaagcg aagaggcggg    180
cgggccagcg aggagcgcgg agagaaaagg cgcgagcggc caggagggct caggccgaga    240
caccttgcag ctgccgccgc cgccaccgag ccgccgcgta agtgccgcgc gggcccccctt   300 gccgcactcc ctgtccccgc cgctcgggtc cggccgcggg tgcccgggag cggcccggcc    360
tggcgcgcac cggtgtggtg cgggccgggc tcgggccgcc gggttcggtg tggcccacgc    420
cgggtcctcg cgcgtgcact acgtcctccc aggccttgtc gggccgcgcg ggattcccctt   480 tggttttgtt caaaaagaa acctggaaac caacttctct tcgaaacgca tccccctgcc     540
cgcgcctggg cgcttttgtg ggaaaaaagc ggtgctggcg cctaccctgg cgacccttcc    600
t                                                                   601

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gttttgttag aaacgggagg cgttc                                          25

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgggttgggg tcgggattc                                                 19

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ttttcgtttc gttcggtcgg                                                20

<210> SEQ ID NO 125
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cgggatcgtt ttgagttttc ggc                                              23

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gggcggtttt gagtttgcga tttc                                             24

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gggtttagga tcggtgtatt tttcgtc                                          27

<210> SEQ ID NO 128
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tggttgtttt ttagttgcgc gttttc                                           26

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cgaagcgttt gggagatatt ttagaaac                                         28

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggataggcgg tttagaacgt gc                                               22

<210> SEQ ID NO 131
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 131
cgcgatgttt cggagcgc                                                    18

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
aggtttaggt ttagatttag agtcgttcgt c                                     31

<210> SEQ ID NO 133
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
agggtttttt atttagtgat aaagttcgtg g                                     31

<210> SEQ ID NO 134
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agtattatac gtaagttatt gtttcgtttc g                                     31

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tttcgtttgt gggcgggttc                                                  20

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tcggtttacg ttgttttgga gtttgtattt c                                     31

<210> SEQ ID NO 137
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 137
tcgtattttt cggattgttt gttcgacgc                                          29

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
agagtttgtg ggaattcggt agtc                                               24

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggcgtttcg tttcgtcgc                                                     19

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
agtttaggtc gttagtgcgt acgc                                               24

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
agagagttag gggttggacg tc                                                 22

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
attttttgaa ttcgcggttt cgc                                                23

<210> SEQ ID NO 143
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 143
gataggtgtt tggggagaa ggc                                          23

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tgggggtacg aaatcgatta gcgttac                                     27

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggtagtttcg cgagcgaagt c                                           21

<210> SEQ ID NO 146
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
agcgacgtta ttcgtattta atggcgaac                                   29

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gcgttagggg aggttttggc                                             20

<210> SEQ ID NO 148
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggtttcgttt ttacggttcg atttcgttc                                   29

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 149
ctatcgccgc ctcatcgt                                            18

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tgcgcggatg tttcggc                                             17

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151 agttttagt tttggacgtt cgtagcg                                   27

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cgatcgggaa ttggcgtatg c                                        21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ggcgttcgga gtcgtcgtta c                                        21

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154 gggttttag acgaacgtag tcgtagc                                   27

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 155
gggagttatt ttgacgtcgg agtc                                              24

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggttgttttg tttttcgggc gtc                                               23

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
attttatttt acgtcgcggc gtaat                                             25

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tttttgtatt ggttaagtta gcgagtcg                                          28

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cgagttcggg atcgagttat cgc                                               23

<210> SEQ ID NO 160
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tttatcggtg attcggttcg taggac                                            26

<210> SEQ ID NO 161
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 161
ttcgttttag tttcggtagt ggcgtc                                26

<210> SEQ ID NO 162
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162 tttttcgtt ttaggttttc gttataggg                              29

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ggaggattat agagttgttt ggcgtagc                              28

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gtgggtcggt cgttaacgac                                       20

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
aagattatat tttttaaagg ttttcgcgga                            30

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
agcggtgcgt tttagggtac                                       20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167

```
gcgtttcggt tcgtttcggc                                            20
```

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
tgtttgtgtt tacgcgggag c                                          21
```

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169

```
cggtagagcg cgaggtc                                               17
```

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170

```
agatagttag ttttcggatt tcgcgc                                     26
```

<210> SEQ ID NO 171
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171

```
gcggttttgg agttagagtt tagtgc                                     26
```

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172

```
gtcgggagga ttacgggc                                              18
```

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aattagtttg cgggaacgta gtcg                                              24

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gcgttattga tattttagag attagcgggt atc                                    33

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ttttatgtag gaagtcgagg ttggc                                             25

<210> SEQ ID NO 176
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
acgtttaaag ttttgaggtt taagaggaat c                                      31

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cgtgttagtg taggatggat tcgtc                                             25

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ggggcgtttt ttagtttgac gt                                                22

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gagtttggtt aaggagcgtc gc                                                22

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tgtcgttttc gggaagcgc                                                    19

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ggggtttcgt ggttttttcg c                                                 21

<210> SEQ ID NO 182
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ggcggttaat taaatattga gtagaaagtc gc                                     32

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gagtaggtag aagatgaagt cgtagaggtc                                        30

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gttgcgtacg cgtttagatt tcgtttc                                           27

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
atgttcgttc gttaggcgta cgc                                               23

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
agggtttcgt ttcgtgtttg acgtc                                          25

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
agtttgttta tttatgttta agatgggcgg                                     30

<210> SEQ ID NO 188
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ttttcggtta ttttaggttt agtcgtttat ttc                                 33

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agtcgtattt tatgaggcgt gg                                             22

<210> SEQ ID NO 190
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cgttgaaaga gtttgaatcg aagcgttc                                       28

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cgttttgagt tcgtcggtcg ttc                                            23

```
<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gaggttaagg gcgtttcggt ttc                                              23

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gatttatagg gttttcgttc gtttaatcgc                                       30

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gggttcggtt tatgacgagt agc                                              23

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ggttcggtag tcgagtagtt tggtaac                                          27

<210> SEQ ID NO 196
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtaggttttt agtattgacg atagcgagc                                        29

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
gttacgacgg aggcggattc                                                  20

<210> SEQ ID NO 198
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gtttgaaggg aagggttaat ttttgagtat ttc                              33

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tcgtttcggt cgcggac                                                17

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gaaaccaaaa acgctacgac gcg                                         23

<210> SEQ ID NO 201
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tccaaacata accaataata cccaaaccaa cg                               32

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctcaaactaa cgacgcgatc g                                           21

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccgaactaac cctactctaa caaactcg                                    28

<210> SEQ ID NO 204
<211> LENGTH: 23
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tcctatcgct aaactcacgc tcg                                          23

<210> SEQ ID NO 205
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aaaacacgaa aaacgaaaac gacgcg                                       26

<210> SEQ ID NO 206
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aaaacgaaac tcaaaactcg ctccg                                        25

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207 atactttttaa taacactcgt ttacatctaa tcg                              33

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ccgaaacgcg actacgaaac g                                            21

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ttccgaaaca cgcccgatcg                                              20

<210> SEQ ID NO 210
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 210
cctcccgctc cgaataacg                                              19

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ctaactcatc caacccgacc g                                           21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ctcaaatccc cgtctttacc g                                           21

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
accaacgcca acaacgcg                                               18

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
actttacgac aacgacaccg acg                                         23

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cgctaacacc gaaacaacgc g                                           21

<210> SEQ ID NO 216
<211> LENGTH: 23
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 216
cccaaaaact cgactatacg cgt                                            23

<210> SEQ ID NO 217
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
acgaacgaaa aactcgaacg aaaactacg                                      29

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ccgcaaaacg tacgacgcg                                                 19

<210> SEQ ID NO 219
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tcactcaact tcaactcaac gctacg                                         26

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
accctaaacg ttcacaaccc g                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ccgaactacg ctttccttcc g                                              21

<210> SEQ ID NO 222
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 222
acctattcac ctactccccg cg                                              22

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ccgaaaaacg aaacgaaatc gcg                                             23

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
taacgacgac tcctacgccg                                                 20

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
aaacgaaaac gataccgacc tccg                                            24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
gccgctatac actaacgctt aacg                                            24

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cgttatatat cgttcgtagt attcgtgttt                                      30

<210> SEQ ID NO 228
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
gccaccaacg cttcgcg                                                        17

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
cgaaaaaccc gacccgaacg                                                     20

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
tccgcgcgta cgtacttcg                                                      19

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
tacccgaccg aaccgaaacg                                                     20

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ccaccgctaa cgcgacga                                                       18

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gacgaaacga ccgacaaaac g                                                   21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 234
cccgaactaa acttcgacgc g                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
acaaaacccg accaccaaac g                                              21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
tacgaatcac taaacccgtc cg                                             22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cgcaaaacta cgaccgtccg                                                20

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238 aaaacccta acgaaaacgt cacg                                            24

<210> SEQ ID NO 239
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gctaccgact aacacttaac cgaacg                                         26

<210> SEQ ID NO 240
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 240
acgaaaacta cgaaacaatc acgctcg                                        27

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ctcgacgaac aacgctctaa ccg                                            23

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ccgctatttt atttccgata taaaaccgcg                                     30

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
cgtcctattt ttaccgaacg cg                                             22

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
gcgaaaacaa caaaacgtac g                                              21

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245 ccttttccc aaaccaactc gcg                                             23

<210> SEQ ID NO 246
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
```
gaaaccttaa taccgtaact ccgactacg       29

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
atctcgaacg ctaaaacgac g       21

<210> SEQ ID NO 248
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
cgctacgaaa ctctaacgat acccg       25

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
acgcactcgt aatccgaact cg       22

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gcgtaaccgc taaacgcg       18

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
cgacgacgct aatacgcacg       20

<210> SEQ ID NO 252
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
cgaccctaat cacgtaattc gaacg                                    25

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ccgcttccct aaaaacgacc g                                        21

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tccgccctcc taactataac cg                                       22

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
ccgcctttaa atcccgcga                                           19

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
aacaacgata actccgaacc tcg                                      23

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accgctcaaa accgaaatac tccg                                     24

<210> SEQ ID NO 258
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
cgatatacga aactccccat aacgaacg                                 28

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cccgctacca ttcaaaaacg acg                                            23

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
aaatccgaac gcgctctttc g                                              21

<210> SEQ ID NO 261
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
ccgaacctcg atatcaacgc tatcg                                          25

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
ctttcgaaaa tccctacgcg tacg                                           24

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ctcacccaac gatcgcaacg                                                20

<210> SEQ ID NO 264
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
acccaaaata aaaccgaaac ccaaaacg                                       28

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
gaaacccaac ctcttaacga acg                                          23

<210> SEQ ID NO 266
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
aataattcta actcctacga atcccg                                       26

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
tccctactcg attacgattc attcg                                        25

<210> SEQ ID NO 268
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 268
acatccacgc taccgctcg                                               19

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 269
ccgaacccga ctttaacgta cg                                           22

<210> SEQ ID NO 270
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 270
caaaacctct accgaaaacg taaaacacg                                    29

```
<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cgaaaacgaa acctaaacgc cg                                              22

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
actcacccga cttctaaacg tacg                                            24

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
accaaaccaa ccgtaaacgc g                                               21

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
gaaacccgaa accgctccg                                                  19

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cgactcccca aattctacgc g                                               21

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aaataataac gaaccgaacc gctacg                                          26

<210> SEQ ID NO 277
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
aaacataacg atttctcaaa ccgaaaacg                                29

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
tcgggtgggc ggttgtttgg att                                      23

<210> SEQ ID NO 279
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
tagcgcgtgg tcgtgtattt cggaat                                   26

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
tcgcggttga gttattatcg gtgtagtggt                               30

<210> SEQ ID NO 281
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
aaacttaaac aaacatacaa aatttaacat ttcccatc                      38

<210> SEQ ID NO 282
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
tcggttggta ggcggtttgg tttagt                                   26

<210> SEQ ID NO 283
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
cgcgacgtca aacgccacta cg                                          22

<210> SEQ ID NO 284
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
tcgaagaggt ttagggcggt gttcg                                       25

<210> SEQ ID NO 285
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
acgacgtaaa actcgaaacc cgaccc                                      26

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
tcggtcgtcg atttttagtt tttcggcgg                                   29

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
cgacaaacgc ttcccgcgac taaa                                        24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
ttcggtcgta ggcgggtttt ggag                                        24

<210> SEQ ID NO 289
<211> LENGTH: 24
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 289
cgctacgact atcgaacgcg cctc                                          24

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
aggcggtggt tgtagtagta gcgg                                          24

<210> SEQ ID NO 291
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
aacgacttat atactctcaa ccgtctccct cta                                33

<210> SEQ ID NO 292
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
aaataattcc atccgaattc ttccccgcc                                     29

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
agaatgttac gtgggtttgg aggtttaagg ag                                 32

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
agtcgggttt gcgcggtagt g                                             21

<210> SEQ ID NO 295
<211> LENGTH: 24
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 295
ttagcgtcgt taaggttgcg aggg                                            24
```

METHODS FOR PREDICTING ESOPHAGEAL ADENOCARCINOMA (EAC)

This application is the U.S. National Phase Application, pursuant to 35 U.S.C. §371, of PCT International Application Ser. No. PCT/US2009/034508, filed Feb. 19, 2009, designating the U.S. and published in English on Aug. 27, 2009, as publication WO 2009/105533 A2, which claims priority to U.S. Provisional Application Nos. 61/066,281, filed Feb. 19, 2008; 61/131,748, filed Jun. 11, 2008; and 61/132,418, filed Jun. 18, 2008, the disclosures of which are hereby incorporated by reference in their entireties.

This application was made with U.S. government support, including NIH/NCI CA 085069. The U.S. government thus has certain rights in the invention.

BACKGROUND INFORMATION

Barrett's esophagus (BE), a sequela of chronic gastroesophageal reflux disease (GERD), is a highly premalignant condition that increases an individual's chance of developing esophageal adenocarcinoma (EAC) by 30- to 125-fold. Therefore, subjects with BE are usually enrolled in surveillance programs in which they undergo endoscopy at regular intervals for the rest of their lives. However, the incidence of EAC in BE patients under surveillance is only 1/200 patient-years. Conversely, cancers or advanced high-grade dysplasias (HGDs) may develop during the interim and are sometimes missed if surveillance is performed at long intervals. In addition, the current marker of EAC risk in BE, dysplasia, is plagued by high inter-observer variability and limited predictive accuracy. Because neoplastic progression is infrequent in BE, the merits of and appropriate interval for endoscopic surveillance in BE have led to frequent debate. Thus, a means of stratifying patients into groups at high, intermediate, and low risk of neoplastic progression would be highly useful. This process would benefit greatly from effective biomarkers to stratify patients according to their level of neoplastic progression risk.

Methylation constitutes the epigenetic modification of DNA by the addition of methyl groups, usually on cytosines at the sequence 5'-CpG-3'. This event is most relevant when it occurs within CpG islands, which are CpG-rich regions in 5' gene regions of about half of all genes, often involving promoter regions. These islands are normally unmethylated but are vulnerable to de novo methylation, which can silence gene expression. See, e.g., Gardiner-Garden et al. (1987) *J Mol Biol* 196, 261-282 or Takai et al. (2002) *Proc Natl Acad Sci USA* 99, 3740-3745 for discussions of CgG islands. It has been reported that promoter hypermethylation of several tumor suppressor genes is correlated with the incidence of several cancers.

The inventors and their colleagues previously reported that hypermethylation of promoter regions of three genes—cyclin-dependent kinase inhibitor 2a (CDKN2a, or p16), runt-related transcription factor 3 (RUNX3), and transmembrane protein with EGF-like and two follistatin-like domains (HPP1)—occurs early in (BE)-associated neoplastic progression and appears to represent independent risk factors for the progression of Barrett's esophagus (BE) to high-grade dysplasias (HGD) or esophageal adenocarcinoma (EAC). See, e.g., Schulmann et al. (2005) *Oncogene* 24, 4138-4148. Later, the inventors and colleagues developed a tiered risk stratification model to predict progression in BE using epigenetic and clinical features, validating the use of a panel of the three markers (see, e.g., Sato et al. (2008) *PLoS ONE* 3, e1890).

Hypermethylation of these and additional promoter regions might serve as useful biomarkers for stratifying subjects according to their risk for development of EAC or HGD.

DESCRIPTION OF THE DRAWINGS

FIG. 1 shows the genomic sequence of a promoter region of p16, from 1000 nt upstream of the transcriptional start site into exon 1, indicating the start and end sequences of the CpG Island and the transcriptional start site (TSS) (FIG. 1A), and the bisulfite methyl sequence, indicating the locations of the Cg sequences, the TSS, and the locations of the forward and reverse primers and of the probe used in qMSP (FIG. 1B).

FIG. 2 shows the genomic sequence of a promoter region of AKAP12, from 1000 nt upstream of the transcriptional start site into exon 1, indicating the start and end sequences of the CpG Island and the transcriptional start site (TSS) (FIG. 2A), and the bisulfite methyl sequence, indicating the locations of the Cg sequences, the TSS, and the locations of the forward and reverse primers and of the probe used in qMSP (FIG. 2B).

FIG. 3 shows the genomic sequence of a promoter region of CDH13, from 1000 nt upstream of the transcriptional start site into exon 1, indicating the start and end sequences of the CpG Island and the transcriptional start site (TSS) (FIG. 3A), and the bisulfite methyl sequence, indicating the locations of the Cg sequences, the TSS, and the locations of the forward and reverse primers and of the probe used in qMSP (FIG. 3B).

FIG. 4 shows the genomic sequence of a promoter region of HPP1, from 1000 nt upstream of the transcriptional start site into exon 1, indicating the start and end sequences of the CpG Island and the transcriptional start site (TSS) (FIG. 4A), and the bisulfite methyl sequence, indicating the locations of the Cg sequences, the TSS, and the locations of the forward and reverse primers and of the probe used in qMSP (FIG. 4B).

FIG. 5 shows the genomic sequence of a promoter region of NELL1, from 1000 nt upstream of the transcriptional start site into exon 1, indicating the start and end sequences of the CpG Island and the transcriptional start site (TSS) (FIG. 5A), and the bisulfite methyl sequence, indicating the locations of the Cg sequences, the TSS, and the locations of the forward and reverse primers and of the probe used in qMSP (FIG. 5B).

FIG. 6 shows the genomic sequence of a promoter region of RUNX3, from 1000 nt upstream of the transcriptional start site into exon 1, indicating the start and end sequences of the CpG Island and the transcriptional start site (TSS) (FIG. 6A), and the bisulfite methyl sequence, indicating the locations of the Cg sequences, the TSS, and the locations of the forward and reverse primers and of the probe used in qMSP (FIG. 6B).

FIG. 7 shows the genomic sequence of a promoter region of SST, from 1000 nt upstream of the transcriptional start site into exon 1, indicating the start and end sequences of the CpG Island and the transcriptional start site (TSS) (FIG. 7A), and the bisulfite methyl sequence, indicating the locations of the Cg sequences, the TSS, and the locations of the forward and reverse primers and of the probe used in qMSP (FIG. 7B).

FIG. 8 shows the genomic sequence of a promoter region of TAC1, from 1000 nt upstream of the transcriptional start site into exon 1, indicating the start and end sequences of the CpG Island and the transcriptional start site (TSS) (FIG.

8A), and the bisulfite methyl sequence, indicating the locations of the Cg sequences, the TSS, and the locations of the forward and reverse primers and of the probe used in qMSP (FIG. 8B).

Figure 9:
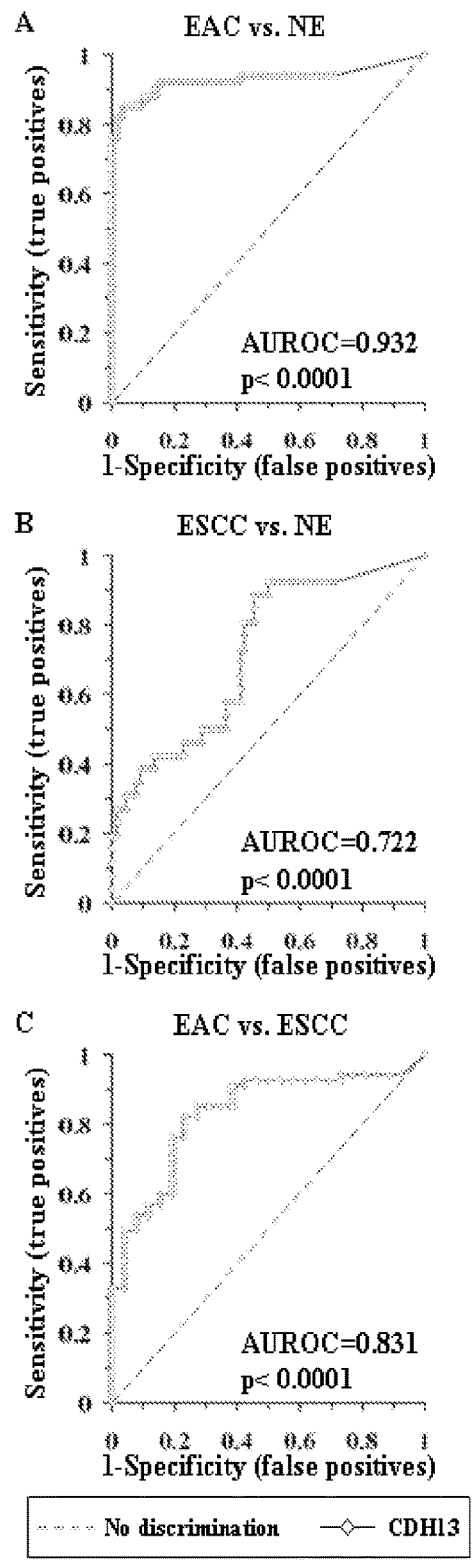

FIG. 9 shows receiver-operator characteristic (ROC) curve analysis of normalized methylation value (NMV). ROC curve analysis of CDH13 NMVs in esophageal adenocarcinoma (EAC) vs. normal esophagus (NE) (FIG. 9A), esophageal squamous cell carcinoma (ESCC) vs. NE (FIG. 9B), and EAC vs. ESCC (FIG. 9C). The high area under the ROC curve (AUROC) conveys the accuracy of this biomarker in distinguishing EAC from NE and from ESCC in terms of its sensitivity and specificity.

Figure 10:
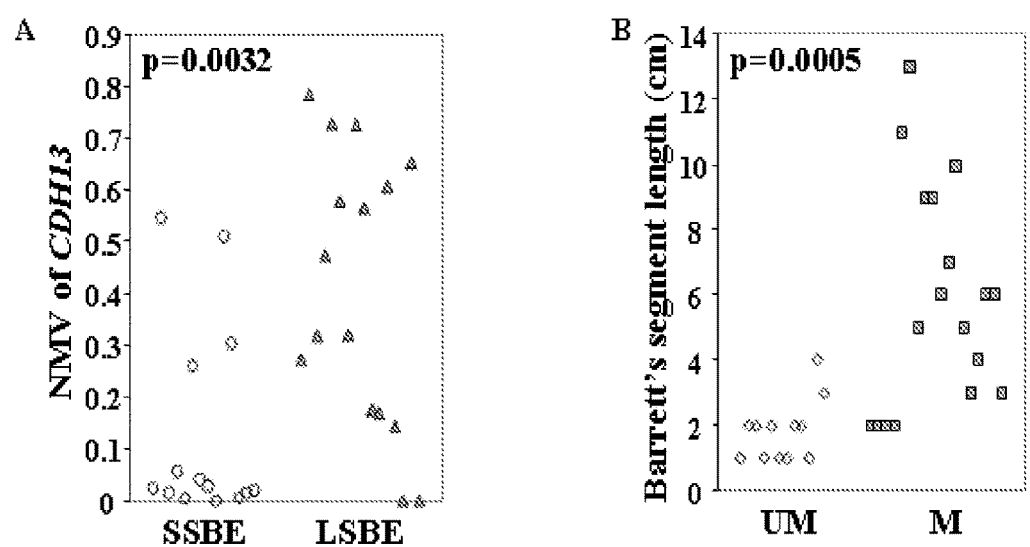

FIG. 10 shows a correlation between Barrett's segment length and CDH13 hypermethylation. FIG. 10A shows that the normalized methylation value (NMV) of CDH13 was significantly higher in long-segment BE (LSBE, mean=0.4071) than in short-segment BE (SSBE, mean=0.131; p=0.0032, Student's t-test). FIG. 10B shows that positive CDH13 hypermethylation status was significantly correlated with BE segment length (p=0.0005, Student's t-test).

Figure 11:
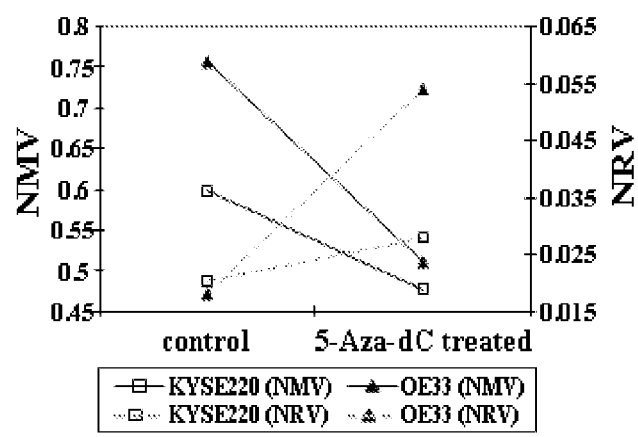

FIG. 11 shows CDH13 methylation level and mRNA expression in esophageal cancer cell lines after treatment with the demethylating agent 5-aza-2'-deoxycytidine (5-Aza-dC). KYSE220 and OE33 EAC cells were subjected to 5-Aza-dC treatment. In both cell lines, after 5-Aza-dC treatment, the NMV of CDH13 was diminished, while the normalized mRNA value (NRV) of CDH13 was increased.

Figure 12:
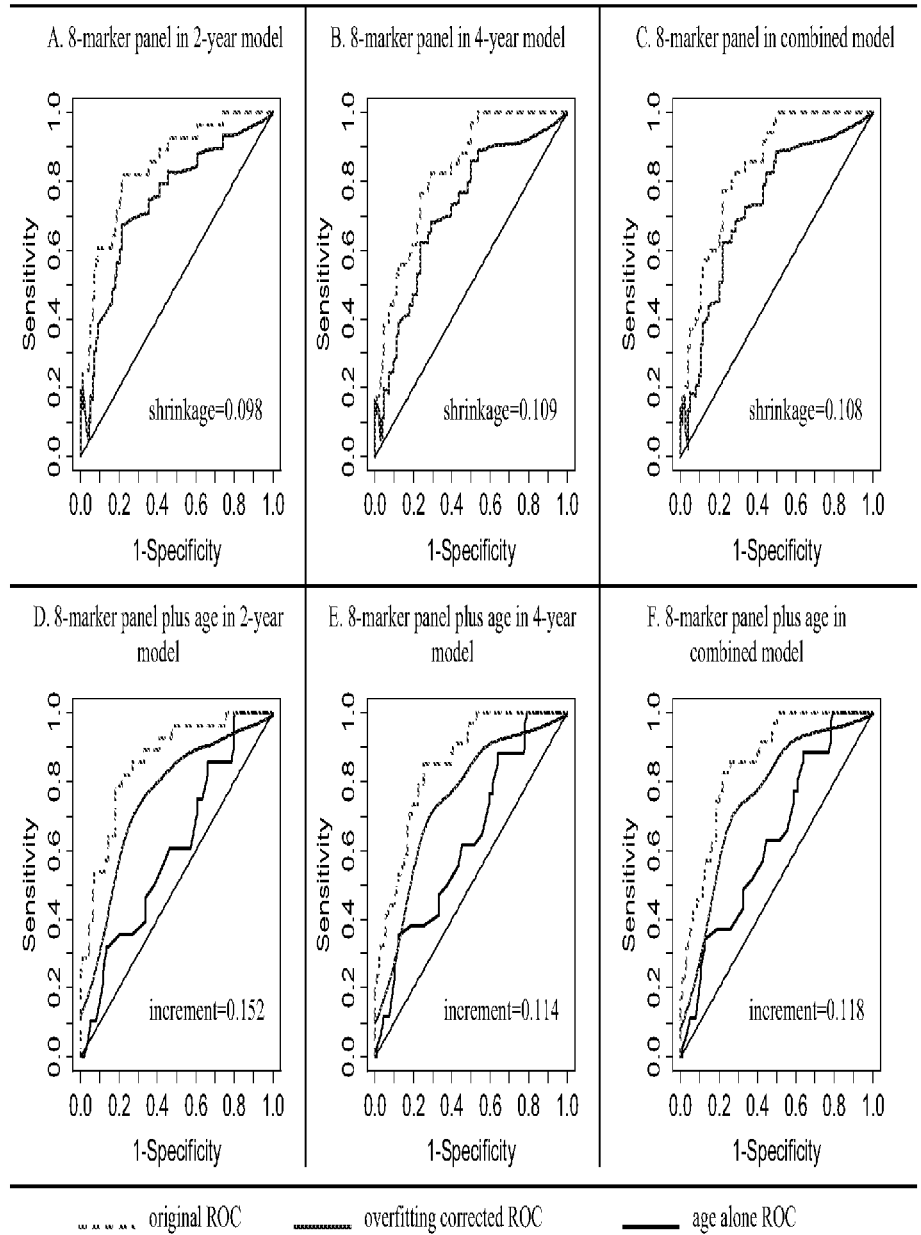

FIG. 12 shows receiver-operator characteristic (ROC) curves for the uncorrected 8-marker and 8-marker-plus-age panels, overfitting-corrected ROC curves for the 8-marker and 8-marker-plus-age panels, and ROC curves for age alone in the 2-, 4-year, and combined prediction models. FIG. 12A shows an uncorrected ROC curve (AUC=0.843) and an overfitting-corrected ROC curve (AUC=0.745) for the 8-marker panel in the 2-year prediction model; shrinkage due to overfitting correction minimal, at 0.098. FIG. 12B shows an uncorrected ROC curve (AUC=0.829) and an overfitting-corrected ROC curve (AUC=0.720) for the 8-marker panel in the 4-year prediction model; shrinkage minimal, at 0.109. FIG. 12C shows an uncorrected ROC curve (AUC=0.840) and an overfitting-corrected ROC curve (AUC=0.732) for the 8-marker panel in the combined prediction model; shrinkage minimal, at 0.108. FIG. 12D shows an uncorrected ROC curve for the 8-marker-plus-age panel (AUC=0.858), overfitting-corrected ROC curve (AUC=0.756), and a ROC curve for age alone (0.604) in the 2-year prediction model; increment over age alone substantial, at 0.152. FIG. 12E shows an uncorrected ROC curve for the 8-marker-plus-age panel (AUC=0.850), an overfitting-corrected ROC curve (AUC=0.744), and a ROC curve for age alone (0.630) in the 4-year prediction model; increment over age alone substantial, at 0.114. FIG. 12F shows an uncorrected ROC curve for the 8-marker-plus-age panel (AUC=0.855), an overfitting-corrected ROC curve (AUC=0.753), and a ROC curve for age alone (0.635) in the combined prediction model; increment over age alone substantial, at 0.118.

FIG. 13 shows risk stratification of BE patients by predictiveness curves of the 8-marker panel, age alone, and the 8-marker-plus-age panel in the combined, 2-year and 4-year prediction models. FIG. 13A shows a predictiveness curve of the 8-marker panel in the combined model. After rigorous overfitting correction, at risk=0.1 and =0.5, 45% and 4% of subjects had estimated risks below 0.1 (LR group) and above 0.5 (HR group), respectively; while the remaining 51% had estimated risks between 0.1 and 0.5 (IR group). FIG. 13B shows predictiveness curves of age alone and of the 8-marker-plus-age panel in the combined model. After rigorous overfitting correction, BE patients were stratified into LR (15%) and IR (85%) groups by age alone. BE patients were stratified into LR (51%), IR (44%) and HR (5%) groups by the 8-marker-plus-age panel. FIG. 13C shows a predictiveness curve of the 8-marker panel in the 2-year model. After rigorous overfitting correction, BE patients were stratified into LR (45%), IR (51%) and HR (4%) groups. FIG. 13D shows predictiveness curves of age alone and of the 8-marker-plus-age panel in the 2-year model. After rigorous overfitting correction, BE patients were stratified into LR (11%) and IR (89%) groups by age alone. BE patients were stratified into LR (52%), IR (44%) and HR (4%) groups by the 8-marker-plus-age panel. FIG. 13E shows a predictiveness curve of the 8-marker panel alone in the 4-year model. After rigorous overfitting correction, BE patients were stratified into LR (44%), IR (51%) and HR (5%) groups. FIG. 13F shows predictiveness curves of age alone and of the 8-marker-plus-age panel in the 4-year model. After rigorous overfitting correction, BE patients were stratified into LR (15%) and IR (85%) groups by age alone. BE patients were stratified into LR (51%), IR (44%) and HR (5%) groups by the 8-marker-plus-age panel. LR: low-risk; IR, intermediate-risk; HR: high-risk; OC: overfitting correction.

Figure 14:
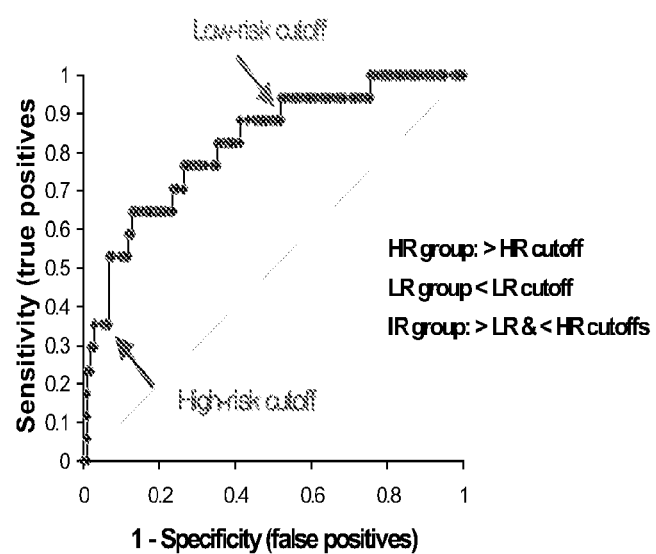

FIG. 14 shows statistical considerations, including cut-off points for Low and High risk.

DESCRIPTION OF THE INVENTION

The inventors extend herein their previous studies identifying hypermethylation of promoter regions of HPP1, p16 and RUNX3 as markers for the development of esophageal adenocarcinoma (EAC) or high-grade dysplasia (HGD), by identifying about 55 additional markers that can be used to predict a subject's risk for developing EAC or HGD. These additional markers include, e.g., hypermethylated promoter regions of nel-like 1 (NELL1), tachykinin-1 (TAC1), somatostatin (SST), A-kinase anchoring protein 12 (AKAP12), cadherin 13, H-cadherin (heart) (CDH13), and of the 50 genes shown in Table 11.

This invention relates, e.g., to a method for predicting a subject's risk for developing (e.g., progressing from BE to) EAC or HGD, comprising (a) determining in a sample from the subject the methylation levels of transcriptional promoter regions of at least two or three of the above-mentioned genes, in various combinations that are elucidated elsewhere herein, and (b) calculating a methylation value (e.g., a methylation index or a linear regression score) that takes into account the methylation levels of the measured transcriptional promoter regions, wherein a methylation value that is below a first predetermined threshold value is indicative that the subject has a low risk of developing EAC or HGD, and a methylation value that is above a second predetermined threshold value is indicative that the subject has a high risk of developing EAC or HGD.

As used herein, a subject that is at "high risk" (or at an "increased risk") for developing EAC or HGD has a greater than 90% likelihood of developing EAC or HGD, within 2 years, 4 years, or ever at all, depending on which model as discussed herein is used. "Low risk" (or a "decreased risk") is defined is defined as a greater than 95% chance that the patient will NOT develop HGD or EAC—within 2 years, 4 years, or ever at all, depending on which model as discussed herein is used.

Advantages of a method of the invention include, e.g., that it is rapid, accurate and inexpensive, and that it can be easily adapted to high throughput format, using automated (e.g., robotic) systems, which allow many measurements to be carried out simultaneously. Furthermore, the methods can be miniaturized. A stratification method of the invention can benefit BE patients in two ways: 1) by decreasing the frequency at which low-risk individuals undergo surveillance endoscopy, thus eliminating unnecessary anxiety, expense, and diminishing procedure-related complications; and 2) by identifying the small group of truly high-risk BE patients for more frequent, intensive surveillance, resulting in earlier and more accurate detection of HGDs and EACs.

One aspect of the invention is a first method for predicting a subject's risk for developing esophageal adenocarcinoma (EAC) or high-grade dysplasia (HGD), comprising
  a) determining in a sample from the subject the methylation levels of transcriptional promoter regions of three or more of the following genes:
    i) CDH13,
    ii) TAC1,
    iii) NELL1,
    iv) AKAP12) or
    v) SST,
and
  b) calculating a methylation value (e.g., a methylation index or a linear regression score) that takes into account the methylation levels of the measured transcriptional promoter regions,
  wherein a methylation value that is below a first predetermined threshold is indicative that the subject has a low risk of developing EAC or HGD, and a methylation value that is above a second predetermined threshold is indicative that the subject has a high risk of developing EAC or HGD.

This first method can further comprise
  a) determining the methylation levels of promoter regions of one or more of
    vi) HPP1,
    vii) p16, or
    viii) RUNX3, and
  b) calculating a methylation value that takes into account the methylation levels of the measured transcriptional promoter regions.

In embodiments of this first method, the methylation levels can be determined for promoter regions of a total of 3, 4, 5, 6, 7 or all 8 of the genes. In another embodiment of this first method, methylation levels for the promoter regions of one or more of the 50 genes listed in Table 11 can also be determined and included in the calculation of the methylation value.

Another aspect of the invention is a second method for predicting a subjects risk for developing esophageal adenocarcinoma (EAC) or high-grade dysplasia (HGD), comprising
  a) determining in a sample from the subject
    the methylation level of a transcriptional promoter region of CDH13, and
    the methylation levels of transcriptional promoter regions of at least two of the following genes:
      i) HPP1
      ii) p16
      iii) RUNX3
      iv) TAC1
      v) NELL1
      vi) AKAP12, or
      vii) SST, and
  b) calculating a methylation value (e.g. a linear regression score or a methylation index) that takes into account the methylation levels of the measured transcriptional promoter regions,
  wherein a methylation value that is below a first predetermined threshold is indicative that the subject has a low risk of developing EAC or HGD, and a methylation value that is above a second predetermined threshold is indicative that the subject has a high risk of developing EAC or HGD.

In embodiments of the this second method, the methylation levels can be determined for promoter regions of a total of 3, 4, 5, 6, 7 or all 8 of the genes; in another embodiment, the methylation levels are measured for CDH13, HPP1, p16 and RUNX3. In another embodiment of this second method, methylation levels for the promoter regions of one or more of the 50 genes listed in Table 11 can also be determined and included in the calculation of the methylation value.

Another aspect of the invention is a third method for predicting a subject's risk for developing esophageal adenocarcinoma (EAC) or high-grade dysplasia (HGD), comprising
  a) determining in a sample from the subject the methylation levels of transcriptional promoter regions of at least two of the genes listed in Table 11, and
  b) calculating a methylation value that takes into account the methylation levels of the measured transcriptional promoter regions,
  wherein a methylation value (e.g. a linear regression score or a methylation index) that is below a first predetermined threshold is indicative that the subject has a low risk of developing EAC or HGD, and a methylation value that is above a second predetermined threshold is indicative that the subject has a high risk of developing EAC or HGD. Any combination of two or more of the genes listed in Table 11 can be used.

Another aspect of the invention is a method for predicting a subject's risk for developing EAC or HGD, comprising
  a) determining in a sample from the subject the methylation levels of transcriptional promoter regions of CDH13, TAC1, NELL1, AKAP12, SST, HPP1, p16, and RUNX3, and
  b) calculating a linear regression score for the 8 methylation levels,
  wherein the methylation levels are determined by qMSP, and
  wherein a linear regression score that is no more than 0.13 is indicative that the subject has a low risk of developing EAC or HGD within 4 years, and a linear regression score that is equal to or above 0.39 is indicative that the subject has an increased risk (e.g., a high risk) of developing EAC or HGD in 4 years.

Another aspect of the invention is a method for predicting a subject's risk for developing EAC or HGD, comprising
  a) determining in a sample from the subject the methylation levels of transcriptional promoter regions of CDH13, TAC1, NELL1, AKAP12, SST, HPP1, p16, and RUNX3, and
  b) calculating a methylation index for the 8 methylation levels,
  wherein the methylation levels are determined by qMSP, and
  wherein a methylation index that is no more than 2 is indicative that the subject has a decreased risk (e.g., a low risk) of developing EAC or HGD in 4 years, and a methylation index that is equal to or above 3 is indicative that the subject has an increased risk (e.g., a high risk) of developing EAC or HGD in 4 years.

In any of the preceding methods, the subject can have, or be suspected of having, BE; the subject can be human; and/or the sample can be a biopsy tissue. Any of a variety of methods can be used to determine the methylation levels, including the quantitative methods: real-time quantitative methylation-specific PCR (qMSP), pyrosequencing, or methylation arrays.

A method of the invention can be performed in conjunction with other assays for EAC, including, e.g., performing conventional histological analysis of the sample (wherein the detection of the presence and degree of dysplasia is further indicative that the subject is at increased risk for developing EAC); determining the age of the subject (wherein if a human subject is more than about 60 years old, this is further indicative that the subject is at risk for developing EAC, and wherein the greater the age of the patient, the higher his or her risk); or determining the BE segment length (wherein a length of 3 cm or greater is further indicative that the subject has a higher risk of developing EAC).

Another aspect of the invention is a method for determining a treatment strategy for a subject (or a method for treating a subject), comprising predicting the subject's risk for developing EAC or HGD and, depending on the assessed risk, deciding how to treat or monitor the subject (or treating or monitoring the subject). For example, if the subject is predicted to be at a decreased risk (e.g. at a low risk) for developing EAC or HGD, but has BE, a decision is made to treat the subject by endoscopic monitoring with endoscopy and biopsies every 2-3 years (e.g., every 3 years); whereas if the subject is predicted to be at an increased risk (e.g. at a high risk) for developing EAC or HGD but has BE, a decision is made to treat the subject by monitoring with endoscopy and biopsies every one year or less.

Another aspect of the invention is a method for following the course of development of EAC in a subject, comprising (a) determining in a sample from the subject, at least two time points, the methylation levels of transcriptional promoter regions of a set of genes as described above, and (b) calculating a methylation value that takes into account the methylation levels of the measured transcriptional promoter regions, wherein an increase in the methylation value between the at least two time points indicates that the EAC has progressed. Any set of time points can be used, e.g., yearly, every other year, etc.

Another aspect of the invention is a method for evaluating a therapeutic method (including, e.g., monitoring the effect of a candidate therapeutic agent), comprising, before and after initiation of the therapy, (a) determining in a sample from the subject the methylation levels of transcriptional promoter regions of a set of genes as described above, and (b) calculating a methylation value that takes into account the methylation levels of the measured transcriptional promoter regions, wherein a decrease in the methylation value following the therapeutic treatment indicates that the treatment has been effective.

Another aspect of the invention is a kit for predicting a subject's risk for developing esophageal adenocarcinoma (EAC) or high-grade dysplasia (HGD), comprising reagents (e.g., suitable primers and probes for determining in a sample from the subject the methylation level of a transcriptional promoter region from the genes or combinations of genes discussed herein, using qMSP; and, optionally, directions for carrying out a method of the invention, containers or packaging materials, and/or a computer program (e.g., a program that calculates a methylation value in a sample based on the determined methylation levels).

In general, a subject to be evaluated by a method of the invention has, or is suspected of having BE. Human patients suspected of having BE often present with heartburn and are subjected to an endoscopy to definitively determine by endoscopy and biopsies for histology whether they have BE and/or dysplasia. Subjects who evince BE, with or without dysplasia, are generally monitored endoscopically periodically, even if symptoms later disappear.

Subjects that can be evaluated by a method of the invention include any of a variety of vertebrates, including, e.g., laboratory animals (e.g., mouse, rat, rabbit, monkey, or guinea pig, in particular mouse or rat models for EAC), farm animals (e.g., cattle, horses, pigs, sheep, goats, etc.), and domestic animals or pets (e.g., cats or dogs). Non-human primates and, preferably, humans, are included.

Suitable samples (e.g., test samples, or control samples) that can be tested by a method of the invention include, e.g., biopsies of esophageal epithelium. For example, the sample can be from grossly apparent BE epithelium or from mass lesions in patients manifesting these changes at endoscopic examination. Methods for obtaining samples and preparing them for analysis are conventional and well-known in the art.

A transcriptional "promoter region," as used herein, refers to a sequence that is at or near the 5' end of an mRNA transcribed from a gene. The region can be, or can be a portion of, a sequence of the genomic DNA comprising (a) at least about 500 (and in some cases, as many as about 1,000 or 2,000) contiguous base pairs (bp) extending upstream of a transcription initiation site, wherein the sequence comprises transcriptional regulatory sequences, such as promoter sequences, and at least a portion of a CpG island; or (b) the transcription initiation site;

(c) at least about 200 bp of the 5' coding sequence of the first exon of a gene, or the entire first exon when the sequence is included in a CpG island; or (d) overlapping sequences thereof.

Although much of the discussion herein is directed to promoter regions that extend no further downstream into a gene than the first exon, recent studies have suggested that hypermethylation of CpG islands that are located much further downstream in a gene, or in intergenic regions, can also silence gene expression. Furthermore, hypermethylation of CpG "shores" that extend as far as 3,000 bp upstream of a transcriptional start site, have also been reported to silence gene expression. See, e.g., Irizarry et al. (2009) *Nat Genet* 41, 178-186. As such more distant CpG islands become identified for the genes identified herein, methylation of those regions can also be assayed by a method of the invention to predict a subjects risk for developing EAC or HGD.

In some embodiments of the invention, a promoter region is selected for analysis which consists of a smaller portion of a larger promoter region as discussed above. For example, if qMSP PCR is used to determine the methylation level, the MSP PCR products are generally designed to be about 80-100 bp long. The actual sequences assayed to determine methylation levels can be the primers (about 18-24 nt) and/or probe (about 18-24 nt). Within each of these about 20-base pieces, there are generally between 2 and 7 CpGs. Annealing of the primers and probes must be "specific," and depends on a complete or near-complete match with the test DNA, with greater fidelity being required at or near the 3' end than at or near the 5' end of the primer or probe.

Technically, the smallest region assayable is about 20 nt. A typical CpG island is about 200 bp long and contains at least 60% of its expected quota of CpGs, which would be 7 CpGs for a 200 bp island. A transcriptional promoter region that is assayed by a method of invention should contain one or more sites associated with methylation, such as CpG dinucleotides, and suitable for quantitative measurement, such as by qMSP.

A skilled worker would know how to select a suitable promoter region to analyze for a gene of interest. For example, sequences can be selected from the large promoter regions that are shown in FIGS. 1-8 for genes HPP1, p16, RUNX3, NELL1, TAC1, SST, AKAP12, and CDH13, and from the large promoter regions of SEQ ID NOs: 50-121. Suitable promoter regions can be selected on the basis of sequences found in searchable databases, such as GenBank or Entrez Gene (NCBI), and the annotations in the records therein regarding the positions of for example, the transcription initiation sites. Such information can also be obtained from a variety of other sources that will be evident to a skilled worker. See, for example, the discussion in Example IV.

Sequences of promoter regions shown herein and in searchable databases are sometimes presented as just one strand of a DNA double helix. Because the PCR-amplified DNA in a test sample is double-stranded, a probe of the invention can bind to one of the two DNA strands of the double-stranded DNA, and is completely complementary to the other strand. Which of the two strands is being described is not always indicated in the discussion herein; but it will be evident to a skilled worker whether a given probe binds to one of the DNA strands of an amplicon, or to its complete complement.

A "methylation level," as used herein, is a function of the method used to measure this value. In the experiments shown herein, the measurement is accomplished with qMSP. Using this method, a methylation level is the quantitative measurement of methylated DNA for a gene promoter region, defined by the percentage of DNA in the sample that is methylated at each MSP primer/promoter location. This can range from 0 to 100%. In general, but not invariably, most of the CpGs in a given CpG island are methylated. If other methods are used to measure the methylation level, such as pyrosequencing or bisulfite sequencing, the measurement can reflect a quantitative measurement of the number of methylated cytosines in CpG islands (or CpG dinucleotides) in a promoter region from a gene of interest.

It is generally desirable to measure a methylation level in relation to a normalization standard or a reference value. In Example II herein, actin is used as an internal control to determine how much DNA is methylated, and the methylation levels are referred to as NMVs (normalized methylation values). The amount of actin is measured by PCR rather than MSP, because the primers/probes for actin contain no methylatable sequences (i.e., there are no CpGs in the sequences). Other suitable normalization controls, including other constitutive genes or genes whose sequences which are methylated to a known degree, will be evident to a skilled worker.

In establishing that the eight markers for which qMSP studies are reported herein are strongly predictive, the inventors compared the methylation levels of the markers to baseline values in normal tissues. ROC curves for normal tissue vs. Barrett's and normal tissue vs. tumor are shown in the Examples herein; these ROC curves had very large areas (AUROCs) under them, indicating values ranging from 0.622 to 0.845.

These eight markers were selected for the panel, at least in part, because they are not methylated in normal tissues of normal subjects. That is, the mean methylation level for one of these markers in a normal population would be zero. Therefore, an assay using these eight markers does not require a comparison to normal subjects. This is an advantage of using these eight markers. A "normal" subject, as used herein, is one who does not have detectable neoplasia or metaplasia of the esophagus and therefore is not expected to develop BE or EAC. In general, a level associated with a "normal" subject includes a statistically obtained value associated with a population of normal subjects. For example, a methylation level in a normal subject includes the mean or average methylation level in a substantial population of subjects.

For other markers, such as the promoter regions of some of the 50 genes listed in Table 11, there may be some degree of methylation of the markers in normal subjects. In those cases, the methylation level is compared to the level in a comparable region from a normal subject or population of subjects, such as from the same promoter region from a matched tissue. Suitable comparisons can be made to levels in normal white blood cells (WBCs) and/or normal esophagus, from normal and/or diseased subjects.

In some embodiments, it is desirable to express the results of an assay in terms of a statistically significant increase in a value compared to a baseline value. A "significant" increase or decrease in a value, as used herein, can refer to a difference which is reproducible or statistically significant, as determined using statistical methods that are appropriate and well-known in the art, generally with a probability value of less than five percent chance of the change being due to random variation. Some such statistical tests are discussed herein; others will be evident to a skilled worker.

It will be appreciated by those of skill in the art that a baseline or normal level need not be established for each assay as the assay is performed but rather, baseline or normal levels can be established by referring to a form of stored information regarding a previously determined baseline methylation levels for a given gene or panel of genes, such as a baseline level established by any of the above-described methods. Such a form of stored information can include, for example, a reference chart, listing or electronic file of population or individual data regarding "normal levels" (negative control) or polyp positive (including staged tumors) levels; a medical chart for the patient recording data from previous evaluations; a receiver-operator characteristic (ROC) curve; or any other source of data regarding baseline methylation levels that is useful for the patient to be diagnosed.

A "methylation value," as used herein, is a quantitative value that takes into account the methylation levels of all of the markers tested in a particular assay, and weighs the contributions of the levels appropriately. A methylation value can be calculated in several ways, which will be evident to a skilled worker. These include, e.g., a linear regression score from the linear regression of all of the markers in a panel (e.g., the panel of eight markers described in Example III), or a "methylation index."

In one embodiment of the invention, the methylation value is expressed as a linear regression score, as described, e.g., in Irwin, in Neter, Kutner, Nachtsteim, Wasserman (1996) Applied Linear Statistical Models, $4^{th}$ edition, page 295. See also the Examples herein. Typical regression scores are indicated in Table 1, for both an 8-marker panel (using all 8 of the markers discussed herein) and a 3-marker panel with the promoter regions of HPP1, p16 and RUNX3.

TABLE 1

| | \multicolumn{5}{c}{8-marker panel:} |
|---|---|---|---|---|---|
| | Specificity (95% CI) @ sensitivity | | | Sensitivity (95% CI) @ specificity | |
| | 0.95 | 0.9 | 0.8 | 0.9 | 0.8 |
| Combined model | | | | | |
| Age | 0.219 (0.125, 0.370) | 0.260 (0.162, 0.425) | 0.390 (0.240, 0.508) | 0.221 (0.054, 0.448) | 0.371 (0.204, 0.532) |
| Marker panel | 0.527 (0.292, 0.730) | 0.567 (0.413, 0.849) | 0.724 (0.574, 0.914) | 0.443 (0.350, 0.838) | 0.629 (0.527, 0.941) |
| Marker panel + age | 0.515 (0.352, 0.779) | 0.576 (0.484, 0.867) | 0.781 (0.647, 0.944) | 0.457 (0.372, 0.869) | 0.757 (0.598, 0.964) |
| 2-year model | | | | | |
| Age | 0.205 (0.106, 0.324) | 0.205 (0.138, 0.389) | 0.351 (0.197, 0.484) | 0.176 (0.021, 0.426) | 0.354 (0.172, 0.538) |
| Marker panel | 0.383 (0.288, 0.794) | 0.547 (0.436, 0.873) | 0.757 (0.595, 0.935) | 0.607 (0.393, 0.870) | 0.721 (0.593, 0.969) |
| Marker panel + age | 0.454 (0.334, 0.833) | 0.615 (0.474, 0.918) | 0.786 (0.652, 0.956) | 0.536 (0.400, 0.934) | 0.786 (0.600, 0.987) |
| 4-year model | | | | | |
| Age | 0.217 (0.120, 0.366) | 0.249 (0.158, 0.430) | 0.384 (0.229, 0.506) | 0.232 (0.038, 0.467) | 0.382 (0.214, 0.541) |
| Marker panel | 0.494 (0.273, 0.746) | 0.523 (0.426, 0.835) | 0.704 (0.579, 0.909) | 0.465 (0.346, 0.814) | 0.606 (0.545, 0.941) |
| Marker panel + age | 0.507 (0.359, 0.780) | 0.574 (0.488, 0.864) | 0.757 (0.649, 0.940) | 0.450 (0.385, 0.885) | 0.724 (0.600, 0.963) |

| | Linear score @ sensitivity | | | Linear score @ specificity | |
|---|---|---|---|---|---|
| | 0.95 | 0.9 | 0.8 | 0.9 | 0.8 |
| Combined model | | | | | |
| Age | 0.135 | 0.154 | 0.201 | 0.365 | 0.319 |
| Marker panel | 0.147 | 0.159 | 0.224 | 0.395 | 0.253 |
| Marker panel + age | 0.112 | 0.136 | 0.276 | 0.443 | 0.297 |
| 2-year model | | | | | |
| Age | 0.122 | 0.125 | 0.166 | 0.280 | 0.250 |
| Marker panel | 0.073 | 0.110 | 0.178 | 0.307 | 0.202 |
| Marker panel + age | 0.063 | 0.107 | 0.220 | 0.356 | 0.232 |
| 4-year model | | | | | |
| Age | 0.133 | 0.148 | 0.195 | 0.352 | 0.308 |
| Marker panel | 0.130 | 0.141 | 0.209 | 0.391 | 0.254 |
| Marker panel + age | 0.105 | 0.131 | 0.235 | 0.431 | 0.290 |

| | \multicolumn{5}{c}{3-marker panel:} |
|---|---|---|---|---|---|
| | Specificity (95% CI) @ sensitivity | | | Sensitivity (95% CI) @ specificity | |
| | 0.95 | 0.9 | 0.8 | 0.9 | 0.8 |
| Combined model | | | | | |
| Age | 0.233 (0.146, 0.417) | 0.353 (0.194, 0.489) | 0.463 (0.342, 0.598) | 0.340 (0.130, 0.498) | 0.400 (0.261, 0.570) |
| Marker panel | 0.076 (0, 0.352) | 0.252 (0.006, 0.464) | 0.408 (0.175, 0.604) | 0.289 (0.156, 0.482) | 0.358 (0.286, 0.630) |
| Marker panel + age | 0.213 (0.111, 0.469) | 0.410 (0.169, 0.566) | 0.482 (0.356, 0.715) | 0.378 (0.222, 0.596) | 0.578 (0.373, 0.741) |
| 2-year model | | | | | |
| Age | 0.213 (0.122, 0.351) | 0.248 (0.164, 0.445) | 0.401 (0.242, 0.573) | 0.326 (0.121, 0.524) | 0.412 (0.250, 0.588) |
| Marker panel | 0.028 (0.001, 0.316) | 0.214 (0.022, 0.461) | 0.403 (0.148, 0.641) | 0.265 (0.132, 0.500) | 0.476 (0.265, 0.676) |
| Marker panel + age | 0.166 (0.072, 0.416) | 0.267 (0.125, 0.555) | 0.432 (0.241, 0.753) | 0.382 (0.212, 0.620) | 0.606 (0.344, 0.772) |

TABLE 1-continued

| | | | | | |
|---|---|---|---|---|---|
| 4-year model | | | | | |
| Age | 0.227 (0.142, 0.389) | 0.323 (0.189, 0.466) | 0.440 (0.303, 0.573) | 0.377 (0.153, 0.524) | 0.429 (0.286, 0.582) |
| Marker panel | 0.147 (0, 0.374) | 0.265 (0.027, 0.476) | 0.419 (0.225, 0.606) | 0.310 (0.162, 0.485) | 0.381 (0.286, 0.625) |
| Marker panel + age | 0.188 (0.098, 0.440) | 0.368 (0.150, 0.534) | 0.449 (0.315, 0.741) | 0.379 (0.237, 0.591) | 0.619 (0.389, 0.756) |

| | Linear score @ sensitivity | | | Linear score @ specificity | |
|---|---|---|---|---|---|
| | 0.95 | 0.9 | 0.8 | 0.9 | 0.8 |
| Combined model | | | | | |
| Age | 0.097 | 0.149 | 0.207 | 0.386 | 0.335 |
| Marker panel | 0.174 | 0.182 | 0.192 | 0.309 | 0.271 |
| Marker panel + age | 0.088 | 0.166 | 0.197 | 0.374 | 0.317 |
| 2-year model | | | | | |
| Age | 0.081 | 0.093 | 0.142 | 0.294 | 0.252 |
| Marker panel | 0.126 | 0.139 | 0.148 | 0.232 | 0.198 |
| Marker panel + age | 0.064 | 0.095 | 0.143 | 0.277 | 0.239 |
| 4-year model | | | | | |
| Age | 0.092 | 0.131 | 0.183 | 0.356 | 0.309 |
| Marker panel | 0.156 | 0.163 | 0.174 | 0.301 | 0.252 |
| Marker panel + age | 0.072 | 0.141 | 0.171 | 0.353 | 0.298 |

When the methylation value is expressed in this manner, the cut-off values to determine that a subject is at low risk or at high risk for developing EAC or HGD can be determined from the linear scores in Table 1. For the low-risk cut-off, a very high sensitivity (e.g., 95%) is desirable, so the cut-off value (threshold value) for the 8-marker panel is about 0.147 for the combined model, about 0.073 for the 2-year model, or about 0.130 for the 4-year model. For the high-risk cut-off, a high specificity (e.g., 90%) is desirable, so that the cutoff (score) is about 0.395 for the combined model, about 0.307 for the 2-year panel, and about 0.391 for the 4-year model. The values for a panel of fewer markers would vary accordingly. See, e.g, the values in Table 1 for the 3-marker panel. The cut-off values would likely differ if different genes were integrated into the model; suitable cut-off values can be determined without undue experimentation by a skilled worker. The term "about" a number, as used herein, refers to any value within 20% of the number.

In another embodiment of the invention, the methylation value is expressed as a "methylation index." A methylation index (MI) is defined as the number of genes which demonstrated an altered methylation level (i.e., which exceed or fall below a previously determined methylation level cutoff) within a defined set of genes. For example, if there are four genes in a defined gene set and none of these four genes is methylated, the MI equals 0; if any one of the four are methylated, the MI equals 1; if any two of the four are methylated, the MI equals 2; if any three of the four are methylated, the MI equals 3; and if all four of these four genes are methylated, the MI equals 4 (i.e., the maximum possible MI for this gene set).

When the methylation value is expressed in terms of a MI, the cut-off values to determine that a subject is at low risk or at high risk for developing EAC or HGD can be the optimal point (the value closest to the origin) on the ROC curve of normal vs. EAC. In one embodiment of the invention, in which the 8-marker panel is used, a methylation index of at most about two is indicative that the subject has a low risk of developing EAC or HGD, and a methylation index of equal to or greater than about three is indicative that the subject is at high risk for developing EAC or HGD. The cut-off values will be a function of the number of markers in a panel. For example, for a panel or 50 markers, the cut-off values would be less than 12 or equal to or greater than 13. The actual cut-off values for any given panel of markers can be determined readily by a skilled worker, using routine methods, e.g., as described herein.

The difference between the methylation level of a test subject and normal methylation levels may be a relative or absolute quantity. Thus, "methylation level" is used to denote any measure of the quantity of methylation of the gene or panel of genes. The level of methylation may be either abnormally high, or abnormally low, relative to a defined high or low threshold value determined to be normal for a particular group of subjects. The difference in level of methylation between a subject and the reference methylation level may be equal to zero, indicating that the subject is or may be normal, or that there has been no change in levels of methylation since the previous assay.

The methylation levels and any differences that can be detected may simply be, for example, a measured fluorescent value, radiometric value, densitometric value, mass value etc., without any additional measurements or manipulations. Alternatively, the levels or differences may be expressed as a percentage or ratio of the measured value of the methylation levels to a measured value of another compound including, but not limited to, a standard or internal DNA standard, such as beta-actin. This percentage or ratio may be abnormally low, i.e., falling below a previously defined normal threshold methylation level; or this percentage or ratio may be abnormally high, i.e., exceeding a previously defined normal threshold methylation level. For example, this can be the optimal point on the ROC curve. The difference may be negative, indicating a decrease in the amount of measured levels over normal value or from a previous measurement, and the difference may be positive, indicating an increase in the amount of measured methylation levels over normal values or from a previous measurement. The difference may also be expressed as a difference or ratio of the methylation levels to itself, measured at a different point in time. The difference may also be determined using in an algorithm, wherein the raw data are manipulated.

The following paragraphs describe some of the considerations concerning refining suitable cut-off points, using a proposed, even larger study than the one presented herein:

For the 2- or 4-year models, sensitivity connotes the fraction of subjects testing positive among these who progressed to HGD or EAC within 2 or 4 years of marker measurement; while for the combined model, it is the fraction of subjects testing positive among those who ever progressed to HGD or EAC within the observation window. Similarly, specificity is the fraction of subjects testing negative among those who did not progress to HGD or EAC within 2 or 4 years (for the 2- or 4-year models). The following null ($H_0$) and alternative ($H_1$) hypotheses will be tested in choosing 2 threshold values to define the 3 risk groups (i.e., high-, intermediate-, and low-risk groups) from a single ROC curve.

High-risk Cutoff:
$H_0$: Sensitivity$_0$<=0.30 (at Specificity$_0$=0.90)
$H_1$: Sensitivity$_1$>0.30 (=0.45) (at Specificity$_1$=0.90)
(corresponding to PPV$_0$=0.32 vs. PPV$_1$=0.41 with progression rate 0.135, or
(corresponding to PPV$_0$=0.20 vs. PPV$_1$=0.27 with progression rate 0.075)

That is, we maximize specificity at the expense of sensitivity in choosing the high-risk cutoff value, reasoning that the FPC or false-positive cost (unnecessary endoscopies in patients who would not otherwise have been endoscoped) outweighs the FNC or false-negative cost (failure to diagnose/predict 60% of cases in a low-prevalence population [13.5% over the duration of the study]). A sensitivity of 0.30 at a specificity of 0.90 is considered minimally clinically acceptable, and we anticipate that our markers will have sensitivity of 0.45 at this specificity value. Our PPV at alternative of 0.41 (alternative hypothesis) greatly exceeds this population prevalence. Thus, any true positives detected (predicted) will represent gains in early diagnosis and can be considered a significant gain, whereas missed diagnoses (predictions) would have been missed anyway under the current standard endoscopic surveillance interval of 2-3 years.

Low-risk Cutoff:
$H_0$: Specificity$_0$<=0.30 (@ Sensitivity$_0$=0.95)
$H_1$: Specificity$_1$>0.30 (=0.50) (@ Sensitivity$_1$=0.95)
(corresponding to NPV$_0$=0.98 vs. NPV$_1$=0.99 with progression rate 0.135)
(corresponding to NPV$_0$=0.987 vs. NPV$_1$=0.992 with progression rate 0.075)

For the low-risk cutoff, we must minimize FNC (failure to diagnose HGD or cancer) because these cases would have been diagnosed under the current standard surveillance interval of 2-3 years, thus if we lengthen it to 4-6 years, we must be certain that we fail to predict as few progressors as possible. That is, a high FNC is not acceptable. Conversely, a high FPC is acceptable for the low-risk group cutoff value, because in current clinical practice, 100% of this group would have been endoscoped at 2-3-year intervals. Thus, any reduction below 100% in this group can be considered a significant gain because it represents a savings of unnecessary surveillance endoscopies. In this case we consider a specificity at 0.30 given a sensitivity of 0.95 is minimally clinically acceptable, and we anticipate that our markers will have a specificity of 0.5 at this sensitivity.

Any of a variety of methods can be used to determine (measure) methylation levels. In one embodiment of the invention, quantitative methods are used, such as, e.g., real-time quantitative methylation-specific PCR (qMSP), pyrosequencing, or methylation microarrays (using, e.g., the Human CpG Island Microarrays and/or methylation system sold by Agilent Technologies, Santa Clara, Calif. and/or methods as described in Beier et al. (2007) *Adv Biochem Eng Biotechnol* 104, 1-11). A "methylation array," as used herein, refers to an array of probes that can be used to distinguish between methylated and unmethylated DNA (e.g., between cytosines that are, or are not, methylated).

In other embodiments of the invention (e.g., to determine if a subject has BE or EAC, but not necessarily to determine the course of development of the condition or to stratify subjects into different risk groups), non-quantitative measurement methods can be used. These include, e.g., assays based on methylated DNA immunoprecipitation, using a monoclonal antibody against 5-methylcytosine (see, e.g., Weber et al. (2005) *Nat Genet* 37, 853-862); Southern blotting analysis using a methylation-sensitive restriction enzyme; single nucletotide primer extension (SNuPE—Gonzalgo et al. (1997) *Nuc Acids Res* 25, 2532-2534); restriction landmark genomic scanning for methylation (RLGS-M); or combined bisulfite restriction analysis (COBRA—see, e.g., Xiong et al. (1997) *Nuc Acids Res* 25, 2532-2534).

Real-time polymerase chain reactions (PCR), such as quantitative real-time PCR, can be employed in many of the assays described herein. Such assays are well-known in the art and can be practiced generally according to the known methods. See for example, Heid et al. (1996) *Genome Res.* 6, 986-994. Briefly, a sequence of interest (e.g., from a promoter region of the invention) is PCR amplified, using a forward PCR primer and a reverse PCR primer, in the presence of a fluorogenic probe that can distinguish between a methylated and a non-methylated version of the amplified sequence.

For quantitative methylation-specific real-time PCR (qMSP), the target DNA is pretreated before PCR amplification with an agent, such as bisulfite, that converts methylated cytosines (C's) to uracils (U's). The fluorogenic probe is designed to recognize a sequence in which methylated C's have been converted to U's by this procedure (or, if a control is required, to recognize a sequence in which C's are present in those positions). The qMSP assay is designed such that the labeling moieties on the 5' and/or 3' ends of the fluorogenic probe do not fluoresce unless PCR amplification of the sequence to which the probe binds has occurred, followed by hybridization of the probe to the amplified sequences, in which case fluorescence of the probe can be seen. The labeling moieties on both ends of a probe are fluorescent molecules, which quench one another. For simplicity, the labeling moiety on one end (e.g., the 5' end) is sometimes referred to as a "fluorophore," and the labeling moiety on the other end (e.g., the 3' end) as a "quencher." When a single stranded probe is not hybridized to a target and is free in solution, the probe molecule is flexible and folds back partially on itself, so that the quencher and the fluorophore are close together; the quencher thus prevents the probe from fluorescing. Furthermore, when a probe of the invention is hybridized to a single-stranded target, the two labeling moieties are close enough to one another to quench each other. However, without wishing to be bound by any particular mechanism, it is suggested that when the probe is hybridized to its target to form a perfect double stranded DNA molecule, a 5' to 3' exonuclease which recognizes perfect hybrids, and which is an activity of the enzyme used for PCR, cleaves the duplex, releasing the fluorophore. The fluorophore is thus separated from the quencher, and will fluoresce. The amount of detected fluorescence is proportional to the amount of amplified DNA.

In a real time PCR, the released fluorescent emission is measured continuously during the exponential phase of the PCR amplification reaction. Since the exponential accumulation of the fluorescent signal directly reflects the exponential accumulation of the PCR amplification product, this reaction is monitored in real time ("real time PCR"). Oligonucleotides used as amplification primers (e.g., DNA, RNA, PNA, LNA, or derivatives thereof) preferably do not have self-complementary sequences or have complementary sequences at their 3' end (to prevent primer-dimer formation). Preferably, the primers have a GC content of about 50% and may contain restriction sites to facilitate cloning Amplification primers can be between about 10 and about 100 nt in length. They are generally at least about 15 nucleotides (e.g., at least about 15, 20, or 25 nt), but may range from about 10 to a full-length sequence, and not longer than 50 nt. In some circumstances and conditions, shorter or longer lengths can be used Amplification primers can be purchased commercially from a variety of sources, or can be chemically synthesized, using conventional procedures. Suitable primers can be readily designed by conventional methods, such as inspection of known sequences of promoter regions of interest or by use of computer programs such as ClustalW from the European Bioinformatics Institute (world wide web site ebi.ac.uk/clustalw.htm). Some exemplary PCR primers are described in the Examples.

In one embodiment of the invention, rather than, or in addition to, using a fluorogenic probe that can distinguish between methylated and unmethylated cytosines, one of both of the PCR primers are designed so as to distinguish between such sequences.

Probes and conditions can be selected, using routine conventional procedures, to insure that hybridization of a probe to a sequence of interest is specific. A probe that is "specific for" a nucleic acid sequence (e.g., in a DNA molecule) contains sequences that are substantially similar to (e.g., hybridize under conditions of high stringency to) sequences in one of the strands of the nucleic acid. By hybridizing "specifically" is meant herein that the two components (the target DNA and the probe) bind selectively to each other and not generally to other components unintended for binding to the subject components. The parameters required to achieve specific binding can be determined routinely, using conventional methods in the art. A probe that binds (hybridizes) specifically to a target of interest does not necessarily have to be completely complementary to it. For example, a probe can be at least about 95% identical to the target, provided that the probe binds specifically to the target under defined hybridization conditions, such a conditions of high stringency.

As used herein, "conditions of high stringency" or "high stringent hybridization conditions" means any conditions in which hybridization will occur when there is at least about 85%, e.g., 90%, 95%, or 97 to 100%, nucleotide complementarity (identity) between a nucleic acid of interest and a probe. Generally, high stringency conditions are selected to be about 5° C. to 20° C. lower than the thermal melting point ($T_m$) for the specific sequence at a defined ionic strength and pH. Hybridization as used according to the present invention, refers to hybridization under standard conditions used for real-time PCR to achieve amplification.

The size of a probe used to detect the methylation level of a promoter region will vary according to a variety of factors, including, e.g., the ease of preparing (e.g., synthesizing) the probe, the assay method employed to determine the methylation level, etc.

Methods for labeling probes with fluorophores are conventional and well-known. Suitable fluorescer-quencher dye sets will be evident to the skilled worker. Some examples are described, e.g., in Holland et al. (1991) *Proc. Natl. Acad. Sci.* 88, 7276-7280; WO 95/21266; Lee et al. (1993) *Nucleic Acids Research* 21, 3761-3766; Livak et al. (1995), supra; U.S. Pat. No. 4,855,225 (Fung et al); U.S. Pat. No. 5,188,934 (Menchen et al.); PCT/US90/05565 (Bergot et al.), and others.

The fluorogenic probes described in the Examples herein function by means of FRET (fluorescence resonance energy transfer). The FRET technique utilizes molecules having a combination of fluorescent labels which, when in proximity to one another, allows for the transfer of energy between labels. See, e.g., the Examples herein or "iQ5 Real Time PCR Detection System" Manual (Bio-Rad, Hercules, Calif.). Other well-known methods for the detection of real-time PCR will be evident to a skilled worker. For example, molecular beacons can be used.

Methods of PCR amplification (including qMSP), and reagents used therein, as well as methods for detecting emission spectra, are conventional. For guidance concerning PCR reactions, see, e.g., PCR Protocols: A Guide to Methods and Applications (Innis et al. eds, Academic Press Inc. San Diego, Calif. (1990)). These and other molecular biology methods used in methods of the invention are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

An assay of the invention can be performed in conjunction with one or more other diagnostic (predictive) methods, based, for example, on genomic information, proteomic information, histological analysis of tissue sample, or other methods known in the art. Suitable methods include, e.g., detecting low-grade or high-grade dysplasia (wherein the presence of high-grade dysplasia is further indicative that the subject has an increased risk of developing EAC); taking into consideration the age of the subject (wherein a human subject that is more than 60 years old has an increased risk of developing EAC, and wherein the older the subject, the greater the risk); or determining BE segment length (wherein a length of at least 3 cm in length is further indicative that the subject has a high risk of developing EAC, and wherein the longer the BE segment, the greater the risk).

One aspect of the invention is a kit for predicting a subjects risk for developing EAC or HGD. A skilled worker will recognize components of kits suitable for carrying out a method of the invention. The agents in the kit can encompass reagents for carrying out a method of the invention (e.g., primers and probes for qMSP of sets of promoter regions of the invention). The kit may also include additional agents suitable for detecting, measuring and/or quantitating the amount of PCR amplification.

Optionally, a kit of the invention may comprise instructions for performing the method. Optional elements of a kit of the invention include suitable buffers, control reagents, containers, or packaging materials. The reagents of the kit may be in containers in which the reagents are stable, e.g., in lyophilized form or stabilized liquids. The reagents may also be in single use form, e.g., for the performance of an assay for a single subject.

Kits of the invention may comprise one or more computer programs that may be used in practicing the methods of the invention. For example, a computer program may be provided that calculates a methylation value in a sample from results of the determining methylation levels. Such a computer program may be compatible with commercially available equipment, for example, with commercially available microarray or real-time PCR. Programs of the invention may take the output from microplate reader or realtime-PCR gels or readouts and prepare a calibration curve from the optical density observed in the wells, capillaries, or gels and compare these densitometric or other quantitative readings to the optical density or other quantitative readings in wells, capillaries, or gels with test samples.

In addition to the clinical uses discussed herein, kits of the invention can be used for experimental applications.

In the foregoing and in the following examples, all temperatures are set forth in uncorrected degrees Celsius; and, unless otherwise indicated, all parts and percentages are by weight.

EXAMPLES

Example I

Studies of Methylation Levels and Frequencies of Nel-like 1 (NELL1), Tachykinin-1 (TAC1), Somatostatin (SST), and A-kinase Anchoring Protein 12 (AKAP12)

Methylation levels and frequencies of the above genes were studied, using real-time quantitative methylation-specific PCR (qMSP), in 259 endoscopic esophageal biopsy specimens of differing histologies. Prevalences were determined in each of the following histological categories: NE, BE, LGD, HGD or EAC. The methods used in these studies are, in general, similar or identical to those described in Example II. For details of these studies, see, e.g., the following references, all of which are incorporated by reference herein in their entirety: Jin et al. (2007) *Oncogene* 26, 6332-6340; Jin et al. (2007) *Clin Cancer Res* 13, 6293-6300; Jin et al. (2008) *Cancer* 112, 43-49; Jin et al. (2008) *Cancer* 112, 43-49; and Jin et al. (2008) *Cancer Epidemiol Biomarkers Prev* 17, 111-117. Among 10 genes evaluated, the five genes noted above were methylated early and often in BE-associated neoplastic progression.

Example II

Promoter Hypermethylation of CDH13 is a Common, Early Event in Human Esophageal Adenocarcinogenesis and Correlates with Clinical Risk Factors CDH13 (also known as H-cadherin and T-cadherin), a member of the cadherin gene superfamily, was isolated and has been mapped to 16q24, a locus that frequently undergoes deletion in human cancers, including esophageal carcinoma. In contrast to other known cadherins such as E-cadherin, N-cadherin, and P-cadherin, which are transmembrane proteins, CDH13 lacks conventional transmembrane and cytoplasmic domains and is attached to the plasma membrane through a glycosyl phosphatidyl inositol anchor. Several studies have suggested that CDH13 functions as a tumor suppressor gene and possesses potent antitumor activity in several human cancers both in vitro and in vivo. Hypermethylation of CDH13 has been described in many human cancers, including ESCC. Prior to the present studies, however, hypermethylation of CDH13 in precancerous lesions such as Barrett's metaplasia (BE), as well as in BE-associated EAC, is an area that had not been explored.

This Example describes studies of hypermethylation of the promoter region of CDH13 in Barrett's-associated esophageal adenocarcinogenesis. 259 human esophageal tissues were examined for CDH13 promoter hypermethylation by real-time methylation-specific PCR. CDH13 hypermethylation showed discriminative receiver-operator characteristic curve profiles, sharply demarcating esophageal adenocarcinoma (EAC) from esophageal squamous cell carcinoma (ESCC) and normal esophagus (NE) ($p<0.0001$). CDH13 normalized methylation values (NMV) were significantly higher in Barrett's esophagus (BE), dysplastic BE (D), and EAC than in NE ($p<0.0000001$). CDH13 hypermethylation frequency was 0% in NE but increased early during neoplastic progression, rising to 70% in BE, 77.5% in D, and 76.1% in EAC. Both CDH13 hypermethylation frequency and its mean NMV were significantly higher in BE with than without accompanying EAC. In contrast, only five (19.2%) of 26 ESCCs exhibited CDH13 hypermethylation. Furthermore, both CDH13 hypermethylation frequency and its mean NMV were significantly higher in EAC than in ESCC, as well as in BE or D vs. ESCC. Interestingly, mean CDH13 NMV was significantly lower in short-segment than in long-segment BE, a known clinical risk factor for neoplastic progression. Similarly, BE segment length was significantly lower in specimens with unmethylated than with methylated CDH13 promoters. 5-aza-2'-deoxycytidine treatment of OE33 EAC and KYSE220 ESCC cells reduced CDH13 methylation and increased CDH13 mRNA expression. Our results reveal that promoter hypermethylation of CDH13 is a common event in EAC but not in ESCC and occurs early during BE-associated esophageal neoplastic progression, correlating with clinical criteria associated with neoplastic progression risk.

A. Materials and Methods (1) Tissue samples. The 259 specimens examined in the current study comprised 66 from normal esophagus (NE), 60 of non-dysplastic Barrett's metaplasia {BE, including 36 obtained from patients with BE alone (Ba) and 24 from patients with BE accompanied by EAC (Bt)}, 40 from dysplastic BE {D, including 19 low-grade (LGD) and 21 high-grade (HGD)}, 67 EACs, and 26 ESCCs. All patients provided prior written informed consent under a protocol approved by the Institutional Review Boards at the University of Maryland School of Medicine, the Baltimore Veterans Affairs Medical Center, and the Johns Hopkins University School of Medicine. Biopsies were obtained using a standardized biopsy protocol as previously described (Schulmann et al. (2005) *Oncogene* 24, 4138-4148). Research tissues were taken from grossly apparent BE epithelium or from mass lesions in patients manifesting these changes at endoscopic examination, and histology was confirmed using parallel aliquots culled from identical locations at endoscopy. All research biopsy specimens were stored in liquid nitrogen prior to DNA extraction. Clinicopathologic characteristics are summarized in Table 2.

TABLE 2

Clinicopathologic characteristics and methylation status of CDH13 in human esophageal tissues

| Clinical characteristics[1] | Number of samples | Age (year) mean | NMV[2] mean | p | Methylation Status (cutoff 0.06)[3] Frequency | UM | M | p |
|---|---|---|---|---|---|---|---|---|
| Histology | | | | | | | | |
| Normal esophagus | 66 | 64.3 | 0.0054 | | 0% | 66 | 0 | |
| BE | 60 | 63.7 | 0.3122 | $<0.00001*/# | 70% | 18 | 42 | |
| Ba | 36 | 62.5 | 0.2623 | | 58.3% | 15 | 21 | <0.05[†] |
| Bt | 24 | 65.5 | 0.3871 | $<0.05 | 87.5% | 3 | 21 | |
| Dysplasia in Barrett's esophagus | 40 | 65.3 | 0.3383 | $<0.00001*/# | 77.5% | 9 | 31 | |
| Low-grade dysplasia | 19 | 65.3 | 0.2833 | $<0.000001* | 78.9% | 4 | 15 | NS[†] |
| High-grade dysplasia | 21 | 65.2 | 0.388 | $<0.000001* | 76.2% | 5 | 16 | |
| EAC | 67 | 65.1 | 0.2392 | $<0.000001*/# | 76.1% | 16 | 51 | <0.0001[‡] |
| ESCC | 26 | 62.5 | 0.0458 | $<0.001* | 19.2% | 21 | 5 | |
| Barrett's segment of Ba | | | | | | | | |
| Short-segment (<3 cm) | 14 | 62.3 | 0.131 | $<0.01 | 28.6% | 10 | 4 | <0.01[†] |
| Long-segment (>=3 cm) | 16 | 62.8 | 0.4071 | | 87.5% | 2 | 14 | |
| Stage of EAC patients | | | | | | | | |
| I | 7 | 63 | 0.3081 | ¶NS | 85.7% | 1 | 6 | NS[†] |
| II | 15 | 65.2 | 0.2408 | | 73.3% | 4 | 11 | |
| III | 25 | 64.6 | 0.2111 | | 72% | 7 | 18 | |
| IV | 7 | 66.3 | 0.2921 | | 100% | 0 | 7 | |
| Lymph node metastasis in EAC patients | | | | | | | | |
| Negative | 25 | 64.9 | 0.2751 | $NS | 75% | 5 | 20 | NS[‡] |
| Positive | 25 | 64.6 | 0.2277 | | 76% | 6 | 19 | |
| Smoking status of EAC patients | | | | | | | | |
| Never | 6 | 58.5 | 0.2984 | ¶NS | 100% | 0 | 6 | NS[†] |
| Former | 24 | 68.5 | 0.2143 | | 79.2% | 5 | 19 | |
| Current | 13 | 60.8 | 0.2561 | | 76.9% | 3 | 10 | |
| Alcohol drinking status of EAC patients | | | | | | | | |
| Never | 16 | 65.3 | 0.2209 | ¶NS | 75% | 4 | 12 | NS[†] |
| Former | 15 | 63 | 0.2524 | | 86.7% | 2 | 13 | |
| Current | 10 | 65.7 | 0.2427 | | 80% | 2 | 8 | |

[1]BE, Barrett's metaplasia; Ba, BE from patients with Barrett's alone; Bt, BE from patients with Barrett's accompanied by EAC; EAC, esophageal adenocarcinoma; ESCC, esophageal squamous cell carcinoma.
[2]NMV: normalized methylation value; $, Mann-Whitney U test; *, comparisons made to normal esophagus; #, comparisons made to ESCC; ¶, Kruskal-Wallis test.
[3]UM, unmethylated; M, methylated; †, Fisher's exact test; ‡, Chi-square for independence test.
NS, not significant.

(2) Cell lines. OE33 EAC and KYSE220 ESCC cells were cultured in 47.5% RPMI 1640, 47.5% F-12 supplemented with 5% fetal bovine serum.

(3) DNA and RNA Extraction

Genomic DNA was extracted from biopsies and cultured cells using a DNeasy Tissue Kit (Qiagen, Valencia, Calif.). Total RNA was isolated from cultured cells using TRIzol reagent (Invitrogen, Carlsbad, Calif.). DNAs and RNAs were stored at −80° C. prior to analysis.

(4) Bisulfite Treatment and Real-time Methylation-specific PCR

One ug DNA was treated with bisulfate to convert unmethylated cytosines to uracils prior to MSP using an EpiTect Bisulfite Kit (Qiagen, Valencia, Calif.). Promoter methylation levels of CDH13 were determined by real-time quantitative MSP with an ABI 7900 Sequence Detection System (Applied Biosystems, Foster City, Calif.), using primers and probes as follows: CDH13-forward: 5'-TTTGGGAAGTTG-GTTGGTTGGC-3' (SEQ ID NO:17); CDH13-reverse: 5'-ACTAAAAACGCCCGACGACG-3' (SEQ ID NO:18) and probe: 5'-TATGTTTAGTGTAGTCGCGTGTATGAAT-GAA-3' (SEQ ID NO:19). β-actin was used for normalization of data. Primers and probe for β-actin were the same as previously reported (Jin et al. (2007) *Oncogene* 26, 6332-6340). A standard curve was generated using serial dilutions of CpGenome Universal Methylated DNA (CHEMICON, Temecula, Calif.). Normalized methylation value (NMV) was defined as follows: NMV=(CDH13-S/CDH13-FM)/(ACTB-S/ACTB-FM), where CDH13-S and CDH13-FM represent CDH13 methylation levels (derived from the standard curve) in sample and fully methylated DNAs, respectively, while ACTB-S and ACTB-FM correspond to β-actin in sample and fully methylated DNAs, respectively.

(5) Real-time Quantitiative RT-PCR

To determine CDH13 mRNA levels, one-step real-time quantitative RT-PCR was performed using a Qiagen QuantiTect Probe RT-PCR Kit (Qiagen, Hilden, Germany) and an ABI 7900 Sequence Detection System (Applied Biosystems, Foster City, Calif.). Primers and probe for CDH13 were as follows: CDH13-forward: 5'ATGTTGGCAAGGTAGTC-GATAGTG-3' (SEQ ID NO:20); CDH13-reverse: 5'-ACGCTCCCTGTGTTCTCATTG-3' (SEQ ID NO:21) and probe: 5'-CCAGAAAGGTCCAAGTTCCGGCT-CACT-3' (SEQ ID NO:22). β-actin was used for normalization of data. Primers and probe for β-actin were the same as previously reported (Jin et al. (2007) *Oncogene* 26, 6332-6340). A standard curve was generated using serial dilutions of qPCR Reference Total RNA (Clontech, Mountainview, Calif.). Normalized mRNA value (NRV) was calculated according to the following formula for relative expression of target mRNA: NRV=(TarS/TarC)/(ACTB-S/ACTB-C, where TarS and TarC represent levels of target gene mRNA expression (derived from the standard curve) in sample and control mRNAs, respectively, while ACTB-S and ACTB-C correspond to amplified ACTB levels in sample and control mRNAs, respectively.

(6) 5-Aza-dC Treatment of Esophageal Cancer Cell Lines

To determine whether CDH13 inactivation was due to promoter hypermethylation in esophageal cancer, 2 esophageal cancer cell lines (KYSE220 and OE33) were subjected to 5-Aza-dC (Sigma, St. Louis, Mo.) treatment as previously described (Bender et al. (1999) *Mol Cell Biol* 19, 6690-6698; Shibata et al. (2002) *Cancer Res* 62, 5637-5640). Briefly, $1\times10^5$ cells/ml were seeded onto a 100 mm dish and grown for 24 h. Then, 1 µl of 5 mM 5-Aza-dC per ml of cells was added every 24 hours for 4 days. DNAs and RNAs were harvested on day 4.

(7) Data Analysis and Statistics

Receiver-operator characteristic (ROC) curve analysis (Hanley et al. (1982) *Radiology* 143, 29-36) was performed using NMVs for the 67 EAC, 26 ESCC and 66 NE specimens by Analyse-It© software (Version 1.71, Analyse-it Software, Leeds, UK). Using this approach, the area under the ROC curve (AUROC) identified optimal sensitivity and specificity levels at which to distinguish normal from malignant esophageal tissues (NE vs. EAC), yielding a corresponding NMV threshold with which to dichotomize the methylation status of CDH13. The threshold NMV value determined from this ROC curve was applied to determine the status of CDH13 methylation in all tissue types included in the study. For all other statistical tests, Statistica (version 6.1; StatSoft, Inc., Tulsa, Okla.) was employed. Differences with $p<0.05$ were considered significant.

B. Results (1) CDH13 Promoter Hypermethylation in Esophageal Tissues

Promoter hypermethylation of CDH13 was analyzed in 66 NE, 60 BE (including 36 Ba and 24 Bt), 40 D (including 19 LGD and 21 HGD), 67 EAC, and 26 ESCC. CDH13 promoter hypermethylation showed highly discriminative ROC curve profiles and AUROCs, clearly distinguishing both EAC and ESCC from NE (FIGS. 9A and 9B), as well as EAC from ESCC (FIG. 9C).

The cutoff NMV for CDH13 (0.06) was identified from the ROC curve (EAC vs. NE) to achieve the highest possible sensitivity while maintaining 100% specificity. Mean NMV and frequency of CDH13 hypermethylation for each tissue type are shown in Table 2.

NMVs of CDH13 were significantly higher in ESCC, EAC, D, HGD, LGD, BE, Ba and Bt than in NE ($p<0.001$, Mann-Whitney U test). The frequency of CDH13 hypermethylation was significantly higher in BE (70%), D (77.5%), and EAC (76.1%) than in N (0%; $p<0.0001$, $p<0.0001$ and $p<0.0001$, respectively; Fisher's exact test). Interestingly, both CDH13 hypermethylation frequency and mean NMV were significantly higher in Bt than in Ba (87.5% vs. 58.3%, $p=0.021$ and 0.3871 vs. 0.2623, $p=0.045$, respectively). The mean CDH13 NMV in EAC (0.2722) was significantly higher than that in matching NE (0.0034) for 27 cases in which matching NE and EAC were available ($p<0.00001$, Wilcoxon matched pairs test). In contrast to EAC, only five (19.2%) of 26 ESCCs manifested hypermethylation of CDH13. There was no significant difference in mean CDH13 NMV between tumor and normal tissue in 13 cases for which matching ESCC (0.0337) and NE (0.0131; $p=0.6$, Wilcoxon matched pairs test) were available. Both CDH13 hypermethylation frequency and mean NMV were significantly higher in EAC than in ESCC (76.1% vs. 19.2%, $p<0.0001$ and 0.2392 vs. 0.0458, $p<0.0001$, respectively), as well as in D vs. ESCC (77.5% vs. 19.2%, $p<0.0001$ and 0.3383 vs. 0.0458, $p<0.0001$, respectively) and in BE vs. ESCC (70% vs. 19.2%, $p<0.0001$ and 0.3122 vs. 0.0458, $p<0.0001$; Table 2).

According to generally accepted criteria, BE was defined as long-segment (LSBE) if it was equal to or greater than 3 cm in length, or short-segment (SSBE) if less than 3 cm. The mean NMV of CDH13 was significantly higher in LSBE than in SSBE (0.4071 vs. 0.131; $p<0.01$, Student's t-test, Table 2 and FIG. 10A). Similarly, segment lengths of BEs with methylated CDH13 promoters (mean=5.83 cm) were significantly longer than segment lengths of BEs with unmethylated CDH13 promoters (mean=1.83 cm; $p<0.001$, Student's t-test; FIG. 10B), and the frequency of CDH13 hypermethylation was significantly higher in LSBE than in SSBE (87.5% vs. 28.6%; $p<0.01$, Fisher's exact test; Table 2).

No significant associations were observed between CDH13 promoter hypermethylation and patient age (data not shown), survival (log-rank test, data not shown), tumor stage, lymph node metastasis, smoking, or alcohol consumption (Table 2).

(2) CDH13 Methylation and mRNA Levels in Esophageal Cancer Cell Lines Pre- and Post-5-Aza-dC Treatment KYSE220 ESCC and OE33 EAC cells were subjected to 5-Aza-dC treatment. After 5-Aza-dC treatment, the NMV of CDH13 was diminished and the mRNA level of CDH13 was increased in both KYSE220 and OE33 cells (FIG. 11).

C. Discussion

In this Example, we systematically investigated hypermethylation of the CDH13 gene promoter in cell lines and primary human esophageal lesions of contrasting histological types and grades by qMSP. Our results demonstrate that CDH13 promoter hypermethylation occurs frequently in human EAC, but not in ESCC. In addition, our data show that CDH13 hypermethylation increases early during esophageal adenocarcinogenesis, from 0% in NE to 58.3% in BE, 77.5% in D, and 76.1% in EAC. These results imply that hypermethylation of CDH13 occurs early in most subjects, that its frequency increases during adenocarcinogenesis, and that it is tissue-specific (i.e., common in EAC but rare in ESCC). Further evidence supporting this tissue specificity is provided by ROC curves, which clearly distinguished EAC from ESCC. Similarly, support for tissue specificity is evident from the finding that both CDH13 hypermethylation frequency and mean CDH13 NMV were significantly higher in EAC than in ESCC. In addition, the low frequency (19.2%) of CDH13 hypermethylation in ESCC, as determined in the current study, is consistent with previous findings by other groups. Thus, CDH13 hypermethylation appears to constitute a critical event unique to human EAC.

Several studies have suggested that methylation of certain genes may occur as a field change and may be associated with an increased risk of malignant progression. CDKN2A, ESR1, and MYOD1 were methylated only in BE from patients who possessed dysplasia or cancer in other regions of their esophagus, but not in patients with no evidence of progression beyond BE, while CALCA, MGMT, and TIMP3 were methylated more frequently in normal stomach, normal esophageal mucosa and intestinal metaplasia from patients with distant dysplasia or esophageal cancer than from patients without dysplasia or cancer. Previously, we demonstrated that hypermethylation of p16, RUNX3, and HPP1 in BE or LGD may represent independent risk factors for the progression of BE to HGD or EAC (Schumann et al. (2005) Oncogene 24, 4138-4148). Example I herein shows that both hypermethylation frequency and NMV of the nel-like 1, tachykinin-1, somatostatin and AKAP12 genes were higher in BE with accompanying EAC than in BE without accompanying EAC. Interestingly, both CDH13 hypermethylation frequency and level were significantly higher in BE with than without accompanying EAC in the current study, suggesting that CDH13 is a biomarker of more ominous disease lurking nearby.

In the present Example, we also correlated CDH13 methylation with clinicopathologic features. Despite some degree of controversy regarding the length of the BE segment as a predictive factor in BE progression, it is likely that this clinical parameter is an important predictor of neoplastic progression. In the Seattle Barrett's Esophagus Project, BE segment length was not related to cancer risk in a prospective cohort study of 309 Barrett's patients (p>0.2); however, when patients with HGD at entrance were excluded, a strong trend was observed, with a 5 cm difference in length associated with a 1.7-fold increase in cancer risk (95% CI, 0.8-3.8-fold). Significant differences in the frequency of both dysplasia and EAC were observed between SSBE and LSBE, at 8.1% vs. 24.4% for dysplasia (p<0.0001) and 0% vs. 15.4% for EAC (p<0.0005). In a comprehensive prospective study of 889 consecutive patients, the prevalence of dysplasia and cancer differed significantly in patients with SSBE vs. LSBE. More recently, a significantly increased risk of progression to HGD or EAC with LSBE after a mean follow-up of 12.7 years was reported. In the studies described in Example I, the nel-like 1, tachykinin-1, somatostatin and AKAP12 genes were significantly more hypermethylated in LSBE than in SSBE. Notably, in the current study, CDH13 methylation also showed a strong relationship to BE segment length. The mean NMV of CDH13 was significantly higher in LSBE than in SSBE. Similarly, the length of the BE segment was significantly greater in specimens with methylated than with unmethylated CDH13 promoters. Thus, CDH13 hypermethylation may constitute a molecular correlate of BE segment length, as well as a harbinger of nearby neoplastic disease. These results also suggest that epigenetic alterations, which may account for some of the biologic behavior of BE, clearly differ between LSBE and SSBE, suggesting a need for further large-scale studies.

In accordance with previous findings in other primary cancer cell types, we observed that methylation of CDH13 in EAC and ESCC cancer cell lines was associated with silenced or reduced expression of CDH13 mRNA. Treatment with 5-Aza-dC restored mRNA expression and reversed CDH13 methylation in these cells. Restoration of CDH13 mRNA expression by demethylating agent treatment implies that DNA hypermethylation was responsible for silencing of CDH13.

In summary, findings of this Example suggest that hypermethylation of the CDH13 promoter is a common event in human esophageal adenocarcinogenesis, occurs early during Barrett's-associated esophageal carcinogenesis, and is associated with clinical risk factors of progression. In addition, CDH13 hypermethylation is uncommon in human ESCC, thus making it a potential cell type-specific biomarker for EAC.

Example III

A Multicenter, Double-blinded Validation Study of Methylation Biomarkers for Progression Prediction in Barrett's Esophagus Esophageal adenocarcinoma risk in Barrett's esophagus (BE) is increased 30- to 125-fold versus the general population, yet neoplastic progression occurs rarely in BE. Molecular biomarkers would stratify patients for more efficient surveillance endoscopy and improve early detection of progression. We therefore performed a retrospective, multicenter, double-blinded validation study of 8 BE progression prediction methylation biomarkers. Progression or nonprogression were determined at 2 years (tier 1) and 4 years (tier 2). Methylation was assayed in 145 nonprogressors (NPs) and 50 progressors (Ps) using real-time quantitative methylation-specific PCR. Ps were significantly older than NPs (70.6 vs. 62.5 years, p<0.001). We evaluated a linear combination of the 8 markers, using coefficients from a multivariate logistic regression analysis. Areas under the ROC curve (AUCs) were high in the 2-, 4-year and combined data models (0.843, 0.829 and 0.840; p<0.001, p<0.001 and p<0.001, respectively). In addition, even after rigorous overfitting correction, the incremental AUCs contributed by panels based on the 8 markers plus age vs. age alone were substantial ($\Delta$-AUC=0.152, 0.114 and 0.118, respectively) in all three models. A methylation biomarker-based panel to predict neoplastic progression in BE has clinical value in improving both the efficiency of surveillance endoscopy and the early detection of neoplasia.

A. Materials and Methods (1) Definition of Barrett's esophagus progressor and nonprogressor patients and sample collection. Progressors (Ps) and nonprogressors (NPs) were defined as described previously (Montgomery et al. (2001) Hum Pathol 32, 379-388). Ps were considered both as a single combined group, and in two tiers: progression within 2 years (tier 1) or 4 years (tier 2). 195 BE biopsies (145 NPs and 50 Ps) were obtained from 5 participating centers: the Mayo Clinic at Rochester/Jacksonville, the University of Arizona, the University of North Carolina, and Johns Hopkins University. All patients provided written informed consent under a protocol approved by Institutional Review Boards at their institutions. Biopsies were taken using a standardized biopsy protocol (Corley et al. (2002) Gastroenterology 122, 633-640; Montgomery et al. (2001, supra). Clinicopathologic features are summarized in Table 3.

TABLE 3

Clinicopathologic characteristics in 50 progressors and 145 non-progressors

| | Progressor (N = 50) | Non-Progressor (N = 145) | p value |
|---|---|---|---|
| Age (years, mean ± SD)* | 70.6 ± 9.1 | 62.5 ± 12.3 | <0.001 |
| Gender | | | |
| Male | 46 (92%) | 113 (78%) | NS |
| Female | 4 (8%) | 32 (22%) | |
| Race | | | |
| White | 50 (100%) | 144 (99%) | NS |
| Unknown | 0 (0%) | 1 (1%) | |
| Index of Histology | | | |
| BE | 26 (52%) | 87 (60%) | NS |
| LGD | 22 (44%) | 58 (40%) | |

TABLE 3-continued

Clinicopathologic characteristics in 50 progressors and 145 non-progressors

|  | Progressor (N = 50) | Non-Progressor (N = 145) | p value |
|---|---|---|---|
| Unknown | 2 (4%) | 0 (0%) |  |
| Barrett's length (cm, mean ± SD) | 6.0 ± 3.3 | 5.4 ± 3.6 | NS |
| Body mass index (kg/m$^2$) |  |  |  |
| Normal weight (18.5-24.9) | 10 (20%) | 27 (19%) | NS |
| Overweight (25-29.9) | 15 (30%) | 53 (37%) |  |
| Obese (30+) | 20 (40%) | 53 (37%) |  |
| Unknown | 5 (10%) | 12 (8%) |  |
| Smoking status* |  |  |  |
| Yes | 4 (8%) | 15 (10%) | NS |
| No | 46 (92%) | 124 (86%) |  |
| Unknown | 0 (0%) | 6 (4%) |  |
| Alcohol Use* |  |  |  |
| Yes | 15 (30%) | 43 (30%) | NS |
| No | 35 (70%) | 94 (65%) |  |
| Unknown | 0 (0%) | 8 (6%) |  |
| ASA/NSAID use* |  |  |  |
| Yes | 17 (34%) | 61 (42%) | 0.039** |
| No | 33 (66%) | 81 (56%) |  |
| Unknown | 0 (0%) | 3 (2%) |  |
| PPI or H2 Blocker* |  |  |  |
| Yes | 40 (80%) | 123 (85%) | NS |
| No | 10 (20%) | 21 (14%) |  |
| Unknown | 0 (0%) | 1 (1%) |  |
| Family History of BE, LGD, HGD or EAC |  |  |  |
| Yes | 3 (6%) | 11 (8%) | NS |
| No | 47 (94%) | 126 (87%) |  |
| Unknown | 0 (0%) | 8 (6%) |  |

SD, standard deviation; BE, Barrett's metaplasia; LGD, low-grade dysplasia; HGD, high-grade dysplasia; EAC, esophageal adenocarcinoma; ASA, acetylsalicylic acid; NSAID, non-steroidal anti-inflammatory drug; PPI, proton pump inhibitor; NS, not significant.
*at time of procedure;
**p-value is adjusted for age.

(2) Bisulfite Treatment and Real-Time Quantitative Methylation-Specific PCR (qMSP)

Bisulfite treatment was performed and promoter methylation levels of 8 genes (p16, HPP1, RUNX3, CDH13, TAC1, NELL1, AKAP12 and SST) were determined by qMSP on an ABI 7900 Sequence Detection (Taqman) System, as described in Montgomery et al. (2001, supra). β-actin was used for normalization. Primers and probes for qMSP are described in Table 4. In this table, the forward primer sequences, reading from top to bottom, are SEQ ID NOs: 23-31; the reverse primer sequences, reading from top to bottom, are SEQ ID NOs: 32-40; and the TaqMan probe sequences, reading from top to bottom, are SEQ ID NOs: 41-49.

A standard curve was generated using serial dilutions of CpGenome Universal Methylated DNA (CHEMICON, Temecula, Calif.). A normalized methylation value (NMV) for each gene of interest was defined as described in Montgomery et al. (2001, supra). Wetlab analysts and all SJM laboratory personnel were blinded to specimen P or NP status.

(3) Data Analysis and Statistics

Associations between progression status and patient characteristics were tested using Student's t-test or Chi-squared testing. Relationships between biomarkers and patient progression status were examined using Wilcoxon rank-sum testing.

To evaluate the predictive utility of the markers, we constructed receiver operating characteristic (ROC) curves. ROC curve analyses were first conducted on individual markers, then in combination to determine whether a panel performed better than any single marker. Our algorithm rendered a single composite score, using the linear predictor from a binary regression model justified under the linearity assumption (Jin et al. 2007) Clin Cancer Res 13, 6293-6300). The predictive accuracy of composite scores was evaluated based on a resampling algorithm: we randomly split data into a learning set containing ⅔ and a test set including ⅓ of observations. The combination rule derived from the learning set produced two ROC curves, from the learning and test sets, respectively. Vertical differences between these two ROC curves yielded the overestimation of sensitivities at given specificities. This procedure was repeated 200 times, and these 200 differences were averaged to estimate the expected overfitting.

We also utilized predictiveness curves (Jin et al. (2008) Cancer 112, 43-49) to display risk distribution as a function of the combined marker in the population. This curve represents a plot of risk associated with the $v^{th}$ quantile of the marker, $P\{D=1|Y=F^{-1}(v)\}$ vs. v, with F(•) the cumulative distribution of the marker. These plots display population proportions at different risk levels more clearly than do other metrics (like ROC curves). Since a case-control sample was studied, we used an external progression prevalence rate to calculate risk in the targeted screening population. To calibrate for future samples, a shrinkage coefficient estimated from the logistic regression model was applied to the linear predictors from which risk was calculated (Jin et al. (2008) Cancer Epidemiol Biomarkers Prev 17, 111-117).

All analyses were performed in R (see the world wide web site www.r-project.org). Statistical data analysts were blinded to the identities of the 8 biomarkers.

B. Results (1) Clinical Characteristics

Ps vs. NPs did not differ significantly by gender, body mass index, BE segment length, LGD patient percentage, family history of BE, LGD, HGD or EAC, cigarette smoking, or alcohol use; however, Ps were significantly older than NPs (70.6 vs. 62.5 years; p<0.001, Student's t test; Table 3). Samples consisted of one biopsy from each of 50 Ps and 145 NPs (195 patients) in the combined model. In the 2-year model, we redefined progressors whose interval from index to final procedure exceeded 2 years as nonprogressors, yielding 36 Ps and 159 NPs. In the 4-year model, we redefined progressors whose interval from index to final procedure exceeded 4 years as nonprogressors, yielding 47 Ps and 148 NPs.

(2) Univariate Analyses

NMVs of HPP1, p16 and RUNX3 were significantly higher in Ps vs. NPs by Wilcoxon test (0.456, 0.138, and 0.104 vs. 0.273, 0.069 and 0.063; p=0.0025, 0.0066 and 0.0002, respectively). The remaining 5 markers did not differ significantly in Ps vs. NPs (Table 5).

TABLE 5

Univariate analysis for 8 methylation biomarkers in 50 progressors and 145 non-progressors

| Biomarker | NMV (mean ± SD) Non-progressor | NMV (mean ± SD) Progressor | p value (Wilcoxon rank sum test) |
|---|---|---|---|
| HPP1 | 0.273 ± 0.326 | 0.456 = 0.432 | 0.0025 |
| p16 | 0.069 ± 0.209 | 0.138 ± 0.249 | 0.0066 |
| RUNX3 | 0.063 ± 0.179 | 0.104 ± 0.168 | 0.0002 |
| CDH13 | 0.169 ± 0.263 | 0.201 ± 0.373 | 0.7682 |
| TAC1 | 0.193 ± 0.231 | 0.231 = 0.228 | 0.1686 |
| NELL1 | 0.148 ± 0.247 | 0.113 ± 0.150 | 0.7644 |
| AKAP12 | 0.163 ± 0.244 | 0.280 ± 0.403 | 0.2484 |
| SST | 0.455 ± 0.378 | 0.482 = 0.486 | 0.9143 |

NMV, normalized methylation value; SD, standard deviation

We further assessed the classification accuracy of single markers using ROC curve analyses. Areas under ROC curve (AUCs) for HPP1, p16 and RUNX3 were all significantly greater than 0.50, (Table 6).

TABLE 6

Receiver-operator characteristic curve analysis for 8 methylation biomarkers in 50 progressors and 145 non-progressors

| Biomarker | AUC (95% confidence interval) |
|---|---|
| HPP1 | 0.647 (0.556, 0.739) |
| p16 | 0.628 (0.534, 0.722) |
| RUNX3 | 0.671 (0.586, 0.756) |
| CDH13 | 0.515 (0.409, 0.622) |
| TAC1 | 0.571 (0.470, 0.673) |
| NELL1 | 0.516 (0.420, 0.611) |
| AKAP12 | 0.561 (0.451, 0.672) |
| SST | 0.506 (0.401, 0.611) |

AUC, area under the receiver-operator characteristic curve (3) Logistic Regression Analyses of the 8-marker Panel We then combined all 8 markers by performing logistic regression and treating them as linear predictors (Table 7, FIG. 12)

All models exhibited high AUCs (0.843, 0.829 and 0.840, respectively; Table 7, FIGS. 12A-12C. We performed overfitting correction based on 3-fold cross-validation and 200 bootstraps. The overfitting-corrected AUCs remained high (0.745, 0.720 and 0.732, respectively), while shrinkages from overfitting correction were modest (0.098, 0.109 and 0.108, respectively) in the three models (Table 7, FIGS. 12A-12C).

We also explored the incremental AUC value contributed by an 8-marker-plus-age panel to that of age alone (Table 8, FIG. 12). The AUCs of the 8-marker-plus-age panels in the three models (0.858, 0.850 and 0.855, respectively) were higher than those of age alone (0.604, 0.630 and 0.635, respectively; Table 8, FIGS. 12D-12F).

Overfitting-corrected AUCs remained high (0.756, 0.744 and 0.753, respectively), and increments contributed by the age-plus-biomarker panel vs. age were substantial (0.152, 0.114 and 0.118, respectively) in the three models (Table 8, FIGS. 12D-12F).

(4) Sensitivity and Specificity of the 8-marker Panel

While maintaining high specificity to minimize false-positive results, our model still predicted a number of new early diagnoses, i.e., diagnoses that would not have occurred earlier without the panel (Table 9).

While maintaining specificity at 0.9 or 0.8, sensitivities (0.443 and 0.629 for the combined model, 0.607 and 0.721 for the 2-year model, and 0.465 and 0.606 for the 4-year model, respectively) were above or approached 50% in all three models based on the 8-marker panel alone. Furthermore, at 0.9 or 0.8 specificities, sensitivities (0.457 and 0.757 for the combined model, 0.536 and 0.786 for the 2-year model, and 0.450 and 0.724 for the 4-year model, respectively) exceeded or approached 50% in all models based on the 8-marker-plus-age panel.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent applications 61/066,281, filed Feb. 19, 2008; 61/131,748, filed Jun. 11, 2008; and 61/132,418, filed Jun. 18, 2008) cited above and in the figures are hereby incorporated in their entirety by reference.

TABLE 4

Supplementary Table 4. Primer and probe sequences

| Gene | Forward primer sequence (5'-3') | Reverse primer sequence (5'-3') | TaqMan probe sequence (5'-3') |
|---|---|---|---|
| HPP1 | GTTATCGTCGTCGTTTTTGTTGTC | GACTTCCGAAAAACACAAAATCG | CCGAACAACGAACTACTAAACATCCCGCG |
| p16 | TGGAATTTTCGGTTGATTGGTT | AACAACGTCCGCACCTCCT | ACCCGACCCCGAACCGCG |
| RUNX3 | GGGTTTTGGCGAGTAGTGGTC | ACGACCGACGCGAACG | CGTTTTGAGGTTCGGGTTTCGTCGTT |
| CDH13 | TTTGGGAAGTTGGTTGGTTGGC | ACTAAAAACGCCCGACGACG | TATGTTTAGTGTAGTCGCGTGTATGAATGAA |
| Tachykinin-1 | GGCGGTTAATTAAATATTGAGTAGAAAGTCGC | AAATCCGAACGCGCTCTTTCG | AGAATGTTACGTGGGTTTGGAGGTTTAAGGAG |
| Nel-like 1 | GGGTTTTTAGACGAACGTAGTCGTAGC | CCACCGCTAACGCGACGA | ACGACGTAAAACTCGAAACCCGACCC |
| AKAP12 | GTTTTGTTAGAAACGGGAGGCGTTC | GAAACCAAAAACGCTACGACGCG | TCGGGTGGGCGGTTGTTTGGATT |
| Somatostatin | GGGGCGTTTTTTAGTTTGACGT | AACAACGATAACTCCGAACCTCG | AACGACTTATATACTCTCAACCGTCTCCCTCTA |
| β-actin | TGGTGATGGAGGAGGTTTAGTAAGT | AACCAATAAAACCTACTCCTCCCTTAA | ACCACCACCCAACACACAATAACAAACACA |

TABLE 7

Logistic regression and overfitting correction for the 2-year, 4-year and combined models

|  | AUC$_1$ (95% CI) | p-value of AUC$_1$ | AUC$_2$ (95% CI) | p-value of AUC$_2$ | Shrinkage (AUC$_1$ − AUC$_2$) |
|---|---|---|---|---|---|
| 2-year model | 0.843 (0.763, 0.924) | <0.001 | 0.745 (0.685, 0.875) | 0.001 | 0.098 |
| 4-year model | 0.829 (0.773, 0.907) | <0.001 | 0.720 (0.694, 0.856) | 0.004 | 0.109 |
| combined model | 0.840 (0.773, 0.907) | <0.001 | 0.732 (0.697, 0.868) | 0.002 | 0.108 |

AUC, area under the receiver-operator characteristic curve; AUC$_1$, original AUC; AUC$_2$, overfitting corrected AUC; CI, confidence interval.

TABLE 8

Incremental values above age alone for the 2-year, 4-year and combined models

|  | AUC$_1$ (95% CI) | AUC$_2$ (95% CI) | AUC$_3$ (95% CI) | Increment over age (AUC$_3$ − AUC$_1$) |
|---|---|---|---|---|
| 2-year model | 0.604 (0.491, 0.718) | 0.858 (0.783, 0.932) | 0.756 (0.699, 0.884) | 0.152 |
| 4-year model | 0.630 (0.526, 0.735) | 0.850 (0.784, 0.917) | 0.744 (0.719, 0.871) | 0.114 |
| combined model | 0.635 (0.532, 0.737) | 0.855 (0.790, 0.919) | 0.753 (0.729, 0.878) | 0.118 |

AUC, area under the receiver-operator characteristic curve; AUC$_1$, AUC of age alone; AUC$_2$, AUC of age plus markers; AUC$_3$, overfitting corrected AUC of age plus markers; CI, confidence interval.

TABLE 9

Specificity and sensitivity for 2-year, 4-year and combined models

|  | Specificity (95% CI) at sensitivity = | | Sensitivity (95% CI) at specificity = | |
|---|---|---|---|---|
|  | 0.9 | 0.8 | 0.9 | 0.8 |
| Combined model | | | | |
| Age | 0.260 (0.162, 0.425) | 0.390 (0.240, 0.508) | 0.221 (0.054, 0.448) | 0.371 (0.204, 0.532) |
| Marker combination | 0.567 (0.413, 0.849) | 0.724 (0.574, 0.914) | 0.443 (0.350, 0.838) | 0.629 (0.527, 0.941) |
| Age + marker combination | 0.576 (0.484, 0.867) | 0.781 (0.647, 0.944) | 0.457 (0.372, 0.869) | 0.757 (0.598, 0.964) |
| 2-year model | | | | |
| Age | 0.205 (0.138, 0.389) | 0.351 (0.197, 0.484) | 0.176 (0.021, 0.426) | 0.354 (0.172, 0.538) |
| Marker combination | 0.547 (0.436, 0.873) | 0.757 (0.595, 0.935) | 0.607 (0.393, 0.870) | 0.721 (0.593, 0.969) |
| Age + marker combination | 0.615 (0.474, 0.918) | 0.786 (0.652, 0.956) | 0.536 (0.400, 0.934) | 0.786 (0.600, 0.987) |
| 4-year model | | | | |
| Age | 0.249 (0.158, 0.430) | 0.384 (0.229, 0.506) | 0.232 (0.038, 0.467) | 0.382 (0.214, 0.541) |
| Marker combination | 0.523 (0.426, 0.835) | 0.704 (0.579, 0.909) | 0.465 (0.346, 0.814) | 0.606 (0.545, 0.941) |
| Age + marker combination | 0.574 (0.488, 0.864) | 0.757 (0.649, 0.940) | 0.450 (0.385, 0.885) | 0.724 (0.600, 0.963) |

CI, confidence interval (5) Risk Stratification of BE Patients

ROC curves derived from these marker-based models were used to establish thresholds to stratify patients into risk categories. This procedure was performed to identify high-risk (HR) individuals for more frequent endoscopic screening. The threshold above which patients were classified as HR was chosen at specificity=90%, to minimize false-positive, unnecessary endoscopies (type II error). A second threshold was established to identify low-risk (LR) individuals for less frequent endoscopic screening. The threshold below which patients were classified as LR was chosen at sensitivity=90%, to minimize false-negative, missed HR individuals (type I error). Based on the combined P and NP classification, we classified patients as LR with a threshold that corresponded to 90% true-positives and 43% false-positives; the HR group was defined using a threshold that yielded 43% true-positives and 10% false-positives. Assuming progression to HGD and/or EAC at 13.5% over 5 years (Jin et al. (2008) *International Journal of Cancer* 123, 2331-2336), the corresponding negative predictive value relating to our LR threshold was 97% (i.e., progression risk in the LR group was 3%) and the positive predictive value relating to HR was 40% (i.e., progression risk in the HR group was 40%).

(6) Predictiveness Curve Analyses

We used predictiveness curves (also known as risk plots) to assess the clinical utility of the combined classification rules in stratifying patients according to risk levels in the target population. To create predictiveness curves, we ordered and plotted risks from lowest to highest value. A progression rate to HGD and/or EAC of 13.5% over 5 years was assumed in adjusting estimates from the case-control sample to reflect population risk and its distribution. Results are shown in Table 10, FIG. 13.

TABLE 10

Overfitting-corrected predictiveness curve analyses in 2-year, 4-year and combined models

| | Risk probability | | |
|---|---|---|---|
| | <0.1 (LR) | 0.1-0.5 (IR) | >0.5 (HR) |
| Combined model | | | |
| 8-marker panel | 45% | 51% | 4% |
| age alone | 15% | 85% | 0% |
| age plus 8-marker panel | 51% | 44% | 5% |
| 2-year model | | | |
| 8-marker panel | 45% | 51% | 4% |
| age alone | 11% | 89% | 0% |
| age plus 8-marker panel | 52% | 44% | 4% |
| 4-year model | | | |
| 8-marker panel | 44% | 51% | 5% |
| age alone | 15% | 85% | 0% |
| age plus 8-marker panel | 51% | 44% | 5% |

LR, low-risk; IR, intermediate-risk; HR, high-risk.

After overfitting correction, by age alone, nearly 90% of BE patients were classified as intermediate-risk (IR), whereas patients were well-stratified into low-risk (LR), IR, or high-risk (HR) categories by both the 8-marker alone and age plus 8-marker panels in all three models (Table 10, FIG. 13).

(7) Discussion

In the current study, with specificity at 0.9, sensitivities of progression prediction approached 50% based on both the 8-marker panel alone and 8-marker-plus-age panel in all three models. These findings indicate that even while performing at high specificity, these biomarker models predicted half of progressors to HGD and EAC that would not have been diagnosed earlier without using these biomarkers.

Based on age alone, with specificity at 90%, only 17.6%, 23.2% and 22.1% of progressors were predicted in the three models. However, with panels based on age plus biomarkers or on biomarkers alone, approximately 60%, 50% and 50% of progressors were accurately predicted in these models. Predicted progressors represent patients in whom we can intercede earlier, resulting in higher cure rates. Finally, our combined risk model outperformed known risk in the general BE population (13.5% progression risk over 5 years), both in negative predictive value (3% progression risk over 5 years for the LR group) and positive predictive value (40% progression risk over 5 years for the HR group).

Age is a common risk factor for many cancers, including EAC. In the current study, Ps were significantly older than NPs, and the AUCs of age alone were 0.604, 0.630 and 0.635, respectively in the three models, suggesting that age per se predicts neoplastic progression in BE. However, the incremental prediction accuracy (above age) contributed by the 8-marker panel was substantial in all three models.

Thus, the current findings suggest that this 8-marker panel is more objective and quantifiable and possesses higher predictive sensitivity and specificity than do clinical features, including age. Furthermore, although age was a good classifier for disease progression, predictiveness curves revealed that age did not successfully stratify BE patients according to their progression risk. Moreover, age per se is not an accepted risk marker on which to base clinical decisions regarding surveillance interval or neoplastic progression risk in BE. In contrast, models based on both the 8-marker panel and the age-plus-8-marker panel provided estimated progression risks either close to 0 (i.e., LR) or between 0.1 and 0.5 (i.e., IR) in the majority of individuals, suggesting that these markers exerted a substantial impact on risk category. This finding also suggests that in clinical practice, separate thresholds can be chosen to define high, intermediate, and low risk, based on predictiveness curves.

In conclusion, we have developed a risk stratification strategy to predict neoplastic progression in BE patients based on an 8-marker tissue methylation panel. At high specificity levels, this model accurately predicted approximately half of HGDs and EACs that would not have otherwise been predicted. This model is expected to reduce endoscopic procedures performed in BE surveillance while simultaneously increasing detection at earlier stages. Thus, these findings suggest that a methylation biomarker panel offers a clinically useful tool in the risk stratification of BE patients.

Example IV

Identification of about 50 Additional Markers for Predicting the Development of EAC or HGD Agilent methylation array analyses were performed on 5 BE progressor patients (BE biopsy tissue samples from subjects who later developed HGD or EAC) and 4 BE nonprogressor patients (BE biopsy tissue samples from subjects who did not later develop HGD or EAC). Bioinformatic calculations and gene filtering criteria were applied to the data generated. Based on these procedures, a list of 50 methylation targets strongly associated with progression was derived. The screen included Student's t-testing for significance of associations, selection of loci that were hypermethylated in progressors vs. nonprogressors, and gene ontologic criteria for relevance of loci to cancer. "T-test (unlogged)" connotes the t-test performed on methylation values that were not log-transformed. "Fold change" denotes the ratio for each gene or locus of methylation level in progressors to methylation level in nonprogressors.

Table 11 lists about 50 of the most promising markers identified by this study. Column 1 indicates the gene symbol of each gene, column 2 the gene ID number, and column 3 the official name of the gene. Having this information, a skilled worker can readily determine genomic sequences comprising coding sequences for each of these genes (e.g., for part or all of exon 1), and upstream regulatory regions, by accessing, for example, GenBank and/or the Entrez Gene searchable database (NCBI). The position of the transcription start sites can be found on any of these web sites, or elsewhere. Table 12 provides the start position and the end position, relative to the transcriptional initiation site, for the probes from the Agilent Human CpG Island microarray which was used to identify each of these targets. A skilled worker can readily determine the sequence of each of these probes, by matching the start and end positions relative to the relevant genomic sequence. Sequences of promoter regions of these about 50 genes, extending from −500 to +100 nucleotides relative to the transcriptional start sites, are provided in the Sequence Listing attached hereto, as SEQ ID NOs: 50-121. In some cases, two or more promoter sequences are listed for each gene, so multiple promoter regions are provided.

Table 12 also provides the results of an unlogged T-test, the test of significance of association of progression with methylation level, performed on non-log-transformed methylation values. Values of less than 0.05 indicate statistically significant results. Also included in Table 2 are the fold changes, which further clarifies the significance of the results.

Table 13 provides suitable PCR primers and probes for qMSP analysis for a number of gene promoter regions that can be analyzed by a method of the invention. The forward primers sequences have SEQ ID NOs: 122 to 199, starting at the top of the table (AKAP 12) and ending at the bottom of the table (TDE/TMS/SERINC3); the reverse primers have SEQ ID NOs: 200-277, starting at the top of the table (AKAP 12) and ending at the bottom of the table (TDE/TMS/SERINC3); and the TaqMan probe sequences have SEQ ID NOs: 278 to 295, starting at the top of the table (AKAP 12) and ending at the bottom of the table (TDE/TMS/SERINC3).

TABLE 11

| Gene Symbol | Gene ID | Name |
| --- | --- | --- |
| WIT1 | 51352 | Wilms tumor upstream neighbor 1 |
| CNTNAP5 | 129684 | contactin associated protein-like 5 |
| KCNG2 | 26251 | potassium voltage-gated channel, subfamily G, member 2 |
| ACTRT2 | 140625 | actin-related protein T2 |
| PHC2 | 1912 | polyhomeotic homolog 2 (*Drosophila*) |
| OTOP1 | 133060 | otopetrin 1 |
| TUSC3 | 7991 | tumor suppressor candidate 3 |
| CEBPD | 1052 | CCAAT/enhancer binding protein (C/EBP), delta |
| WDR5 | 11091 | WD repeat domain 5 |
| CALML3 | 810 | calmodulin-like 3 |
| CIDEA | 1149 | cell death-inducing DFFA-like effector a |
| CAMK2N2 | 94032 | calcium/calmodulin-dependent protein kinase II inhibitor 2 |
| STX1A | 6804 | syntaxin 1A (brain) |
| SMARCD3 | 6604 | SWI/SNF related, matrix associated, actin dependent regulator of chromatin, subfamily d, member 3 |
| LOC728489 | 728489 | DNLZ DNL-type zinc finger [*Homo sapiens*] |
| CALCA | 796 | calcitonin-related polypeptide alpha |
| COL2A1 | 1280 | collagen, type II, alpha 1 |
| DPY19L2 | 283417 | dpy-19-like 2 (*C. elegans*) |
| NULP1 | 22980 | transcription factor 25 (basic helix-loop-helix) |
| TIMP2 | 7077 | TIMP metallopeptidase inhibitor 2 |
| TPTE | 7179 | transmembrane phosphatase with tensin homology |
| SNX7 | 51375 | sorting nexin 7 |
| KIAA0746 | 23231 | KIAA0746 protein [*Homo sapiens*] |
| NQO2 | 4835 | NAD(P)H dehydrogenase, quinone 2 |
| FKBP5 | 2289 | FK506 binding protein 5 |
| ABCA1 | 19 | ATP-binding cassette, sub-family A (ABC1), member 1 |
| FAM86A | 196483 | family with sequence similarity 86, member A |
| ATXN2L | 11273 | ataxin 2-like |
| CBFB | 865 | core-binding factor, beta subunit |
| RAX | 30062 | retina and anterior neural fold homeobox |
| ZADH2-TSHZ1 | 284273 | zinc binding alcohol dehydrogenase domain containing 2 |
| ECAT8-TDRD12 | 91646 | tudor domain containing 12 |
| PROKR2 | 128674 | prokineticin receptor 2 |
| NCAM2 | 4685 | neural cell adhesion molecule 2 |
| SPEG | 10290 | SPEG complex locus |
| VWC2 | 375567 | von Willebrand factor C domain containing 2 |
| FOXR1 | 283150 | forkhead box R1 |
| TARBP2 | 6895 | TAR (HIV-1) RNA binding protein 2 [*Homo sapiens*] |
| STXBP6 | 29091 | syntaxin binding protein 6 (amisyn) |
| PRSS21 | 10942 | protease, serine, 21 (testisin) |
| LOC388335 | 388335 | transmembrane protein 220 |
| MORG1-C19orf56 | 84292 | MORG1 mitogen-activated protein kinase organizer 1 [*Homo sapiens*] |
| DUSP4 | 1846 | dual specificity phosphatase 4 |
| BARHL1 | 56751 | BarH-like homeobox 1 |
| ACOT4 | 122970 | acyl-CoA thioesterase 4 |
| SOX13 | 9580 | SRY (sex determining region Y)-box 13 |
| FAM89A | 375061 | family with sequence similarity 89, member A |
| LOC389151 | 389151 | Hypothetical gene supported by AK 127998 [*Homo sapiens*] |
| H2AFY | 9555 | H2A histone family, member Y |
| RND2-VAT1 | 8153 | Rho family GTPase 2 |

TABLE 12

| Summarized_Annotation (see footnote) | T-test (Unlogged) | Fold Change | 1$^{st}$_Start_DIST | 1$^{st}$_End_DIST |
| --- | --- | --- | --- | --- |
| WIT1 | 0.054748469 | 1.529924366 | 46 | −1177 |
|  | 0.127112854 | 2.680685148 | −374 | −243 |
|  | 0.03270418 | 5.823186847 | −243 | 685 |
|  | 0.195202702 | 3.892611484 | 685 | 1172 |
|  | 0.373029027 | 1.094911093 | 1172 |  |
| CNTNAP5 | 0.090991109 | 2.9328864 | −739 | −10 |
|  | 0.006896637 | 3.682532282 | −10 | 1194 |
| KCNG2 | 0.032172541 | 6.600879249 | −1059 | 20 |
| ACTRT2 | 0.021427804 | 3.514396256 | 68 | 1024 |

TABLE 12-continued

| Summarized_Annotation (see footnote) | T-test (Unlogged) | Fold Change | 1st_Start_DIST | 1st_End_DIST |
|---|---|---|---|---|
| PHC2 | 0.194287204 | 0.803905338 | 407 | 227 |
| | 0.009505882 | 1.556061912 | −164 | −1975 |
| OTOP1 | 0.00873557 | 1.996740331 | −507 | −1015 |
| | 0.013063838 | 2.533766322 | −1015 | −1298 |
| TUSC3 | 0.024414219 | 3.194999649 | −778 | 71 |
| | 0.058508408 | 0.796560389 | 71 | 217 |
| CEBPD | 0.44804791 | 0.922768031 | | 579 |
| | 0.145192223 | 0.892451088 | 579 | 379 |
| | 0.110294815 | 0.766167725 | 379 | −79 |
| | 0.006027516 | 1.857346861 | −170 | −248 |
| | 0.01066883 | 0.768934183 | −248 | −658 |
| | 0.014391975 | 0.505325798 | −658 | −845 |
| | 0.153326986 | 0.850129335 | −845 | −1415 |
| WDR5 | 0.582229852 | 1.067809738 | −744 | −567 |
| | 0.000380972 | 1.835084417 | −466 | −384 |
| | 0.031893346 | 1.282774124 | −384 | 133 |
| CALML3 | 0.022287889 | 3.484184157 | −86 | 625 |
| CIDEA | 0.420819368 | 1.388727137 | −200 | 75 |
| | 0.04871235 | 1.689889128 | 75 | 765 |
| CAMK2N2 | 0.731511241 | 1.169463398 | 592 | 533 |
| | 0.249109573 | 0.824518187 | 479 | 362 |
| | 0.07095243 | 0.577021958 | 362 | 10 |
| | 0.010900226 | 2.181112613 | 10 | −201 |
| STX1A | 0.038066027 | 1.128017573 | 2090 | 25 |
| | 0.022054517 | 1.590440051 | −101 | −211 |
| SMARCD3 | 0.556178898 | 0.962808769 | 3002 | 925 |
| | 0.982445133 | 1.004136503 | 925 | −156 |
| | 0.00760048 | 1.53837593 | −156 | −558 |
| LOC728489 | 0.045428198 | 1.735817023 | | 1355 |
| | 0.021707862 | 1.342200045 | 507 | 133 |
| | 0.430944223 | 0.913204715 | 133 | −452 |
| | 0.006971866 | 2.449688053 | −452 | −1335 |
| CALCA | 0.008763467 | 4.160015621 | −834 | −1625 |
| | 0.377684202 | 0.598178582 | −1625 | −1735 |
| | 0.473608532 | 0.590618877 | −1735 | |
| COL2A1 | 0.481669237 | 1.454062319 | 382 | 152 |
| | 0.473259273 | 1.0793924 | 152 | −236 |
| | 0.007187549 | 1.861014944 | −236 | −892 |
| DPY19L2 | 0.219961557 | 1.302006679 | 351 | 269 |
| | 0.044214645 | 4.443192912 | 269 | −375 |
| NULP1 | 0.01524316 | 3.066812302 | 191 | 258 |
| TIMP2 | 0.763775082 | 1.072275953 | −268 | −393 |
| | 0.046551728 | 1.873116751 | −393 | −1342 |
| TPTE | 0.007476816 | 1.810273253 | −290 | −1031 |
| SNX7 | 0.003638667 | 2.017852438 | −2221 | −87 |
| | 0.504284738 | 0.901250456 | −87 | −59 |
| | 0.146970194 | 0.165576139 | 144 | 183 |
| | 0.144854808 | 0.773781767 | 221 | 682 |
| KIAA0746 | 0.059431121 | 0.721896309 | 483 | 452 |
| | 0.714018784 | 0.960731458 | 337 | 231 |
| | 0.093368773 | 1.502582138 | 231 | −127 |
| | 0.00346599 | 1.501911337 | −127 | −178 |
| | 0.127399728 | 0.818064653 | −213 | −1003 |
| NQO2 | 0.000793319 | 1.901274447 | −432 | 100 |
| | 0.408643661 | 0.787686378 | 100 | 369 |
| | 0.012951748 | 0.806950123 | 369 | 798 |
| FKBP5 | 0.057083677 | 0.645046871 | 504 | 186 |
| | 0.043848737 | 2.617932515 | 186 | −4 |
| | 0.171069191 | 0.68483178 | −66 | −1989 |
| ABCA1 | 0.438097496 | 0.904037936 | 729 | 523 |
| | 0.051536955 | 0.554789461 | 523 | 498 |
| | 0.047002972 | 0.786989409 | 484 | 65 |
| | 0.444393657 | 0.927728865 | 65 | −284 |
| | 0.040354485 | 3.263976188 | −284 | −1836 |
| FAM86A | 0.00109257 | 1.744368579 | −76 | −2493 |
| ATXN2L | 0.671694023 | 0.961787919 | | −136 |
| | 0.013387441 | 1.63833225 | −136 | 248 |
| | 0.007404224 | 0.424910149 | 311 | 637 |
| | 0.83561023 | 1.026890115 | 637 | 1086 |
| | 0.027453829 | 0.821493784 | 1103 | 2606 |
| CBFB | 0.006047531 | 1.578011376 | −196 | 389 |
| | 0.022462991 | 0.261319251 | 389 | 421 |
| | 0.052820796 | 0.810642249 | 421 | 680 |
| | 0.232791679 | 0.452826487 | 680 | 3100 |

TABLE 12-continued

| Summarized_Annotation (see footnote) | T-test (Unlogged) | Fold Change | 1st_Start_DIST | 1st_End_DIST |
|---|---|---|---|---|
| RAX | 0.003424917 | 0.341136147 | 811 | 765 |
| | 0.53919907 | 0.894047131 | 765 | 672 |
| | 0.186308784 | 0.619095764 | 672 | 362 |
| | 0.356543793 | 0.471450723 | 362 | 264 |
| | 0.785675801 | 0.863480245 | 264 | 59 |
| | 0.006778448 | 2.563190404 | 59 | −975 |
| ZADH2-TSHZ1 | 0.004452151 | 1.544560109 | −114 | −393 |
| | 0.671630772 | 1.063818306 | −524 | 361 |
| ECAT8-TDRD12 | 0.010646042 | 2.759409695 | −657 | 109 |
| PROKR2 | 0.024442126 | 1.631635557 | −241 | −1531 |
| | 0.700170469 | 1.196057816 | −1531 | −1580 |
| | 0.19159503 | 2.281446772 | −1580 | |
| NCAM2 | 0.022725316 | 3.103743563 | −1156 | −115 |
| SPEG | 0.021002785 | 1.833326378 | −2197 | 10 |
| VWC2 | 0.001876629 | 2.670765671 | −1114 | −134 |
| | 0.091852037 | 0.241146069 | −134 | 140 |
| | 0.119177396 | 0.579919302 | 140 | 378 |
| | 0.37416275 | 1.317443723 | 378 | 907 |
| | 0.870858584 | 1.039078988 | 907 | 1012 |
| | 0.127291137 | 2.826070887 | 1012 | 1597 |
| | 0.019402038 | 1.112421128 | 1703 | 1938 |
| FOXR1 | 0.030320332 | 1.965183625 | −579 | 202 |
| | 0.110729938 | 0.766150405 | 352 | 389 |
| | 0.352099558 | 1.092009037 | 389 | 1005 |
| TARBP2 | 0.327543863 | 1.097363993 | −1372 | −1227 |
| | 0.023478606 | 1.5884659 | −1227 | 267 |
| STXBP6 | 0.5682681 | 0.868067081 | 833 | 65 |
| | 0.040075285 | 0.819455589 | 65 | −54 |
| | 0.012287693 | 0.460631262 | −54 | −106 |
| | 0.161895799 | 0.754554476 | −106 | −338 |
| | 0.004737596 | 1.650593326 | −338 | −470 |
| PRSS21 | 0.508214824 | 0.944542508 | 50 | 399 |
| | 0.014750037 | 3.52441924 | 399 | 1173 |
| LOC388335 | 0.000482273 | 2.337771731 | 326 | −211 |
| MAN2B1-MORG1 | 0.171273945 | 0.827495783 | 2235 | 37 |
| MORG1-C19orf56 | 0.016353821 | 1.881692924 | 37 | 562 |
| | 0.569957301 | 0.895717416 | 562 | 362 |
| | 0.759414503 | 1.04610352 | 362 | 1547 |
| DUSP4 | 0.108672971 | 0.499937774 | 841 | 660 |
| | 0.465309715 | 1.062043875 | 660 | 114 |
| | 0.004659006 | 1.567619335 | 114 | −431 |
| | 0.013287136 | 0.802388482 | −431 | −717 |
| | 0.195808583 | 0.744923471 | −717 | 343 |
| | 0.200661958 | 0.796484593 | 343 | −60 |
| | 0.941277939 | 1.011183854 | −60 | −1544 |
| | 0.504776305 | 0.931523396 | −1544 | −1647 |
| BARHL1 | 0.101486268 | 2.168126904 | −1699 | −273 |
| ACOT4 | 0.076392378 | 2.797523952 | −952 | 21 |
| SOX13 | 0.329456819 | 0.834384307 | −626 | 78 |
| | 0.030313663 | 1.559392038 | 78 | 353 |
| FAM89A | 0.154218745 | 0.720655055 | 891 | 373 |
| | 0.137713712 | 0.744874868 | 373 | 254 |
| | 0.339750588 | 0.901015567 | 237 | 55 |
| | 0.176723265 | 0.578928107 | −122 | −168 |
| | 0.00703254 | 1.552683921 | −168 | −975 |
| LOC389151 | 0.008145019 | 1.811889362 | 106 | −646 |
| H2AFY | 0.161579429 | 0.733802734 | 916 | 672 |
| | 0.208703051 | 0.813403124 | 672 | 582 |
| | 0.042030525 | 0.632721188 | 582 | 249 |
| | 0.006375904 | 1.528332169 | 249 | −106 |
| | 0.212726359 | 0.908201238 | −106 | −192 |
| | 0.392803941 | 0.89368228 | −192 | −120 |
| RND2-VAT1 | 0.012188821 | 1.531737049 | −957 | −29 |
| | 0.479293572 | 0.726740894 | 63 | 203 |
| | 0.344596564 | 0.89104188 | 203 | 579 |

TABLE 13

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| AKAP12 | A kinase (PRKA) anchor protein (gravin) 12 | AKAP12-M1 | gtttTGTTAGAAACGGGAGGCGttC | GAAACCAAAAACGCTACGACGCG | TCGGGTGGGCGGTTGTTTGGATT | 60 | 84 |
| ATF3 | Activating transcription factor 3 | ATF3-M1 | TGGGtTGGGGtCGGGAttC | tCCAAACATAACCAATAATACCCAAACCAACG | | 62.5 | 125 |
| ATF3 | Activating transcription factor 3 | ATF3-M2 | ttTtCGtTtCGTTCGGtCGg | CTCAAACTAACGACGCGATCG | | 60 | 100 |
| ACY1 | Aminoacylase 1 | ACY1-M1 | CGGGAtCGTttTGAGtTttCGGC | CCGAACTAACCCTACTCTAACAAACTCG | | 60 | 96 |
| ACY1 | Aminoacylase 1 | ACY1-M2 | GGGCGGTttTGAGttTGCGAttTC | TCCTATCGCTAAACTCACGCTCG | | 60 | 105 |
| ATP1B2 | ATPase, Na+/K+ transporting, beta 2 polypeptide | ATP1B2-M2 | GGGTTTAGGATCGGTGTATTTTTCGTC | AAAACACGAAAAACGAAAACGACGCG | tAGCGCGTGGTCGTGtAtttCGGAAT | 57 | |
| ATP1B2 | ATPase, Na+/K+ transporting, beta 2 polypeptide | ATP1B2-M1 | TGGTTGTTTTTTAGTTGCGCGTTTTC | AAAACGAAACTCAAAACTCGCTCCG | tCGCGGtTGAGttAttAtCGGTGtAGTGGT | 60 | |
| CAV1 | Caveolin 1, caveolae protein, 22 kDa | CAV1-M1 | CGAAGCGTTTGGGAGAtATTTtAGAAAC | ATACTTTTAATAACACTCGTTTACATCTAATCG | AAACTTAAACAAACATACAAAATTTAACATTTCCCATC | 57 | 110 |
| CTBP1 | C-terminal binding protein 1 | CTBP1-M1 | GGAtAGGCGGTTTAGAACGTGC | CCGAAACGCGACTACGAAACG | NA | 60 | 113 |
| CARS | Cysteinyl-tRNA synthetase | CARS-M1 | CGCGATGTTTCGGAGCGC | TTCCGAAACACGCCCGATCG | NA | 60.5 | |
| SMAD4/ELAC1 | ElaC homolog 1 (E. coli) | SMAD4-M1 | AGGtttAGGTttAGATTtAGAGtCGttCGtC | CCTCCCGCTCCGAATAACG | NA | 60 | 93 |
| ENG | Endoglin (Osler-Rendu-Weber syndrome 1) | ENG-M1 | AGGGTTTTTTATTTAGTGATAAAGTTCGTGG | CTAACTCATCCAACCCGACCG | tCGGTTGGtAGGCGGttTGGtttAGt | 60 | |
| FDXR | Ferredoxin reductase | FDXR-M1 | AGTAttATACGTAAGttAtTGttttCGtttCG | CTCAAATCCCCGTCTTTACCG | | 57 | 126 |
| FDXR | Ferredoxin reductase | FDXR-M2 | TTTCGTTTGTGGGCGGGTTC | ACCAACGCCAACAACGCG | | 57 | 116 |
| GPS2 | G protein pathway suppressor 2 | GPS2-M1 | TCGGtTtACGtTGtTTTGGAGttTGtATttC | ACTTTACGACAACGACACCGACG | | 60 | 125 |

TABLE 13-continued

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| GPS2 | G protein pathway suppressor 2 | GPS2-M2 | TCGTATtttTCGGAtTGTtTGttCGACGC | CGCTAACACCGAAACAACGCG | | 60 | 80 |
| GSTM4 | Glutathione S-transferase M4 | GSTM4-M1 | AGAGttTGTGGGAAtTCGGtAGtC | CCCAAAAACTCGACTATACGCGT | | 60 | 126 |
| HES2 | Hairy and enhancer of split 2 (Drosophila) | HES2-M1 | TGGCGtTtCGtTtCGtCGC | ACGAACGAAAAACTCGAACGAAAACTACG | NA | 60 | 118 |
| HINT1 | Histidine triad nucleotide binding protein 1 | HINT1-M1 | AGtttAGGTCGttAGTGCGtACGC | CCGCAAAACGTACGACGCG | | 60 | 101 |
| TGFBR2 | In multiple clusters | TGFBR2-M1 | AGAGAGtTAGGGGtTGGACGTC | TCACTCAACTTCAACTCAACGCTACG | NA | 62.5 | 120 |
| ID3 | Inhibitor of DNA binding 3, dominant negative helix-loop-helix protein | ID3-M1 | ATTTTTTGAATTCGCGGTTTCGC | ACCCTAAACGTTCACAACCCG | NA | 60 | 91 |
| ITGA3 | Integrin, alpha 3 (antigen CD49C, alpha 3 subunit of VLA-3 receptor) | ITGA3-M1 | GATAGGTGTTTGGGGGAGAAGGC | CCGAACTACGCTTTCCTTCCG | | 57 | 131 |
| ITGA3 | Integrin, alpha 3 (antigen CD49C, alpha 3 subunit of VLA-3 receptor) | ITGA3-M2 | TGGGGGtACGAAAtCGATtAGCGtTAC | ACCTATTCACCTACTCCCCGCG | | 60 | 88 |
| JAK1 | Janus kinase 1 (a protein tyrosine kinase) | JAK1-M1re | GGTAGTTTCGCGAGCGAAGTC | CCGAAAACGAAACGAAATCGCG | NA | 60.5 | |
| JUND | Jun D proto-oncogene | JUND-M2 | AGCGACGTtAttCGtAtttAATGGCGAAC | TAACGACGACTCCTACGCCG | | 60 | 105 |
| JUND | Jun D proto-oncogene | JUND-M1 | CGCtTAGGGGAGGtttTGGC | AAACGAAAACGATACCGACCTCCG | | 60 | 111 |
| MST1R | Macrophage stimulating 1 receptor (c-met-related tyrosine kinase) | MST1R-M1 | GGtttCGttttACGGtCGAtTtCGttC | GCCGCTATACACTAACGCTTAACG | NA | 60 | 83 |
| MLH1 | mutL homolog 1, colon cancer, nonpolyposis type 2 | MLH1-M | CTATCGCCGCCTCATCGT | CGTTATATATCGTTCGTAGTATTCGTGTTT | CGCGACGTCAAACGCCACTACG | 60 | 87 |

TABLE 13-continued

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| MEF2A | MADS box transcription enhancer factor 2, polypeptide A (myocyte enhancer factor 2A) | MEF2A-M1 | TGCGCGG ATGTttCGG C | GCCACCAA CGCTTCGCG | NA | 60 | 67 |
| MAL | Mal, T-cell differentiation protein | MAL-M1 | AGTTTTTA GTTTTGGA CGTTCGTA GCG | CGAAAAACC CGACCCGA ACG | TCGAAGAG GTTtAGGGC GGTGttCG | 57 | |
| MAP2K7 | Mitogen-activated protein kinase kinase 7 | MAP2K7-M1 | CGATCGG GAATTGGC GtATGC | TCCGCGCG TACGTACTT CG | NA | 60 | 124 |
| MCL1 | Myeloid cell leukemia sequence 1 (BCL2-related) | MCL1-M1 | GGCGtCG GAGtCGtC GTTAC | TACCCGAC CGAACCGA AACG | NA | 60 | 126 |
| NELL1 | NEL-like 1 (chicken) | NELL1-M1 | GGGTTTTT AGACGAA CGTAGTC GTAGC | CCACCGCT AACGCGAC GA | ACGACGTAA AACTCGAAA CCCGACCC | 60.5 | |
| NBL1 | Neuroblastoma, suppression of tumorigenicity 1 | NBL1-M2 | GGGAGTT ATTTTGAC GTCGGAG TC | GACGAAAC GACCGACA AAACG | NA | 60.5 | |
| NBL1 | Neuroblastoma, suppression of tumorigenicity 1 | NBL1-M1 | GGTTGTTT TGTTTTTC GGGCGTC | CCCGAACTA AACTTCGAC GCG | NA | 60.5 | |
| NME6 | Non-metastatic cells 6, protein expressed in (nucleoside-diphosphate kinase) | NME6-M1 | ATTTTATTT TACGTCGC GGCGTAAT | ACAAAACCC GACCACCA AACC | NA | 60.5 | |
| NOTCH2 | Notch homolog 2 (Drosophila) | NOTCH2-M1 | tTTtTGtAtT GGTtAAGtt AGCGAGtC G | TACGAATCA CTAAACCCG TCCG | | 60 | 106 |
| N33/TUSC3 | Tumor suppressor candidate 3 | N33-M | | | | 60 | |
| PTMS | Parathymosin | PTMS-M1 | CGAGttCG GGATCGA GtTAtCGC | CGCAAAACT ACGACCGT CCG | | 60 | 90 |
| PLAGL1 | Pleiomorphic adenoma gene-like 1 | PLAGL1-M1 | TTTATCGG TGATTCGG TTCGTAGG AC | AAAACCCT AACGAAAC GTCACG | TCGGtCGtC GAttttttAGtTttt CGGCGG | 60.5 | |
| PVRL3 | Poliovirus receptor-related 3 | PVRL3-M2 | TTCGTTTT AGTTTCGG TAGTGGC GTC | GCTACCGA CTAACACTT AACCGAACG | NA | 60.5 | |
| PVRL3 | Poliovirus receptor-related 3 | PVRL3-M1 | TTTTTTCG TTTTAGGT TTTCGTTA TAGGG | ACGAAAACT ACGAAACAA TCACGCTCG | NA | 60.5 | |

TABLE 13-continued

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| PFDN5 | Prefoldin subunit 5 | PFDN5-M1 | GGAGGATTATAGAGTTGTTTGGCGTAGC | CTCGACGAACAACGCTCTAACCG | NA | 60.5 | |
| PSEN1 | Presenilin 1 (Alzheimer disease 3) | PSEN1-M1 | GTGGGtCGGtCGttAACGAC | CCGCTATTTTATTTCCGATATAAAACCGCG | NA | 60 | 119 |
| PSMC3 | Proteasome (prosome, macropain) 26S subunit, ATPase, 3 | PSMC3-M1 | AAGAtTAtATTTtttAAAGGtttTCGCGGA | CGTCCTATTTTTACCGAACGCG | NA | 60 | 135 |
| PTPRO | protein tyrosine phosphatase, receptor type, O | PTPRO-M | AGCGGTGCGTTTTAGGGTAC | GCGAAAACAACAAAACGTACG | CGACAAACGCTTCCCGCGACTAAA | 60 | 81 |
| PSMD2 | Proteasome (prosome, macropain) 26S subunit, non-ATPase, 2 | PSMD2-M1 | GCGTTTCGGTTCGTTTCGGC | CCTTTTTCCCAAACCAACTCGCG | TtCGGTCGtA GGCGGGtTtTGGAG | 60.5 | |
| PRKRA | Protein kinase, interferon-inducible double stranded RNA dependent activator | PRKRA-M1 | TGttTGTGtttACGCGGGAGC | GAAACCTTAATACCGTAACTCCGACTACG | NA | 60 | 142 |
| RAB32 | RAB32, member RAS oncogene family | RAB32M | CGGTAGAGCGCGAGGTC | ATCTCGAACGCTAAAACACG | CGCTACGACTATCGAACGCGCCTC | 60 | 129 |
| RHOB | Ras homolog gene family, member B | RHOB-M1 | AGAtAGttAGtTttCGGAtttCGCGC | CGCTACGAAACTCTAACGATACCCG | NA | 60 | 78 |
| RRAD | Ras-related associated with diabetes | RRAD-M1 | GCGGTTTTGGAGTTAGAGTTTAGTGC | ACGCACTCGTAATCCGAACTCG | AGGCGGTGGtTGtAGtAGtAGCGG | 60.5 | |
| REST | RE1-silencing transcription factor | REST-M1 | GtCGGGAGGATTACGGGC | GCGTAACCGCTAAACGCG | NA | 60 | 105 |
| RGS12 | Regulator of G-protein signalling 12 | RGS12-M1 | AATTAGTTTGCGGGAACGTAGTCG | CGACGACGCTAATACGCACG | | 60 | 81 |
| STK4 | Serine/threonine kinase 4 | STK4-M1 | GCGTTATTGATATTTTAGAGATTAGCGGGTATC | CGACCCTAATCACGTAATTCGAACG | NA | 60.5 | |
| SMAD7 | SMAD, mothers against DPP homolog 7 (Drosophila) | SMAD7-M1 | TTttATGTAGGAAGtCGAGGtTGGC | CCGCTTCCCTAAAAACGACCG | NA | 60 | 112 |
| SLC39A7 | Solute carrier family 39 (zinc transporter), member 7 | SLC39A7-M1 | ACGTTTAAAGTTTTGAGGTTTAAGAGGAATC | TCCGCCCTCCTAACTATAACCG | NA | 60.5 | |

TABLE 13-continued

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| SLC39A7 | Solute carrier family 39 (zinc transporter), member 7 | SLC39A7-M2 | CGTGTTAGTGTAGGATGGATTCGTC | CCGCCTTTAAATCCCGCGA | NA | 60.5 | |
| SST | Somatostatin | SST-M1 | GGGGCGTTTTTTAGTTTGACGT | AACAACGATAACTCCGAACCTCG | AACGACTTATATACTCTCAACCGTCTCCCTCTA | 60.5 | |
| SFRS10 | Splicing factor, arginine/serine-rich 10 (transformer 2 homolog, *Drosophila*) | SFRS10-M1 | GAGttTGGtTAAGGAGCGtCGC | ACCGCTCAAAACCGAAATACTCCG | | 60 | 85 |
| SRPX | Sushi-repeat-containing protein, X-linked | SRPX-M1 | TGtCGttttCGGGAAGCGC | CGATATACGAAACTCCCCATAACGAACG | | 60 | 75 |
| HLTF/SMARCA3 | SWI/SNF related, matrix associated, actin dependent regulator of chromatin, subfamily a, member 3 | SMARCA3-M1 | GGGGTTTCGTGGTTTTTTCGC | CCCGCTACCATTCAAAACGACG | AAATAATTCCATCCGAATTCTTCCCCGCC | 60.5 | |
| TAC1 | Tachykinin, precursor 1 (substance K, substance P, neurokinin 1, neurokinin 2, neuromedin L, neurokinin alpha, neuropeptide K, neuropeptide gamma) | TAC1-M1 | GGCGGTTAATTAAATATTGAGTAGAAAGTCGC | AAATCCGAACGCGCTCTTTCG | AGAATGTtACGTGGGTtTGGAGGtTtAAGGAG | 60.5 | |
| TAX1BP3 | Tax1 (human T-cell leukemia virus type I) binding protein 3 | TAX1BP3-M1 | GAGtAGGtAGAAGATGAAGtCGTAGAGGtC | CCGAACCTCGATATCAACGCTATCG | NA | 60.5 | 85 |
| TAX1BP3 | Tax1 (human T-cell leukemia virus type I) binding protein 3 | TAX1BP3-M2 | Gt TGCGtACCGCtttAGATttCGtttC | CTTTCGAAAATCCCTACGCGTACG | NA | 60 | 111 |
| TRAF2 | TNF receptor-associated factor 2 | TRAF2-M1 | ATGTtCGTtCGTtAGGCGtACGC | CTCACCCAACGATCGCAACG | NA | 60 | 108 |
| TP53AP1 | TP53 activated protein 1 | TP53AP1-M1 | AGGGTttCGtttCGTgttTGACGTC | ACCCAAAATAAAACCAAAACCCAAAACG | | 60 | 105 |
| TP53I3 | Tumor protein p53 inducible protein 3 | TP53I3-M1 | AGTTTGTTTATTTATGTTTAAGATGGGCGG | GAAACCCAACCTCTTAACGAACG | AGtCGGGttTGCGCGGTAGTG | fail | |

TABLE 13-continued

| Target gene symbol | Target gene name | Amplicon Name | Forward Primer Sequence (5' > 3') | Reverse Primer Sequence (5' > 3') | TaqMan Probe Sequence (5' > 3') | Annealing temperature | Length of Amplicon |
|---|---|---|---|---|---|---|---|
| TP53I3 | Tumor protein p53 inducible protein 3 | TP53I3-M2 | TTTTCGGTTATTTTAGGTTTAGTCGTTTATTTC | AATAATTCTAACTCCTACGAATCCCG | NA | 60.5 | |
| UBE1 | Ubiquitin-activating enzyme E1 (A1S9T and BN75 temperature sensitivity complementing) | UBE1-M1 | AGTCGTATTTTTATGAGGCGTGG | TCCCTACTCGATTACGATTCATTCG | NA | 57 | |
| DSIPI/TSC22D3 | SC22 domain family, member 3 | DSIPI-M1 | cGtTGAAAGAGttTGAAtCGAAGCGTtC | ACATCCACGCTACCGCTCG | | 60 | 101 |
| MO25/CAB39 | Calcium binding protein 39 | MO25-M1 | CGtttTGAGTtCGtCGGtCGtTC | CCGAACCCGACTTTAACGTACG | NA | 60 | 114 |
| IHPKI | Inositol hexaphosphate kinase 1 | IHPKI-M1 | GAGGttAAGGGCGtTtCGGttTC | CAAAACCTCTACCGAAAACGTAAAACACG | NA | 60 | 128 |
| RBMS1 | RNA binding motif, single stranded interacting protein 1 | RBMS1-M1 | GATTTATAGGGTTTTCGTTCGTTTAATCGC | CGAAAACGAAACCTAAACGCCG | NA | 60.5 | |
| TGFBR2 | Transforming growth factor, beta receptor II (70/80 kDa) | TGFBR2-M2 | GGGtTCGGTtTATGACGAGtAGC | ACTCACCCGACTTCTAAACGTACG | | 60 | 133 |
| MTM/MTM1 | Myotubularin | MTM-M1 | GGttCGGtAGtCGAGtAGttTGGtAAC | ACCAAACCAACCGTAAACGCG | | 60 | 78 |
| BTG1 | B-cell translocation gene 1, anti-proliferative | BTG1-M1re | GTAGGTTTTTAGTATTGACGATAGCGAGC | GAAACCCGAAACCGCTCCG | TtAGCGtCGttAAGGtTGCGAGGG | 55 | |
| EGR1 | Early growth response 1 | EGR1-M1 | GTTACGACGGAGGCGGATTC | CGACTCCCCAAATTCTACGCG | NA | 60.5 | |
| MEN1 | Multiple endocrine neoplasia I | MEN1-M1 | GttTGAAGGGAAGGGttAATttTGAGTATtTC | AAATAATAACGAACCGAACCGCTACG | NA | 60 | 108 |
| TDE1/TMS1/SERINC3 | Serine incorporator 3 | TDE1-M1 | tCGtTtCGGTCGCGGAC | AAACATAACGATTTCTCAAACCGAAAACG | | 60 | 94 |

We claim:

1. A method comprising
measuring the methylation levels of transcriptional promoter regions of the following genes:
  i) cadherin 13, H-cadherin (heart) (CDH13),
  ii) transmembrane protein with EGF-like and two follistatin-like domains (HPP1),
  iii) cyclin-dependent kinase inhibitor 2a (p16), and
  iv) runt-related transcription factor 3 (RUNX3),
by performing real-time quantitative methylation-specific PCR (qMSP), pyrosequencing or using a methylation array with an esophageal epithelial sample collected from a human subject.

2. The method of claim 1, further comprising measuring the methylation level of a transcriptional promoter region of one or more of the following genes:
  v) tachykinin-1 (TAC1),
  vi) nel-like 1 (NELL1),
  vii) A-kinase anchoring protein 12 (AKAP12), and
  viii) somatostatin (SST).

3. The method of claim 2, wherein the methylation levels are measured for the promoter regions of a total of 5 genes.

4. The method of claim 2, wherein the methylation levels are measured for the promoter regions of a total of 6 genes.

5. The method of claim 2, wherein the methylation levels are measured for the promoter regions of a total of 7 genes.

6. The method of claim 2, wherein the methylation levels are measured for the promoter regions of a total of 8 genes.

7. The method of claim 1, further comprising measuring the methylation level of a transcriptional promoter region of one or more of the genes in Table 11.

8. The method of claim 2, further comprising measuring the methylation levels of a transcriptional promoter region of one or more of the genes in Table 11.

9. The method of any of claim 1-2, 3-6, and 7-8, wherein the methylation level is determined by qMSP, and
  a) at least one primer used in the qMSP reaction is capable of distinguishing between methylated and unmethylated nucleic acid, or
  b) a probe used in the qMSP reaction is capable of distinguishing between methylated and unmethylated nucleic acid, or
  c) both primers and a probe used in the qMSP reaction are capable of distinguishing between methylated and unmethylated nucleic acid.

10. The method of claim 1, wherein the human subject has or is suspected of having Barrett's esophagus (BE).

11. The method of claim 1, wherein the human subject has or is suspected of having esophageal adenocarcinoma (EAC) or high grade dysplasia (HGD).

12. The method of claim 1, wherein the methylation level is determined by qMSP and the primers and probes comprise SEQ ID NOS:23-26, 32-35 and 41-44.

13. The method of claim 2, wherein the methylation level is determined by qMSP and the primers and probes comprise SEQ ID NOS:27-30, 36-39, and 45-48.

\* \* \* \* \*

UNITED STATES PATENT AND TRADEMARK OFFICE
CERTIFICATE OF CORRECTION

PATENT NO. : 9,758,833 B2
APPLICATION NO. : 12/918438
DATED : September 12, 2017
INVENTOR(S) : Stephen J. Meltzer, Yulan Cheng and Zhe Jin Page 1 of 1

It is certified that error appears in the above-identified patent and that said Letters Patent is hereby corrected as shown below:

In the Specification

Column 1, Lines 13-15, should read:
STATEMENT OF GOVERNMENTAL INTEREST
This invention was made with government support under CA085069, awarded by the National Institutes of Health. The government has certain rights in the invention.

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*